(12) United States Patent
Ulven et al.

(10) Patent No.: US 8,022,063 B2
(45) Date of Patent: Sep. 20, 2011

(54) CRTH2 RECEPTOR LIGANDS FOR MEDICINAL USES

(75) Inventors: Trond Ulven, Hoersholm (DK); Thomas Frimurer, Hoersholm (DK); Øystein Rist, Hoersholm (DK); Evi Kostenis, Hoersholm (DK); Thomas Högberg, Hoersholm (DK); Jean-Marie Receveur, Hoersholm (DK); Marie Grimstrup, Hoersholm (DK)

(73) Assignee: 7TM Pharma A/S (DK)

( * ) Notice: Subject to any disclaimer, the term of this patent is extended or adjusted under 35 U.S.C. 154(b) by 662 days.

(21) Appl. No.: 11/597,873

(22) PCT Filed: May 30, 2005

(86) PCT No.: PCT/EP2005/005884
§ 371 (c)(1),
(2), (4) Date: Sep. 24, 2008

(87) PCT Pub. No.: WO2005/115382
PCT Pub. Date: Dec. 8, 2005

(65) Prior Publication Data
US 2009/0099189 A1    Apr. 16, 2009

(30) Foreign Application Priority Data

May 29, 2004  (GB) .................................. 0412198.4
Jun. 24, 2004  (GB) .................................. 0414196.6
Oct. 29, 2004  (GB) .................................. 0424018.0

(51) Int. Cl.
*A01N 43/00* (2006.01)
*C07D 231/00* (2006.01)

(52) U.S. Cl. ............................... 514/217.08; 548/374.1

(58) Field of Classification Search ............. 514/217.08; 548/374.1
See application file for complete search history.

(56) References Cited

U.S. PATENT DOCUMENTS 6,376,527 B1 *  4/2002  Goldstein et al. .............. 514/404

FOREIGN PATENT DOCUMENTS

| WO | WO 94/13643 A | 6/1994 |
|---|---|---|
| WO | WO 99/57101 A | 11/1999 |
| WO | WO 01/21591 A | 3/2001 |
| WO | WO 2004/089885 A | 10/2004 |
| WO | WO 2005/018529 A | 3/2005 |

OTHER PUBLICATIONS

Vippagunta et al. J. Advance Drug Delivery Reviews 48 (2001) 3-26.*
Ulven T et al: "Minor Structural Modifications Convert the Dual TP/CRTH2 Antagonist Ramatroban into a Highly Selective and Potent CRTH2 Antagonist" Journal of Medicinal Chemistry, American Chemical Society. Washington, vol. 48, No. 4, Feb. 24, 2005, pp. 897-900, XP002339598 ISSN: 0022-2623.
EP Application 05 770 220.1-2123—Communication Pursuant to Article 94(3) EPC, dated Oct. 12, 2010.
EP Application 05 770220.1-2107—Communication Pursuant to Article 96(2) EPC, dated May 15, 2007.
EP Application 05 770220.1—Response dated Dec. 13, 2010.
EP Application 05 770220.1-2107—Response dated Jul. 26, 2010.
EP Application 05 770220.1-2107—Response dated Sep. 24, 2007.
EP Application 05 770220.1-2107—Response dated Mar. 15, 2008.
EP Application 05 770220.1—Response dated Sep. 16, 2010.
EP Application 05 770 220.1-2123—Communication Pursuant to Article 94(3) EPC, dated Jan. 31, 2008.

* cited by examiner

*Primary Examiner* — Brandon J Fetterolf
*Assistant Examiner* — Shirley V Gembeh
(74) *Attorney, Agent, or Firm* — Banner & Witcoff, Ltd.

(57) ABSTRACT

Compounds of formula (I) are useful for the treatment of disease responsive to modulation of CRTH2 receptor activity, such as asthma, rhinitis, allergic airway syndrome, and allergic rhinobronchitis, wherein A represents a carboxyl group —COOH, or a carboxyl bioisostere; $A_1$, is hydrogen or methyl; ring $Ar^1$ is an optionally substituted phenyl ring 5- or 6-membered monocyclic heteroaryl ring, in which $AA_1CHO$— and L2 are linked to adjacent ring atoms; rings $Ar^2$, $Ar^3$ each independently represent a phenyl or 5- or 6-membered monocyclic heteroaryl ring, or a bicyclic ring system consisting of a 5- or 6-membered carbocyclic or heterocyclic ring which is benz-fused or fused to a 5- or 6-membered monocyclic heteroaryl ring, said ring or ring system being optionally substituted; t is 0 or 1; L2 and L3 are linker radicals as defined in the description.

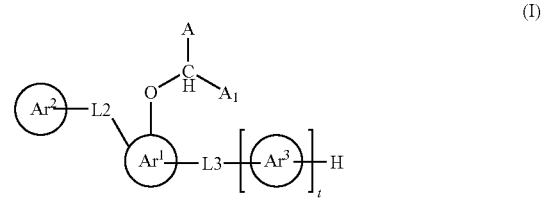

14 Claims, 1 Drawing Sheet

CRTH2 RECEPTOR LIGANDS FOR MEDICINAL USES

CROSS-REFERENCE TO RELATED APPLICATION

This application is a U.S. National Stage application of co-pending PCT application PCT/EP2005/005884, filed May 30, 2005, which claims the priority of Great Britain Patent Application No. 0412198.4, filed May 29, 2004, Great Britain Patent Application No. 0414196.6, filed Jun. 24, 2004 and Great Britain Patent Application No. 0424018.0, filed Oct. 29, 2004. These applications are incorporated herein by reference in their entireties.

This invention relates to the use of a class of compounds which are ligands of the CRTH2 receptor (Chemoattractant Receptor-homologous molecule expressed on T Helper cells type 2), in the treatment of diseases responsive to modulation of CRTH2 receptor activity, principally diseases having a significant inflammatory component. The invention also relates to novel members of that class of ligands and pharmaceutical compositions containing them.

Many classes of antiinflammatory agents are known, including the non-steroidal antiinflammatory compounds known as NSAIDs and the inhibitors of cyclooxygenase (COX-1 and COX-2). Benzoylphenylacetic acid and some benzophenone derivatives with carboxymethoxy substituents in one of the rings have been identified as antiinflammatory agents (see, for example, Khanum et. al. Bioorganic Chemistry Vol 32, No. 4, 2004, pages 211-222 and the references cited therein). Some o-phenyl carbamoyl-phenoxyacetic acids and o-benzamido-phenoxymethyl tetrazoles have been reported as potential antiinflammatory agent, see for example Drain et. al. J. Pharm. Pharmac., 1971, 23, 857-864, and ibid 1970, 22, 684-693. WO 99/15520 discloses a few benzophenone derivatives with carboxymethoxy or tetrazolylmethoxy substituents in one of the rings, synthesised as members of a group of compounds said to have activity as inhibitors of peroxisome proliferator-activated receptor (PPAR), and utility in a variety of disease states including diabetes, cardiac disease, and circulatory disease.

The natural ligand of the G-protein coupled receptor CRTH2 is prostaglandin D2. As its name implies, CRTH2 is expressed on T helper cells type 2 (Th2 cells) but it is also known to be expressed on eosinophils and basophil cells. Cell activation as a result of binding of PGD2 to the CRTH2 receptor results in a complex biological response, including release of inflammatory mediators. Elevated levels of PGD2 are therefore associated with many diseases which have a strong inflammatory component, such as asthma, rhinitis and allergies. Blocking binding of PGD2 to the CRTH2 receptor is therefore a useful therapeutic strategy for treatment of such diseases.

Some small molecule ligands of CRTH2, apparently acting as antagonists of PGD2, are known, for example as proposed in the following patent publications: WO 03/097042, WO 03/097598, WO 03/066046, WO 03/066047, WO 03/101961, WO 03/101981, GB 2388540, WO 04/089885 and WO 05/018529.

The structures of PGD2 antagonist compounds referred to in some of the foregoing publications have a bicyclic or tricyclic core ring system related to the indole core of indomethacin, a known anti-inflammatory agent, now known to bind to CRTH2. The present invention arises from the identification of a class of compounds having a monocyclic core whose substituent moieties are selected and orientated by the monocyclic core to interact with and bind to CRTH2.

The class of compounds with which this invention is concerned are thus capable of modulating CRTH2 activity, and are useful in the treatment of diseases which benefit from such modulation, for example asthma, allergy and rhinitis.

According to the present invention, there is provided the use of a compound of formula (I) or a salt, hydrate or solvate thereof in the manufacture of a composition for the treatment of disease responsive to modulation of CRTH2 receptor activity:

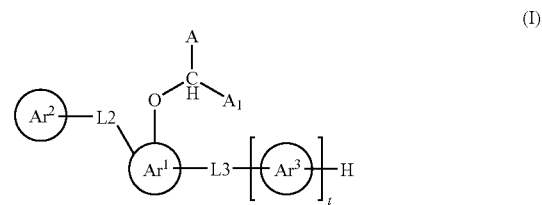

(I)

wherein

A represents a carboxyl group —COOH, or a carboxyl bioisostere;

$A_1$ is hydrogen or methyl;

ring $Ar^1$ is an optionally substituted phenyl ring or 5- or 6-membered monocyclic heteroaryl ring, in which $AA_1CHO$— and L2 are linked to adjacent ring atoms;

rings $Ar^2$, $Ar^3$ each independently represent a phenyl or 5- or 6-membered monocyclic heteroaryl ring, or a bicyclic ring system consisting of a 5- or 6-membered carbocyclic or heterocyclic ring which is benz-fused or fused to a 5- or 6-membered monocyclic heteroaryl ring, said ring or ring system being optionally substituted;

t is 0 or 1;

L2 and L3 each independently represents a divalent radical of formula -$(Alk^1)_m$-$(Z)_n$-$(Alk^2)_p$- wherein m, n and p are independently 0 or 1, $Alk^1$ and $Alk^2$ are independently optionally substituted straight or branched chain $C_1$-$C_3$ alkylene or $C_2$-$C_3$ alkenylene radicals which may contain a compatible —O—, —S— or —NR— link wherein R is hydrogen or $C_1$-$C_3$ alkyl, and Z is —O—; —S—; —C(═O)—; —SO$_2$—; —SO—; —NR—, —NRSO$_2$—, —SO$_2$NR—, —C(═O)NR—, —NRC(═O)—, —NRCONH—, —NHCONR—, —NRC(═NR)NH—, —NHC(═NR)NR—, —C(R)═N—NR—, or —NR—N═C(R)— wherein R is hydrogen or $C_1$-$C_3$ alkyl; or a divalent 5- or 6-membered monocyclic carbocyclic or heterocyclic radical, Provided that (A) the total length of L2 and L3 does not exceed that of an unbranched saturated chain of 10 carbon atoms; and (B) L2 is not —C(═O)—, —C(═O)NR—, or —NRC (═O)— when $Ar^2$ is optionally substituted phenyl; and (C) (a) L2 is not a bond and (b) p in L2 is not 0 when n is 1 and Z is aryl or heteroaryl, and (D) (a) L2 is not —O—, —SO$_2$—, —NR—, —CHR$^X$R$^Y$— or —CH(R$^X$)(OR$^Y$)—, wherein R$^X$ and R$^Y$ are independently hydrogen, halogen, $C_1$-$C_6$ alkyl, $C_2$-$C_6$ alkenyl, $C_2$-$C_6$ alkynyl, or $C_3$-$C_7$ cycloalkyl, or join to form a ring, and (b) when p is 1 and n is 1 and Z is aryl or heteroaryl then $Alk^2$ is not —CHR$^X$R$^Y$— or —CH(R$^X$)(OR$^Y$)—, wherein R$^X$ and R$^Y$ are independently hydrogen, halogen, $C_1$-$C_6$ alkyl, $C_2$-$C_6$ alkenyl, $C_2$-$C_6$ alkynyl, or $C_3$-$C_7$ cycloalkyl, or join to form a ring.

Figure 1:
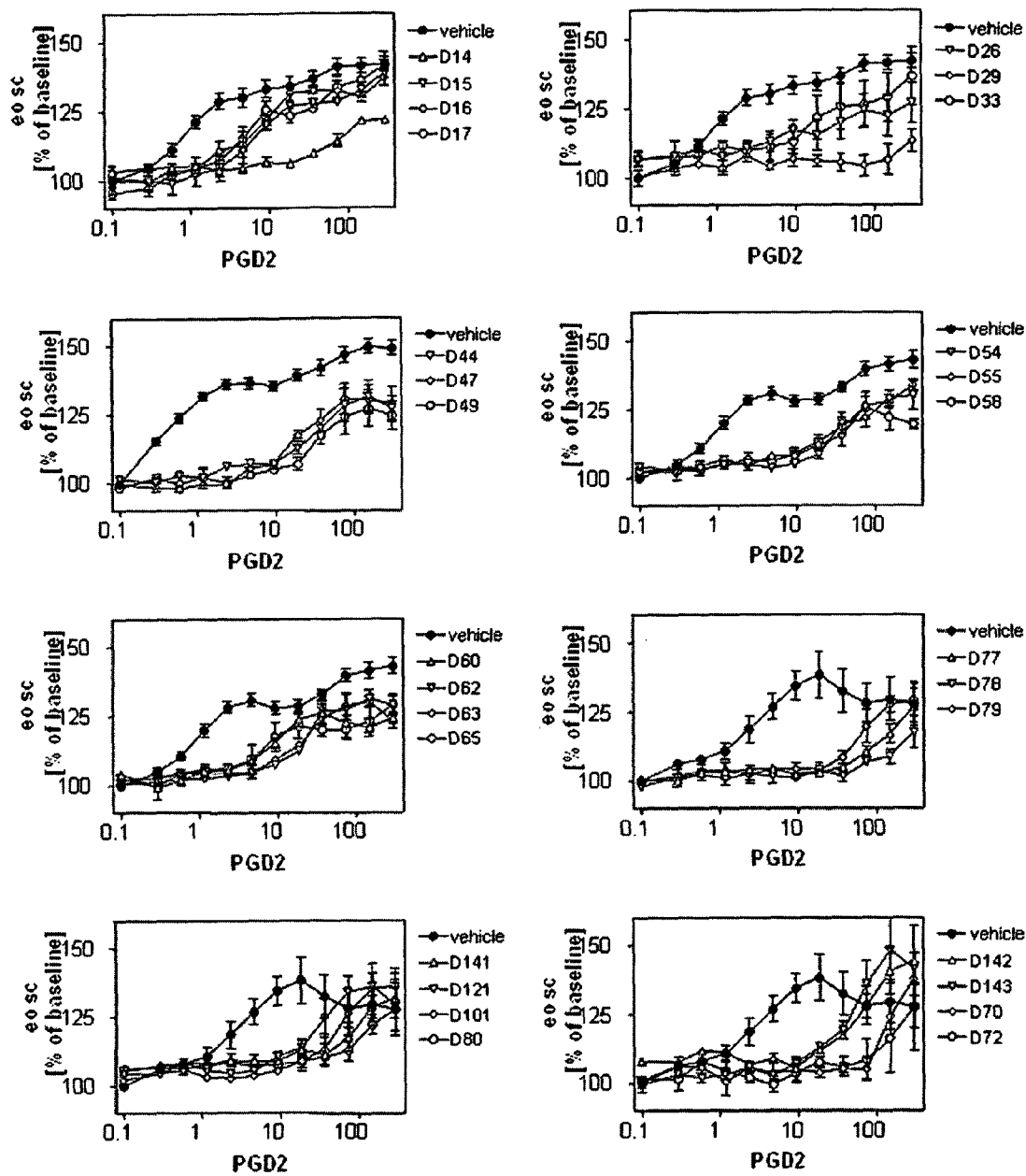
FIG. 1 depicts the ability of compounds to inhibit prostaglandin D2 induced eosihophil shape change.

In one aspect of the invention, in compounds (I), the length of each of L2 and L3 does not exceed that of an unbranched saturated chain of 5 carbon atoms and (ii) the total length of L2 and L3 does not exceed that of an unbranched saturated chain of 7 carbon atoms, and (iii) neither of L2 and L3 includes more than two R substituents different from hydrogen.

In a narrower aspect of the invention, compounds (I) as defined above wherein $A_1$ is hydrogen and Z is —O—; —S—; —C(=O)—; —SO$_2$—; —SO—; —NR—, —NRSO$_2$—, —C(=O)NR—, —NRCONH—, —NRC(=NR)NH—, or —C(R)=N—NR—, wherein R is hydrogen or $C_1$-$C_3$ alkyl; or a divalent 5- or 6-membered monocyclic carbocyclic or heterocyclic radical, may be used In another narrower aspect of the invention, compounds (I) as defined above wherein L2 is —N=CR—, —OCR$_2$C(=O)NR—N=CR—, —C(=O)NR—, —N=CR—, —C(=O)—, —CH=CHC(=O)—, —(CH$_2$)$_{0-3}$NRC(=O)—, —NRC(=O)(CH$_2$)$_{0-3}$—, —O—N=CH—, —CH$_2$NRCH$_2$—, —NR(CH$_2$)$_{1-3}$—, —(CH$_2$)$_{1-3}$NR—, —S—, —CH$_2$OCH$_2$—, —O(CH$_2$)$_{1-3}$—, —(CH$_2$)$_{1-3}$O—, —CH$_2$SCH$_2$—, —S(CH$_2$)$_{0-3}$—, —(CH$_2$)$_{0-3}$S—, a divalent ($C_2$-$C_6$)alkylene radical, a divalent ($C_2$-$C_6$)alkenylene radical, or a divalent ($C_2$-$C_6$)alkynylene radical, wherein R is hydrogen or $C_1$-$C_3$ alkyl, may be used In further narrower aspects of the invention, compounds (I) as defined above wherein L2 is —NRN=CH—, —ON=CH—, or —N=CH—; or L2 is —C(=O)—; or L2 is —NHC(=O)— or —C(=O)NH—, may be used.

An independent aspect of the invention is the use of a compound of formula (I) set out above or a salt, hydrate or solvate thereof in the manufacture of a composition for the treatment of disease responsive to modulation of CRTH2 receptor activity, in which compound (I):

A represents a carboxyl group —COOH, or a carboxyl bioisostere;
$A_1$ is hydrogen or methyl;
ring $Ar^1$ is an optionally substituted phenyl ring or 5- or 6-membered monocyclic heteroaryl ring, in which $AA_1$CHO— and L2 are linked to adjacent ring atoms;
rings $Ar^2$, $Ar^3$ each independently represent a phenyl or 5- or 6-membered monocyclic heteroaryl ring, or a bicyclic ring system consisting of a 5- or 6-membered carbocyclic or heterocyclic ring which is benz-fused or fused to a 5- or 6-membered monocyclic heteroaryl ring, said ring or ring system being optionally substituted;
t is 0 or 1;
L3 represents a divalent radical of formula -(Alk$^1$)$_m$-(Z)$_n$-(Alk$^2$)$_p$ wherein
  m, n and p are independently 0 or 1,
  Alk$^1$ and Alk$^2$ are independently optionally substituted straight or branched chain $C_1$-$C_3$ alkylene or $C_2$-$C_3$ alkenylene radicals which may contain a compatible —O—, —S— or —NR— link wherein R is hydrogen or $C_1$-$C_3$ alkyl, and
  Z is —O—; —S—; —C(=O)—; —SO$_2$—; —SO—; —NR—, —NRSO$_2$—, —SO$_2$NR—, —C(=O)NR—, —NRC(=O)—, —NRCONH—, —NHCONR—, —NRC(=NR)NH—, —NHC(=NR)NR—, —C(R)=N—NR—, or —NR—N=C(R)— wherein R is hydrogen or $C_1$-$C_3$ alkyl; or a divalent 5- or 6-membered monocyclic carbocyclic or heterocyclic radical;

L2 represents a divalent radical selected from one of the following formulae (sometimes called "L2 set A" herein), wherein either (i) the bond marked * is attached to $Ar^2$ while the bond marked ** is attached to $Ar^1$, or (ii) the bond marked * is attached to $Ar^1$ while the bond marked ** is attached to $Ar^2$:

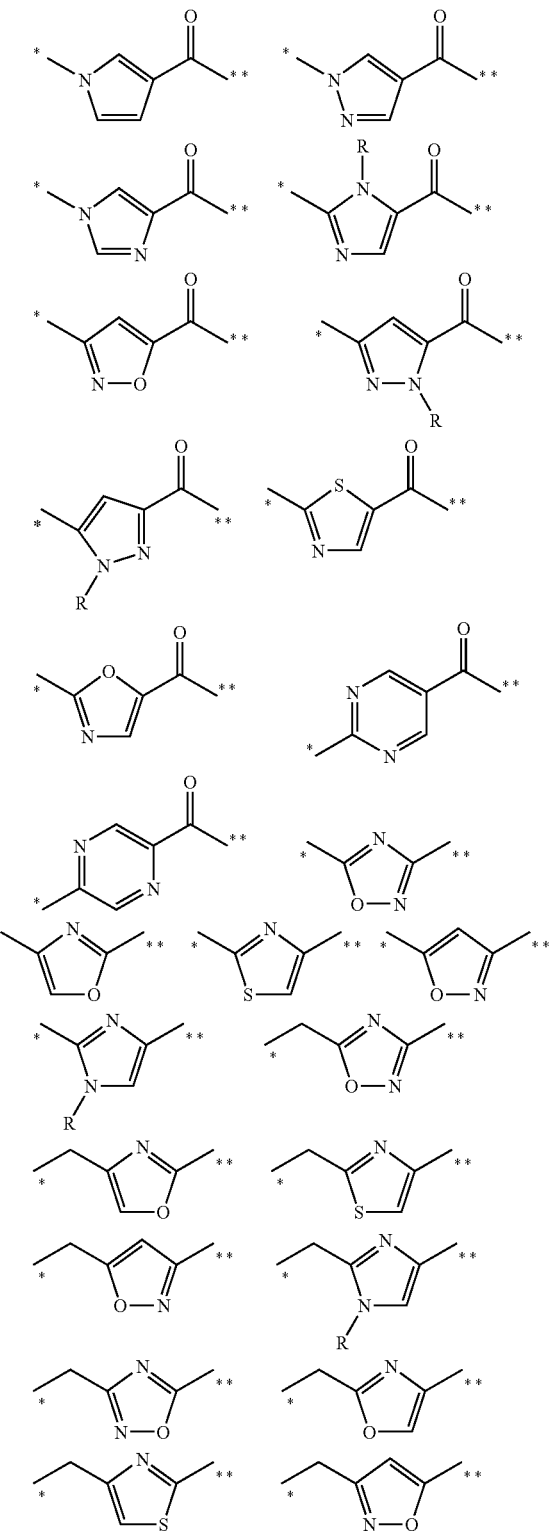

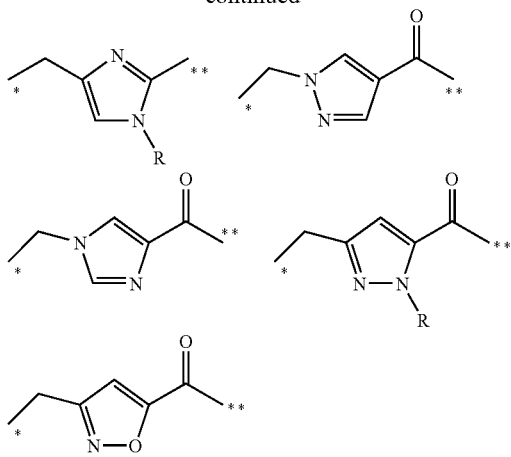

wherein R is hydrogen or $C_1$-$C_3$ alkyl; and
the total length of L2 and L3 does not exceed that of an unbranched saturated chain of 10 carbon atoms.

In a narrower definition of this aspect of the invention, in the compounds (I), (i) the length of L3 does not exceed that of an unbranched saturated chain of 5 carbon atoms and (ii) the total length of L2 and L3 does not exceed that of an unbranched saturated chain of 7 carbon atoms, and (iii) L3 does not include more than two R substituents different from hydrogen.

In the two immediately foregoing aspects of the invention, in the compounds (I), A1 may be hydrogen and L2 may be one of the following formulae (sometimes called "L2 set B" herein) wherein the bond marked * is attached to $Ar^2$ while the bond marked ** is attached to $Ar^1$:

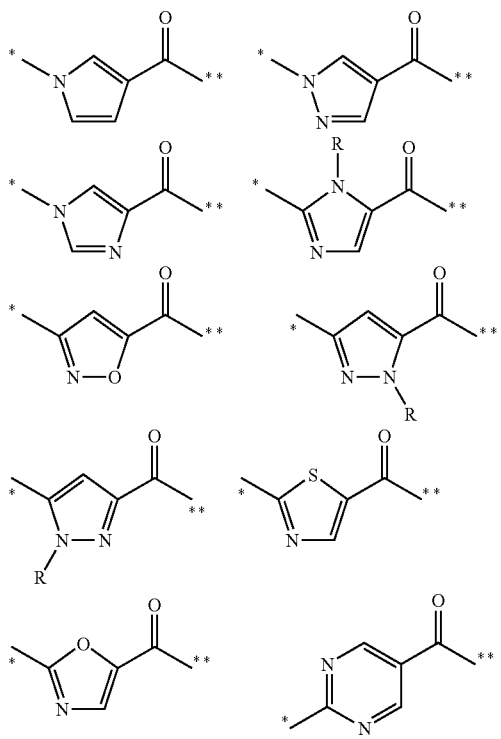

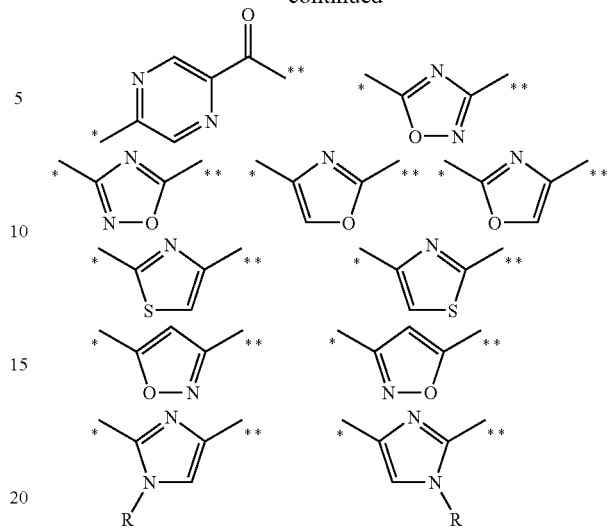

wherein R is hydrogen or $C_1$-$C_3$ alkyl.

The compounds with which the invention is concerned are defined by reference to formula (I) as a result of studies towards elucidation of the ligand binding site of CRTH2. Such studies led to the overall conclusion that a general pharmacophore comprising one negatively charged moiety, represented by $AA_1CHO$—, and two aromatic and/or hydrophobic moieties, represented by $Ar^2L2$ and either $H(Ar^3)_rL3$-$Ar^1$ or only $Ar^1$, oriented in an approximate triangle, would form an arrangement for interaction with the receptor binding site. It was concluded that the substituent groupings $AA_1CHO$— and $Ar^2L2$- should be on adjacent ring atoms of $Ar^1$. The linkers L2 and L3 provide some flexibility to the molecule to facilitate optimum binding. The restrictions on the lengths of, and substitutions in, the linkers L2 and L3 are in order to restrict the total molecular size and complexity of structures for use in accordance with the invention. For the avoidance of doubt, the total length of L2 and L3 is, for the purposes of this description and claims, the sum n2+n3, where n2 is the number of connected atoms in the shortest chain of atoms from terminal atom to terminal atom of linker L2, and n3 is the number of connected atoms in the shortest chain of atoms from terminal atom to terminal atom of linker L2. Preferably the compounds with which the invention is concerned should have a molecular weight of no more than 600. Optional substituents in any element of the compounds (I) are permitted as in the definition of compounds (I). Such substituents can modulate pharmacokinetic and solubility properties, as well as picking up additional binding interactions with the receptor.

In another aspect, the invention provides a method of treatment of a subject suffering from a disease responsive to modulation of CRTH2 receptor activity, which comprised administering to the subject an amount of a compound (I) as defined and described above effective to ameliorate the disease.

In particular, compounds with which the invention is concerned are useful in the treatment of disease associated with elevated levels of prostaglandin D2 (PGD2) or one or more active metabolites thereof.

Examples of such diseases include asthma, rhinitis, allergic airway syndrome, allergic rhinobronchitis, bronchitis, chronic obstructive pulmonary disease (COPD), nasal polyposis, sarcoidosis, farmer's lung, fibroid lung, cystic fibrosis, chronic cough, conjunctivitis, atopic dermatitis, Alzheimer's disease, amyotrophic lateral sclerosis, AIDS dementia complex, Huntington's disease, frontotemporal dementia, Lewy body dementia, vascular dementia, Guillain-Barre syndrome, chronic demyelinating polyradiculoneurophathy, multifocal motor neuropathy, plexopathy, multiple sclerosis, encephalomyelitis, panencephalitis, cerebellar degeneration and encephalomyelitis, CNS trauma, migraine, stroke, rheumatoid arthritis, ankylosing spondylitis, Behçet's Disease, bursitis, carpal tunnel syndrome, inflammatory bowel disease, Crohn's disease, ulcerative colitis, dermatomyositis, Ehlers-Danlos Syndrome (EDS), fibromyalgia, myofascial pain, osteoarthritis (OA), osteonecrosis, psoriatic arthritis, Reiter's syndrome (reactive arthritis), sarcoidosis, scleroderma, Sjogren's Syndrome, soft tissue disease, Still's Disease, tendinitis, polyarteritis Nodossa, Wegener's Granulomatosis, myositis (polymyositis dermatomyositis), gout, atherosclerosis, lupus erythematosus, systemic lupus erythematosus (SLE), type I diabetes, nephritic syndrome, glomerulonephritis, acute and chronic renal failure, eosinophilia fascitis, hyper IgE syndrome, sepsis, septic shock, ischemic reperfusion injury in the heart, allograft rejection after transplantations, and graft versus host disease.

However, the compounds with which the invention is concerned are primarily of value for the treatment asthma, rhinitis, allergic airway syndrome, and allergic rhinobronchitis.

Many compounds of formula (I) above are novel in their own right, and the invention includes such novel compounds per se.

As used herein, the term "$(C_a\text{-}C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent $(C_a\text{-}C_b)$alkylene radical" wherein a and b are integers refers to a saturated hydrocarbon chain having from a to b carbon atoms and two unsatisfied valences.

As used herein the term "$(C_a\text{-}C_b)$alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent $(C_a\text{-}C_b)$alkenylene radical" means a hydrocarbon chain having from a to a carbon atoms, at least one double bond, and two unsatisfied valences.

As used herein the term "$C_a\text{-}C_b$ alkynyl" wherein a and b are integers refers to straight chain or branched chain hydrocarbon groups having from two to six carbon atoms and having in addition one triple bond. This term would include for example, ethynyl, 1- and 2-propynyl, 1-, 2- and 3-butynyl, 1,2-, 3- and 4-pentynyl, 1-, 2-, 3-, 4- and 5-hexynyl, 3-methyl-1-butynyl, 1-methyl-2-pentynyl.

As used herein the term "divalent $(C_a\text{-}C_b)$alkynylene radical" wherein a and b are integers refers to a divalent hydrocarbon chain having from 2 to 6 carbon atoms, at least one triple bond, and two unsatisfied valences.

As used herein the term "carbocyclic" refers to a mono-, bi- or tricyclic radical having up to 16 ring atoms, all of which are carbon, and includes aryl and cycloalkyl.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzothienyl, furyl, benzofuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyridazinyl, triazinyl, indolyl and indazolyl.

As used herein the unqualified term "heterocyclyl" or "heterocyclic" includes "heteroaryl" as defined above, and in addition means a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzofuranyl, pyranyl, isoxazolyl, benzimidazolyl, methylenedioxyphenyl, ethylenedioxyphenyl, maleimido and succinimido groups.

The term "carboxyl bioisostere" is a term familiar to medicinal chemists (see for example "The Organic Chemistry of Drug Design and Drug Action", by Richard B. Silverman, pub. Academic Press, 1992), and refers to a group which has similar acid-base characteristics to those of a carboxyl group. Well known carboxyl bioisosteres include —SO$_2$NHR or —P(=O)(OH)(OR) wherein R is, for example, hydrogen methyl or ethyl, —SO$_2$OH, —P(=O)(OH)(NH$_2$), —C(=O) NHCN and groups of formulae:

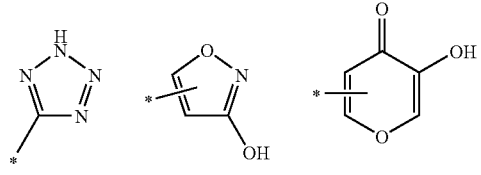

Unless otherwise specified in the context in which it occurs, the term "substituted" as applied to any moiety herein means substituted with up to four compatible substituents, each of which independently may be, for example, $(C_1\text{-}C_6)$ alkyl, $(C_1\text{-}C_6)$alkoxy, hydroxy, hydroxy$(C_1\text{-}C_6)$alkyl, mercapto, mercapto$(C_1\text{-}C_6)$alkyl, $(C_1\text{-}C_6)$alkylthio, halo (including fluoro, bromo and chloro), fully or partially fluorinated $(C_1\text{-}C_3)$alkyl, $(C_1\text{-}C_3)$alkoxy or $(C_1\text{-}C_3)$alkylthio such as trifluoromethyl, trifluoromethoxy, and trifluoromethylthio, nitro, nitrile (—CN), oxo, phenyl, phenoxy, —COOR$^A$, COR$^A$, —OCOR$^A$, —SO$_2$R$^A$, —CONR$^A$R$^B$, —SO$_2$NR$^A$R$^B$, —NR$^A$R$^B$, —OCONR$^A$R$^B$, —NR$^B$COR$^A$, —NR$^B$COOR$^A$, —NR$^B$SO$_2$OR$^A$ or —NR$^A$CONR$^A$R$^B$ wherein R$^A$ and R$^B$ are independently hydrogen or a $(C_1\text{-}C_6)$alkyl group or, in the case where R$^A$ and R$^B$ are linked to the same N atom, R$^A$ and R$^B$ taken together with that nitrogen may form a cyclic amino ring. Where the substituent is phenyl or phenoxy, the phenyl ring thereof may itself be substituted by any of the above substituents except phenyl or phenoxy. An "optional substituent" may be one of the foregoing substituent groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomeres with R or S stereochemistry at each chiral axis. The invention includes all such enantiomers and diastereoisomers and mixtures thereof.

Use of prodrugs, such as esters, of compounds (I) with which the invention is concerned is also part of the invention.

For use in accordance with the above aspects of the invention the following structural characteristics may be present, in any compatible combination, in the compounds (I):

L2 may be a member of L2 set A above (and of course L2 set A includes L2 set B);

L2 may be —N=CR—, —OCR$_2$C(=O)NR—N=CR—, —C(=O)NR—, —N=CR—, —C(=O)—, —CH=CHC(=O)—(CH$_2$)$_{0-3}$NRC(=O)—, —NRC(=O)(CH$_2$)$_{0-3}$—, —O—N=CH—, —CH$_2$NRCH$_2$—, —NR(CH$_2$)$_{1-3}$—, —(CH$_2$)$_{1-3}$NR—, —S—, —CH$_2$OCH$_2$—, —O(CH$_2$)$_{1-3}$—, —(CH$_2$)$_{1-3}$O—, —CH$_2$SCH$_2$—, —S(CH$_2$)$_{0-3}$—, —(CH$_2$)$_{0-3}$S—, a divalent ($C_2$-$C_6$)alkylene radical, a divalent ($C_2$-$C_6$)alkenylene radical, or a divalent ($C_2$-$C_6$)alkynylene radical, wherein R is hydrogen or $C_1$-$C_3$ alkyl;

L2 may be —NRN=CH—, —ON=CH—, —N=CH—, —C(=O)—, —NHC(=O)— or —C(=O)NH—;

Ar$^2$ may be an optionally substituted phenyl or 5- or 6-membered nitrogen-containing heteroaryl ring, for example pyridyl, pyrimidyl, diazolyl, thiazolyl, oxazolyl, triazinyl, quinolinyl, pyrrolyl, furanyl, thiazolyl, Optional substituents in Ar$^2$ may be selected from fluoro, chloro, bromo, ($C_1$-$C_3$)alkyl, trifluoromethyl, ($C_1$-$C_3$) alkoxy, trifluoromethoxy, trifluoromethylthio, dimethylamino, cyano, ($C_1$-$C_3$alkyl)SO$_2$—, NH$_2$SO$_2$—, ($C_1$-$C_3$alkyl)NHSO$_2$—, ($C_1$-$C_3$alkyl)$_2$NSO$_2$—, and nitro;

Ar$^1$ may be an optionally substituted 5- or 6-membered nitrogen-containing heteroaryl ring, for example pyridyl, pyrimidyl, diazolyl, thiazolyl, oxazolyl, triazinyl, quinolinyl, pyrrolyl, furanyl, thiazolyl, and wherein L3 may be linked to a ring carbon in (for a 6-membered ring) the 4 position thereof relative to the ACHA$_1$O— radical or (for a 5-membered ring) the 4 position thereof counting the ACHA$_1$O— radical as in position 1 and the Ar$^2$L2- radical as in position 2 thereof;

Ar$^1$ may be an optionally substituted phenyl ring wherein L3 is linked to the 4 position thereof relative to the ACHA$_1$O— radical;

when t is 1, Ar$^3$ may be an optionally substituted phenyl ring, or an optionally substituted 5- or 6-membered heteroaryl ring, for example pyridyl, pyrimidyl, diazolyl, thiazolyl, oxazolyl, triazinyl, quinolinyl, pyrrolyl, furanyl, or thiazolyl;

optional substituents in ring Ar$^1$ or Ar$^3$ may be selected from fluoro, chloro, bromo, iodo, cyano, nitro, trifluoromethyl, trifluoromethoxy, trifluoromethylthio, ($C_1$-$C_3$alkyl)SO$_2$—, NH$_2$SO$_2$—, ($C_1$-$C_3$alkyl)NHSO$_2$—, ($C_1$-$C_3$alkyl)$_2$NSO$_2$—, $C_1$-$C_6$ alkyl, $C_1$-$C_6$ alkoxy, cycloalkyl, aryl, aryloxy, aryl($C_1$-$C_6$) or aryl($C_1$-$C_6$ alkoxy)-;

when t is 0, L3 may be a bond;

A may be —COOH or a carboxyl bioisostere selected from —SO$_2$NHR and —P(=O)(OH)(OR) wherein R is hydrogen methyl or ethyl, —SO$_2$OH, —P(=O)(OH)(NH$_2$), —C(=O)NHCN and groups of formulae:

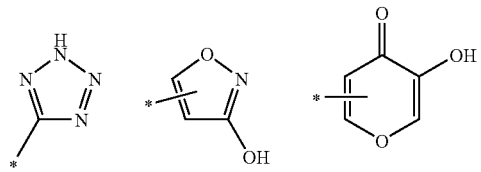

It is currently preferred that A be carboxyl;

A$_1$ may be hydrogen or methyl.

Compounds (I) for use in accordance with the invention include those of formula (IV) and salts, hydrates or solvates thereof, which are believed novel per se, and which form another aspect of the invention:

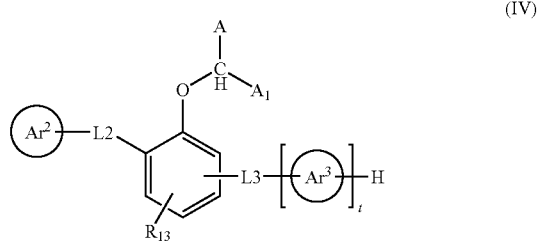

(IV)

wherein A, A1, L3, Ar$^3$, Ar$^2$, and t are as defined and discussed above in relation to formula (I), R13 represents hydrogen or one or more optional substituents, and L2 is a member of the L2 set A, as defined above. This includes the case where A$_1$ is hydrogen and L2 is a member of the L2 set B as defined above.

The following structural characteristics may be present in compounds (IV), in any compatible combination:

A may be —COOH, or a carboxyl bioisostere selected from —SO$_2$NHR and —P(=O)(OH)(OR) wherein R is hydrogen methyl or ethyl, —SO$_2$OH, —P(=O)(OH)(NH$_2$), —C(=O)NHCN and groups of formulae:

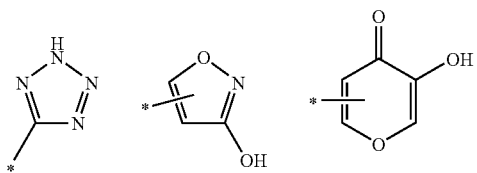

Currently it is preferred that A be carboxyl.

R$_{13}$ may represent one or more substituents selected from fluoro, chloro, bromo, iodo, cyano, nitro, trifluoromethyl, trifluoromethoxy, trifluoromethylthio, (C$_1$-C$_3$alkyl)SO$_2$—, NH$_2$SO$_2$—, (C$_1$-C$_3$alkyl)NHSO$_2$—, (C$_1$-C$_3$alkyl)$_2$NSO$_2$—, C$_1$-C$_6$alkyl, C$_1$-C$_6$ alkoxy, cycloalkyl, aryl, aryloxy, aryl(C$_1$-C$_6$) or aryl(C$_1$-C$_6$ alkoxy)-.

A$_1$ may be methyl or A$_1$ may be hydrogen.

One preferred subset of the compounds (IV) has formula (IVA)

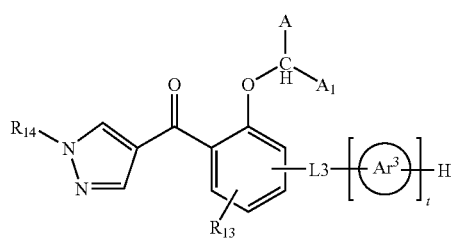

wherein A, A$_1$ L3, t, Ar$^3$, R$_{13}$ are as defined and discussed above in relation to compounds of formula (I) and (IV) and R$_{14}$ is optionally substituted phenyl or 5- or 6-membered heteroaryl.

Another preferred subset of the compounds (IV) has formula (IVB):

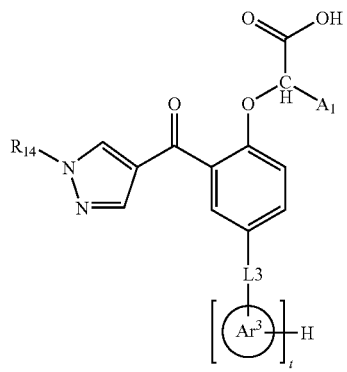

wherein A$_1$, L3, t, and Ar$^3$ are as defined and discussed above in relation to formulae (I), (IV) and (IVA), and R$_{14}$ is optionally substituted phenyl or 5- or 6-membered heteroaryl Another preferred subset of the compounds (IV) has formula (IVC):

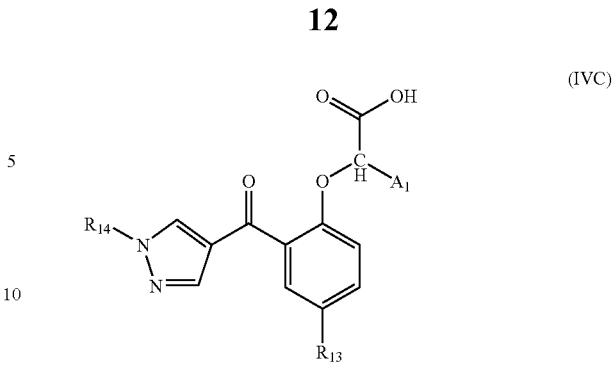

wherein R$_{13}$ represents a substituent selected from fluoro, chloro, bromo, iodo, (C$_1$-C$_6$)alkyl, trifluoromethyl, (C$_1$-C$_6$) alkoxy, (C$_1$-C$_6$)alkylmercapto, trifluoromethoxy, trifluoromethylthio, dimethylamino, cyano, (C$_1$-C$_3$alkyl)SO$_2$—, NH$_2$SO$_2$—, (C$_1$-C$_3$alkyl)NHSO$_2$—, (C$_1$-C$_3$alkyl)$_2$NSO$_2$—, and nitro, and R$_{14}$ is optionally substituted phenyl or 5- or 6-membered heteroaryl. In this subset, R$_{14}$ may be a 2-substituted, 2,4-disubstituted, 2,6-disubstituted or 2,4,6-trisubstituted phenyl ring where the substituents are selected from fluoro, chloro, bromo, iodo, (C$_1$-C$_6$)alkyl, trifluoromethyl, (C$_1$-C$_6$)alkoxy, (C$_1$-C$_6$)alkylmercapto, trifluoromethoxy, trifluoromethylthio, dimethylamino, (C$_1$-C$_3$alkyl)SO$_2$—, NH$_2$SO$_2$—, (C$_1$-C$_3$alkyl)NHSO$_2$—, (C$_1$-C$_3$alkyl)$_2$NSO$_2$—, and cyano. This subset specifically includes compounds wherein A$_1$ is hydrogen.

In any compound (I), (IV) (IVA), (IVB) or IVC) defined and discussed above, wherein A1 is methyl, the carbon atom to which it is attached preferrably has the S stereochemical configuration.

Specific novel compounds of the invention are the following:

4-chloro-2-(1-phenyl-1H-pyrazole-4-carbonyl)phenoxyacetic acid, 4-bromo-2-(1-phenyl-1H-pyrazole-4-carbonyl)phenoxyacetic acid,

[4-bromo-2-(1-pyridin-2-yl-1H-pyrazole-4-carbonyl)phenoxy]acetic acid,

{4-bromo-2-[1-(2-chlorophenyl)-1H-pyrazole-4-carbonyl]phenoxy}acetic acid,

{4-bromo-2-[1-(3-chlorophenyl)-1H-pyrazole-4-carbonyl]phenoxy}acetic acid,

{4-bromo-2-[1-(4-bromophenyl)-1H-pyrazole-4-carbonyl]phenoxy}acetic acid,

{4-bromo-2-[1-(4-chlorophenyl)-1H-pyrazole-4-carbonyl]phenoxy}acetic acid,

{4-bromo-2-[1-(2-ethylphenyl)-1H-pyrazole-4-carbonyl]phenoxy}acetic acid,

{4-bromo-2-[1-(2-bromophenyl)-1H-pyrazole-4-carbonyl]phenoxy}acetic acid,

{4-bromo-2-[1-(2-fluorophenyl)-1H-pyrazole-4-carbonyl]phenoxy}acetic acid,

{4-bromo-2-[1-(2-trifluoromethylphenyl)-1H-pyrazole-4-carbonyl]phenoxy}acetic acid, {4-bromo-2-[1-(3-bromophenyl)-1H-pyrazole-4-carbonyl]phenoxy}acetic acid, {4-bromo-2-[1-(2,4-dichlorophenyl)-1H-pyrazole-4-carbonyl]phenoxy}acetic acid, {2-[1-(2-chlorophenyl)-1H-pyrazole-4-carbonyl]-4-nitrophenoxy}acetic acid, {4-bromo-2-[1-(2,6-dichlorophenyl)-1H-pyrazole-4-carbonyl]phenoxy}acetic acid, {2-[1-(2-bromophenyl)-1H-pyrazole-4-carbonyl]-4-ethylphenoxy}acetic acid, {4-bromo-2-[1-(2,4-dibromophenyl)-1H-pyrazole-4-carbonyl]phenoxy}acetic acid,
{4-bromo-2-[1-(4-bromo-2-chlorophenyl)-1H-pyrazole-4-carbonyl]phenoxy}acetic acid,
{4-bromo-2-[1-(2,4,6-trichlorophenyl)-1H-pyrazole-4-carbonyl]phenoxy}acetic acid,
2-[4-bromo-2-(1-phenyl-1H-pyrazole-4-carbonyl)phenoxy]propionic acid,
(S)-2-[4-bromo-2-(1-phenyl-1H-pyrazole-4-carbonyl)phenoxy]propionic acid,
2-{4-Bromo-2-[1-(2-chlorophenyl)-1-H-pyrazole-4-carbonyl]phenoxy}propionic acid,
(S)-2-{4-Bromo-2-[1-(2-chlorophenyl)-1-H-pyrazole-4-carbonyl]phenoxy}-propionic acid,
2-{4-Bromo-2-[1-(2,6-dichlorophenyl)-1H-pyrazole-4-carbonyl]phenoxy}propionic acid,
(S)-2-{4-Bromo-2-[1-(2,6-dichlorophenyl)-1H-pyrazole-4-carbonyl]phenoxy}propionic acid,
{4-Bromo-2-[1-(2-ethoxyphenyl)-1H-pyrazole-4-carbonyl]phenoxy}acetic acid,
{4-Bromo-2-[1-(4-bromo-2-ethylphenyl)-1H-pyrazole-4-carbonyl]phenoxy}acetic acid,
{4-Bromo-2-[1-(2-phenoxyphenyl)-1H-pyrazole-4-carbonyl]phenoxy}acetic acid,
{4-Bromo-2-[1-(2-methylthiophenyl)-1H-pyrazole-4-carbonyl]phenoxy}acetic acid,
{4-Bromo-2-[1-(2-bromo-4-methylphenyl)-1H-pyrazole-4-carbonyl]phenoxy}acetic acid,
2-{4-Bromo-2-[1-(4-bromo-2-ethylphenyl)-1H-pyrazole-4-carbonyl]phenoxy}propionic acid,
2-{4-Bromo-2-[1-(2-phenoxyphenyl)-1H-pyrazole-4-carbonyl]phenoxy}propionic acid,
(S)-2-{4-Bromo-2-[1-(2-phenoxyphenyl)-1H-pyrazole-4-carbonyl]phenoxy}propionic acid,
2-{4-Bromo-2-[1-(2-methylthio)-1H-pyrazole-4-carbonyl]phenoxy}propionic acid,
(S)-2-{4-Bromo-2-[1-(2-methylthio)-1H-pyrazole-4-carbonyl]phenoxy}propionic acid,
{4-Bromo-2-[1-(2,4-dimethylphenyl)-1H-pyrazole-4-carbonyl]phenoxy}acetic acid,
{4-Bromo-2-[1-(4-chloro-2-methylphenyl)-1H-pyrazole-4-carbonyl]phenoxy}acetic acid,
{4-Bromo-2-[1-(2,5-dichlorophenyl)-1H-pyrazole-4-carbonyl]phenoxy}acetic acid,
2-{4-Bromo-2-[1-(4-chloro-2-methylphenyl)-1H-pyrazole-4-carbonyl]phenoxy}propionic acid,
2-{4-Bromo-2-[1-(2,4,6-trichlorophenyl)-1H-pyrazole-4-carbonyl]phenoxy}propionic acid,
{4-Bromo-2-[1-(2,6-diethyl-phenyl)-1H-pyrazole-4-carbonyl]phenoxy}acetic acid,
{4-Bromo-2-[1-(2,6-dimethylphenyl)-1H-pyrazole-4-carbonyl]phenoxy}acetic acid
{4-Bromo-2-[1-(2-ethyl-6-methylphenyl)-1H-pyrazole-4-carbonyl]phenoxy}acetic acid,
{4-Bromo-2-[1-(2-chloro-6-methylphenyl)-1H-pyrazole-4-carbonyl]phenoxy}acetic acid,
{4-Bromo-2-[1-(3,5-dichloropyridin-4-yl)-1H-pyrazole-4-carbonyl]phenoxy}acetic acid,
[4-Bromo-2-(1-naphthalen-1-yl-1H-pyrazole-4-carbonyl)phenoxy]acetic acid,
{4-Bromo-2-[2-(4-chlorobenzyl)thiazol-4-yl]phenoxy}acetic acid,
{4-Bromo-2-[3-(4-fluoro-phenyl)-[1,2,4]oxadiazol-5-yl]phenoxy}acetic acid,
{4-Bromo-2-[3-(4-methoxy-phenyl)-[1,2,4]oxadiazol-5-yl]phenoxy}acetic acid,
{4-Bromo-2-[3-(4-chlorophenyl)-[1,2,4]oxadiazol-5-yl]phenoxy}acetic acid,
{4-Bromo-2-[3-(4-fluoro-benzyl)-[1,2,4]oxadiazol-5-yl]-phenoxy}-acetic acid,
{4-Bromo-2-[3-(2,6-dichloro-benzyl)-[1,2,4]oxadiazol-5-yl]-phenoxy}-acetic acid,
{4-Bromo-2-[3-(2-trifluoromethylbenzyl)-[1,2,4]oxadiazol-5-yl]phenoxy}-acetic acid,
4-Bromo-2-[3-(2,6-dichloro-phenyl)isoxazole-5-carbonyl]phenoxy}acetic acid,
{4-Bromo-2-[3-(1-phenylcyclopropyl)-[1,2,4]oxadiazol-5-yl]phenoxy}acetic acid,
{4-Bromo-2-[3-(2,4-dichlorophenyl)-[1,2,4]oxadiazol-5-yl]phenoxy}acetic acid,
and salts, hydrates and solvates thereof.

The invention also includes pharmaceutical compositions comprising a compound belonging to the above described compounds of formula (IV), (IVA), (IVB) or (IVC), together with a pharmaceutically acceptable carrier.

Compositions

As mentioned above, the compounds with which the invention is concerned are capable of modulating CRTH2 activity, and are useful in the treatment of diseases which benefit from such modulation. Examples of such diseases are referred to above, and include asthma, allergy and rhinitis.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The drug may also be formulated for inhalation, for example as a nasal spray, or dry powder or aerosol inhalers.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The compounds with which the invention is concerned may be administered alone, or as part of a combination therapy with other drugs used for treatment of diseases with a major inflammatory component. In the case of asthma, rhinitis, and allergic airway syndrome such drugs include corticosteroids, long-acting inhaled beta agonists, cromolyn, nedocromil, theophylline, leukotriene receptor antagonists, antihistamines, and anticholinergics (e.g. ipratropium), and are often administered as nasal sprays, dry powder or aerosol inhalers.

In the case of arthritis and related inflammatory diseases other known drugs include glucocorticoids, NSAIDs (Non Steroidal Anti-inflammatory Drugs—conventional prostagiandin synthesis inhibitors, COX-2 inhibitors, salicylates), and DMARDs (disease-modifying anti-rheumatic drugs such as methotrexate, sulfasalazine, gold, cyclosporine).

Synthetic Routes

There are multiple synthetic strategies for the synthesis of the compounds (I) with which the present invention is concerned, but all rely on known chemistry, known to the synthetic organic chemist. Thus, compounds according to Formula I can be synthesised according to procedures described in the standard literature and are well-known to the one skilled in the art. Typical literature sources are "*Advanced organic chemistry*", 4$^{th}$ Edition (Wiley), J March, "*Comprehensive Organic Transformation*", 2$^{nd}$ Edition (Wiley), R. C. Larock, "*Handbook of Heterocyclic Chemistry*", 2$^{nd}$ Edition (Pergamon), A. R. Katritzky), review articles such as found in "*Synthesis*", "*Acc. Chem. Res.*", "*Chem. Rev*", or primary literature sources identified by standard literature searches online or from secondary sources such as "*Chemical Abstracts*" or "*Beilstein*".

In the discussion which follows, A represents a carboxylic acid, a carboxyl bioisostere, or a protected carboxylic acid or bioisostere, or a precursor of these. In the latter case, a deprotection step is implied. $A_1$ represents hydrogen or methyl.

Many compounds claimed in this invention may be synthesized by reacting a phenol precursor with LG-CH($A_1$)-A, where LG is a leaving group and A is a carboxylic acid or a protected analog or precursor, or a bioiosotere or a protected analog of this.

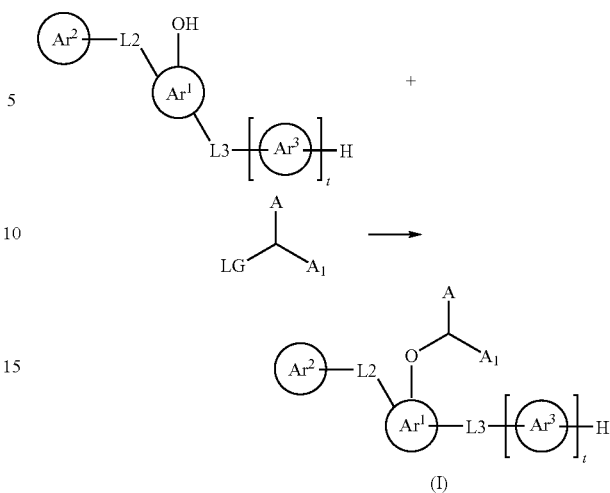

The linker L2 can be formed by joining two appropriately functionalised and, if needed, suitably protected fragments containing La2 and Lb2 as reactive moieties as outlined below. La2 and Lb2 are defined as any moieties that can react by e.g. a nucleophilic substitution, addition to multiple bonds or cyclisation reaction to form a given L2 linker as exemplified below.

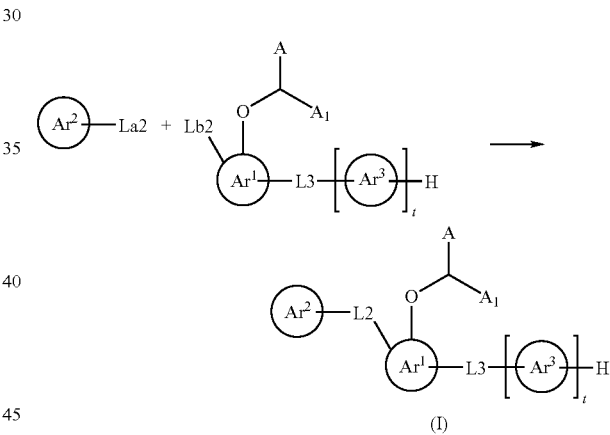

For example, the linker -L2- being -Alk$^1$-Z-(Alk$^2$)$_p$- can be formed by reacting Ar$^2$-Alk$^1$-"leaving group" with a nucleophilic derivative H—Z-(Alk$^2$)$_p$-Ar$^1$(L1A)L3Ar$^3$H wherein Z could be O, S or NR and Alk$^1$ could be an alkyl group. The reactions can also be made by reversing the functionalisation of La2 and Lb2 to make the connection between Z and Alk$^2$. The linkers wherein Z is SO or SO$_2$ can be obtained by oxidations of the corresponding -(Alk$^1$)$_m$-S-(Alk$^2$)$_p$-derivatives during appropriate conditions.

Further representative examples, -L2- being -Alk$^1$-Z-(Alk$^2$)$_p$— wherein Z is NH(CO) or NHSO$_2$ can be formed by reacting Ar$^2$-(Alk$^1$)-NH$_2$ with an acylating derivative "leaving group"-CO-(Alk$^2$)$_p$-Ar$^1$(L1A)L3Ar$^3$H or "leaving group"-SO$_2$-(Alk$^2$)$_p$-Ar$^1$(L1A)L3Ar$^3$H, respectively. Alternatively, the conversion can be made directly with the acids HO—CO-(Alk$^2$)$_p$-Ar$^1$(L1A)L3Ar$^3$H and HO—SO$_2$-(Alk$^2$)$_p$-Ar$^1$(L1A)L3Ar$^3$H, respectively, using suitable coupling reagents such as dicyclohexylcarbodiimide (DCC), and promoters such as 1-hydroxybenzotriazole. Analogously, -L2- being -Alk$^1$-Z-(Alk$^2$)$_p$- wherein Z being NH(CO)NH can be formed by reacting Ar²-(Alk¹)-NH₂ with an isocyanate derivative OCN-(Alk²)$_p$-Ar¹(L1A)L3Ar³H using suitable acid or base catalysis. The reactions can also be made by reversing the functionalisation of La2 and Lb2 to provide the "retro-bonds" in the case of NH(CO) or NHSO₂. Analogously, the connections can be made between Z and Alk².

A metal catalyzed coupling reaction like the Stille coupling reaction, the Suzuki coupling reaction, the Heck reaction and the Sonogashira reaction are useful in the synthesis of examples with L2 being an divalent alkylene radical, a divalent alkenylene radical or a divalent alkynylene radical.

Compounds with L2 being a hydrazone are usually conveniently formed by a condensation reaction between the corresponding hydrazines and aldehydes in ethanol or without solvent.

Likewise, L2 being -(Alk¹)$_m$-Z-(Alk²)$_p$- wherein Z is a 5-membered heterocyclic system exemplified by, for example,

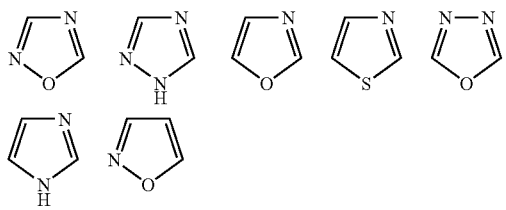

can be made according to standard cyclisation procedures using appropriate solvents, catalysts and temperatures. For example, formation of 1,2,4-triazole can be made with La2 being acylhydrazide and Lb2 being amide or thioamide or the reverse orientation of La2 and Lb2. 1,2,4-Oxadiazole can be formed from La2 being amidoxime and Lb2 being carboxylic ester or the reverse orientation of La2 and Lb2. 1,3,4-Oxadiazole can be formed from La2 being acylhydrazide and Lb2 being carboxylic ester or the reverse orientation of La2 and Lb2. The thiazole can be made from La2 being thioamide and Lb2 being an α-haloketone or the reverse orientation of La2 and Lb2. The isoxazole can be made from La2 being alkyne and Lb2 being nitriloxide or the reverse orientation in a cylcoaddition reaction.

In an analogous manner the compounds of formula I can be made by forming the linker L3, according to procedures outlined for L2, as depicted below. Thus, La and Lb are defined as any moieties that can react by e.g. a nucleophilic substitution, addition to multiple bonds or cyclisation reaction to form a given linker as exemplified below.

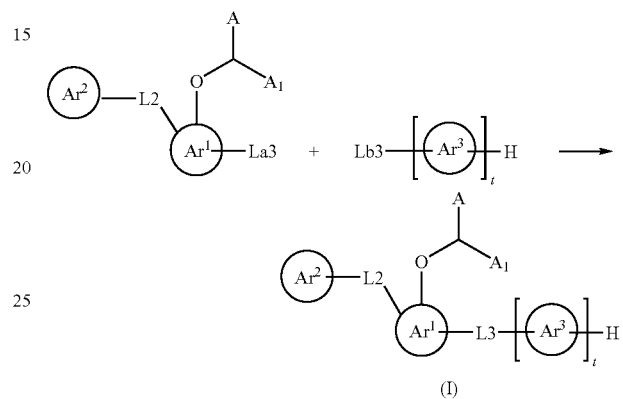

The Ar¹ moiety can also be the central scaffold that is used in connecting the L2 and L3 parts in a stepwise fashion. This can be done via aromatic substitutions of the Ar¹ core to attach L2 and/or L3, which then can be further functionalised to give the final Formula I compounds.

Furthermore, the Ar¹ moiety can also be assembled via ring cyclisation reactions with reactants containing the L2 and L3 units either containing the full appendices as outlined below:

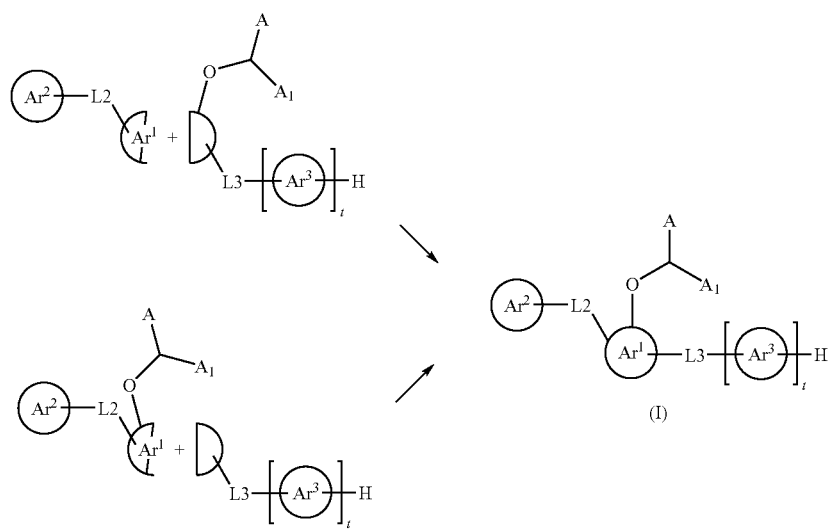

or in forms that can be further functionalised into the final Formula I structures as described previously. One such illustration is given below

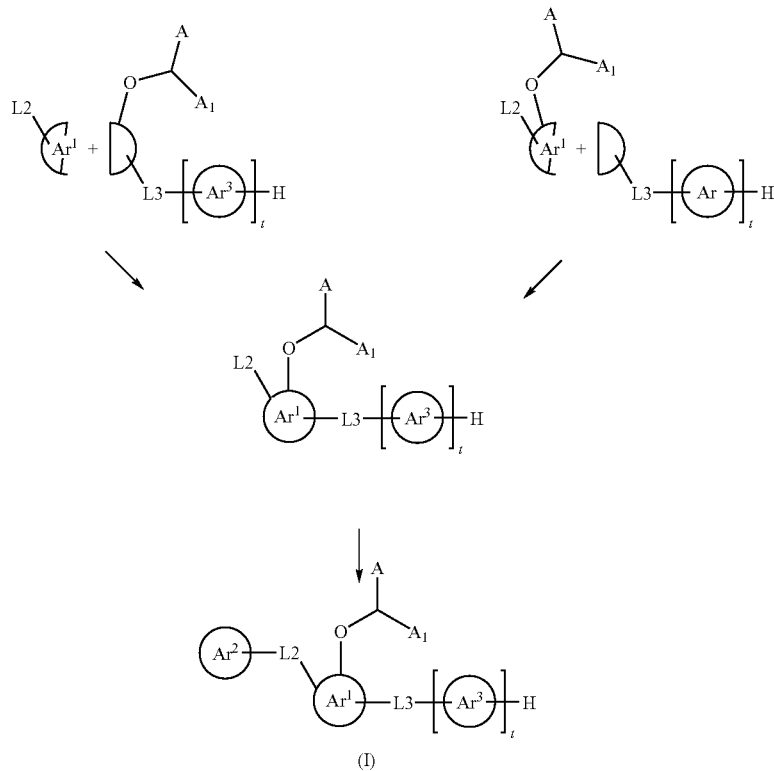

For example, 1,2,4-triazoles can be made from acylhydrazides and amides or thioamides; 1,2,4-Oxadiazoles from amidoximes and carboxylic esters; 1,3,4-Oxadiazoles from acylhydrazides and carboxylic esters; Thiazoles from thioamides and α-haloketones; Pyridines via various cycloaddition reactions.

The building blocks used in the reactions are either commercially available or made according to standard procedures well-know to one skilled in the art as described in "*Advanced organic chemistry*", 4$^{th}$ Edition (Wiley), J March, "*Comprehensive Organic Transformation*", 2$^{nd}$ Edition (Wiley), R. C. Larock, "*Handbook of Heterocyclic Chemistry*", 2$^{nd}$ Edition (Pergamon), A. R. Katritzky or other suitable literature sources. The Examples herein describe specific strategies for the synthesis of compounds wherein Ar$^1$ is phenyl. Analogous compounds are accessible by variation of the intermediates used in the Examples.

The following Examples illustrate the preparation of compounds with which this invention is concerned. Some compounds were synthesised, and some were acquired from commercial sources. In the Examples:

General Comments:

Microwave chemistry was performed in a Personal Chemistry Emrys Optimizer. NMR spectra were obtained on a Bruker Avance AMX 300 MHz instrument. LC/MS was performed on an Agilent 1100-series instrument. LC/MS methods are as follows:

An10p8: Column: XTerra MS C18; Flow: 1.0 mL/min; Gradient: 0-5 min: 15-100% MeCN in water, 5-7½ min: 100% MeCN; Modifier: 5 mM ammonium formate; MS-ionisation mode: API-ES (pos.). An10n8: Column: XTerra MS C18; Flow: 1.0 mL/min; Gradient: 0-5 min: 15-100% MeCN in water, 5-7½ min: 100% MeCN; Modifier: 5 mM ammonium formate; MS-ionisation mode: API-ES (neg.).

General synthetic route I

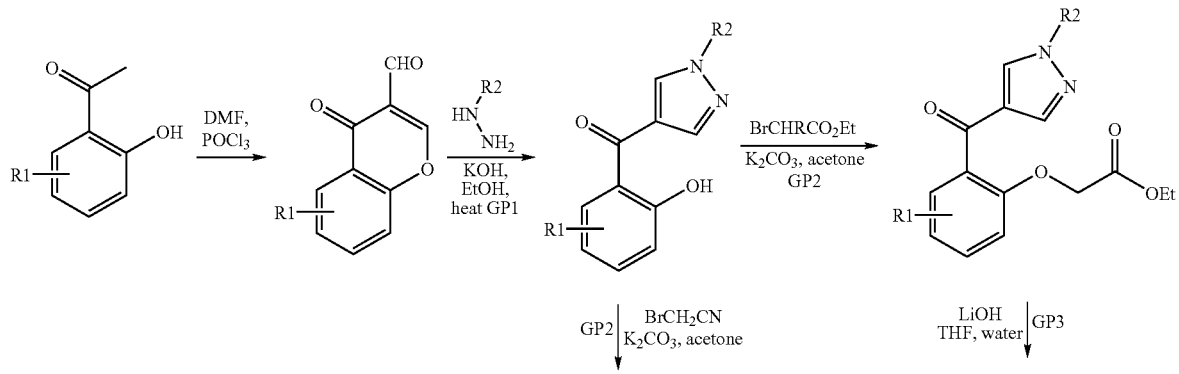

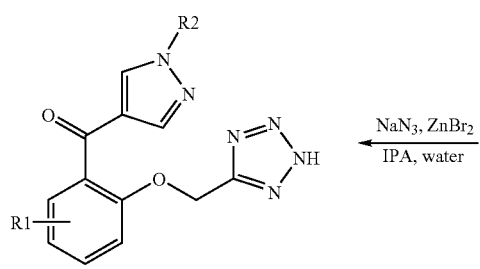 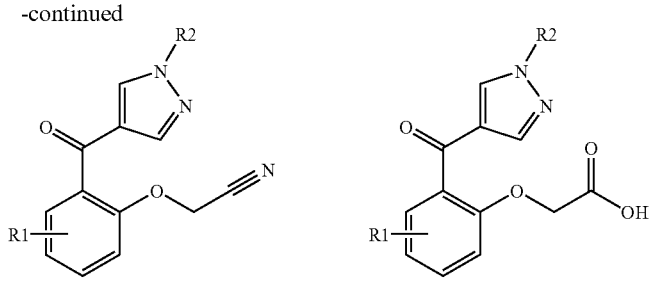

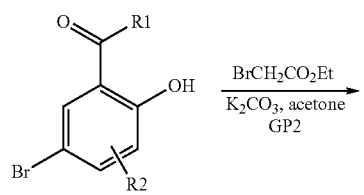

General synthetic route II

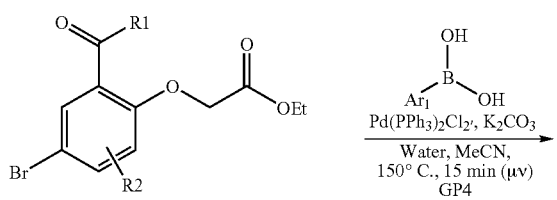

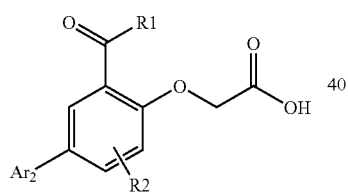

General Procedure 1 (GP1):
Condensation of 3-formylchromone with Arylhydrazine

The 3-formylchromone (1.0 mmol) and the arylhydrazine (1.0 mmol) in ethanol (3.0 mL) in a reaction tube was added 4.0 M aq. KOH (1.0 mL, 4.0 mmol). The tube was sealed and heated by microwaves to 120° C. for 7 min (420 s). The reaction mixture was added 3% HCl until pH<1 and left to precipitated. The precipitate was filtered off and washed with a small amount of ethanol. The product was used directly or purified by recrystallisation from ethanol or by flash chromatography.

General Procedure 2 (GP2):
Alkylation of Phenol

The phenol (0.5 mmol) in acetone (1 mL) was added ethyl bromoacetate (85 mg, 0.5 mmol) or ethyl 2-bromopropionate (91 mg, 0.5 mmol) and $K_2CO_3$ (75 mg, 0.54 mmol), and the reaction mixture was stirred at room temperature for 12 h. The reaction mixture was then concentrated in vacuo and the residue was partitioned between water and ethyl acetate. The organic phase was washed with brine, dried ($MgSO_4$) and concentrated. The product was used directly or purified by recrystallization from MeOH or by flash chromatography.

General Procedure 3 (GP3):
Hydrolysis of Ester

The ester (0.10 mmol) in THF (0.5 mL) was added $LiOH.H_2O$ (6.3 mg, 0.15 mmol) in water (0.5 mL). The reaction was stirred at room temperature for >2 h, 3% HCl was added until pH<1, and the mixture was extracted with $CH_2Cl_2$. The organic phase was dried ($MgSO_4$) and concentrated to give the product.

General Procedure 4 (GP4):
Suzuki Coupling/Ester Hydrolysis

Aryl bromide (0.20 mmol), aryl boronic acid (0.21 mmol) and $Pd(PPh_3)_2Cl_2$ (9 mg, 0.01 mmol) was added MeCN (0.4 mL, degassed) and 1.0 M $Na_2CO_3$ (0.4 mL, degassed). The reaction mixture was degassed by letting argon through for ½ min and heated by microwaves (150° C., 300 s), then added 3% HCl until pH<1 and extracted with $CH_2Cl_2$. The extract was filtered through celite and concentrated, and the residue was purified by solid-phase extraction (pre-packed 1 g SAX columns), or by flash chromatography.

Intermediate-1

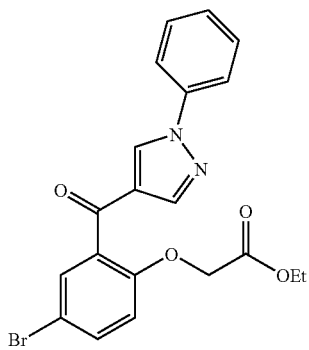

Ethyl 4-bromo-2-(1-phenyl-1H-pyrazole-4-carbonyl)phenoxyacetate. Prepared from (5-bromo-2-hydroxy-phenyl)-(1-phenyl-1H-pyrazol-4-yl)ketone and ethyl bromoacetate according to GP2 to give 215 mg (100%) white crystals. The product was used without further purification: LC/MS (an 10p8): Rt 6.15 min, m/z 429 $[M+H]^+$; $^1H$ NMR ($CDCl_3$): δ 1.26 (t, J=7.1 Hz, 3H), 4.24 (q, J=7.1 Hz, 2H), 4.64 (s, 2H), 6.72 (d, J=8.9 Hz, 1H), 7.34 (m, 1H), 7.46 (m, 2H), 7.53 (dd, J=8.9, 2.5 Hz, 1H), 7.59 (d, J=2.5 Hz, 1H), 7.73-7.78 (m, 2H), 8.17 (s, 1H), 8.58 (s, 1H); $^{13}C$ NMR ($CDCl_3$): δ14.3, 61.9, 65.5, 114.0, 114.5, 119.8, 125.3, 127.7, 129.8, 131.8, 132.3, 132.7, 134.6, 139.6, 142.7, 154.1, 168.5, 186.9.

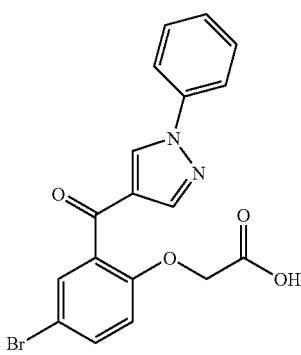

D1

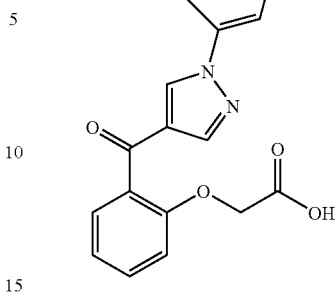

D2

4-Bromo-2-(1-phenyl-1H-pyrazole-4-carbonyl)phenoxyacetic acid. Prepared from ethyl 4-bromo-2-(1-phenyl-1H-pyrazole-4-carbonyl)phenoxyacetate (31 mg, 0.072 mmol) according to GP3 to give 28.4 mg (99%) white solid: LC/MS (an10p8): Rt 3.14 min, m/z 401; $^1$H NMR (CDCl$_3$): δ 3.51 (s, 1H), 4.80 (s, 1H), 6.97 (d, J=8.7 Hz, 1H), 7.38-7.44 (m, 1H), 7.49-7.55 (m, 2H), 7.64-7.69 (m, 1H), 7.72-7.77 (m, 3H), 8.19 (s, 1H), 8.52 (s, 1H); $^{13}$C NMR (CDCl$_3$): δ67.2, 115.1, 116.6, 120.1, 124.5, 128.4, 130.0, 131.9, 133.3, 136.2, 139.2, 143.3, 155.2, 169.9, 187.6.

2-(1-Phenyl-1H-pyrazole-4-carbonyl)phenoxyacetic acid. Prepared from ethyl 2-(1-phenyl-1H-pyrazole-4-carbonyl)phenoxyacetate according to GP3 and purified by column chromatography (SiO$_2$, EtOAc:heptane, 1:1) to give 15 mg (56%) of the title compound as white solid: LC/MS (an10n8): Rt 2.90 min, m/z 321.0 [M−H]$^-$; $^1$H NMR (CDCl$_3$): δ4.83 (s, 2H), 7.10 (d, J=8.3 Hz, 1H), 7.20 (t, J=7.5 Hz, 1H), 7.35-7.42 (m, 1H), 7.46-7.53 (m, 2H), 7.54-7.61 (m, 1H), 7.66 (dd, J=7.5, 1.5 Hz, 1H), 7.70-7.75 (m, 2H); $^{13}$C NMR (CDCl$_3$): δ 67.7, 115.5, 120.1, 122.8, 124.7, 128.3, 128.6, 129.9, 131.0, 131.9, 134.0, 139.3, 143.5, 156.6, 170.4, 189.3.

Intermediate-2

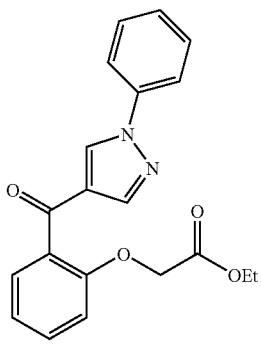

Intermediate-3

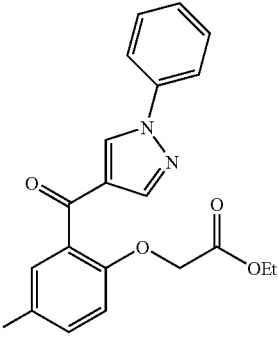

Ethyl 2-(1-phenyl-1H-pyrazole-4-carbonyl)phenoxyacetate. Prepared from (2-hydroxyphenyl)-(1-phenyl-1H-pyrazol-4-yl)ketone (264 mg, 1.0 mmol) and ethyl bromoacetate according to GP2 to give 235 mg (67%) of the title compound as white solid: $^1$H NMR (CDCl$_3$): δ 1.26 (t, J=7.1 Hz, 3H), 4.24 (q, J=7.1 Hz, 2H), 4.67 (s, 2H), 6.84 (d, J=8.3 Hz, 1H), 7.10 (ts, J=7.4, 0.8 Hz, 1 Hz), 7.29-7.36 (m, 1H), 7.41-7.53 (m, 4H), 7.72-7.78 (m, 2H), 8.18 (s, 1H), 8.58 (s, 1H); $^{13}$C NMR (CDCl$_3$): δ 14.3, 61.7, 65.4, 112.9, 118.8, 119.3, 119.7, 120.0, 122.1, 125.8, 127.6, 129.7, 129.9, 130.1, 130.6, 131.8, 132.1, 136.3, 139.7, 142.8, 155.0, 168.9, 188.7.

Ethyl 4-fluoro-2-(1-phenyl-1H-pyrazole-4-carbonyl)phenoxyacetate. Prepared from 4-fluoro-2-(1-phenyl-1H-pyrazole-4-carbonyl)phenol (282 mg) and ethyl bromoacetate according to GP2 to give 335 mg (91%) yellow solid: LC/MS (an10n8): Rt 3.16, m/z 339.0 [M−H]$^-$; $^1$H NMR (CDCl$_3$): δ 1.26 (t, J=7.0 Hz, 3H), 4.23 (t, J=7.1 Hz, 2H), 4.63 (s, 2H), 6.81 (dd, J=9.0, 4.0 Hz, 1H), 7.13 (ddd, J=8.9, 4.5, 3.0 Hz, 1H), 7.21 (dd, J=8.1, 3.2 Hz, 1H), 7.31-7.37 (m, 1H), 7.24-7.50 (m, 2H), 7.72-7.78 (m, 2H), 8.18 (s, 1H), 8.58 (s, 1H); $^{13}$C NMR (CDCl$_3$): δ14.3, 61.8, 66.1, 114.0 (d, J$_{CF}$=7.6 Hz), 116.8 (d, J$_{CF}$=24.5 Hz), 118.3 (d, J$_{CF}$=23.5 Hz), 119.7, 125.2, 127.7, 129.7, 131.8, 139.6, 142.8, 151.1 (d, J$_{CF}$=2.2 Hz), 157.6 (d, J$_{CF}$=241.1 Hz), 168.7, 187.1.

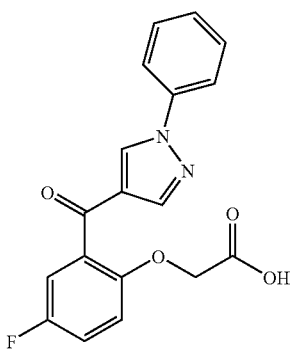

D3

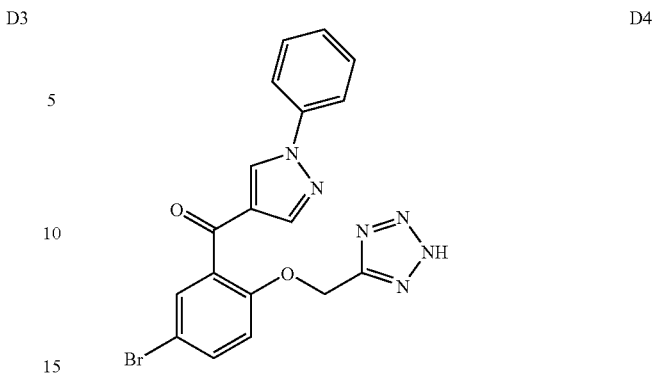

D4

4-Fluoro-2-(1-phenyl-1H-pyrazole-4-carbonyl)phenoxyacetic acid. Prepared from ethyl 4-fluoro-2-(1-phenyl-1H-pyrazole-4-carbonyl)phenoxyacetate (31 mg) according to GP3 to give 30 mg (100%) of a pale yellow solid: LC/MS (an10n8): Rt 3.16, m/z 339.0 [M−H]$^-$; $^1$H NMR (CDCl$_3$): δ 4.60 (s, 2H), 6.90 (dd, J=9.2 Hz, 1H), 7.08-7.17 (m, 1H), 7.21 (dd, J=7.9, 3.0 Hz, 1H), 7.28-7.35 (m, 1H), 7.38-7.46 (m, 2H), 7.65 (d, J=7.5 Hz, 2H), 8.06 (s, 1H), 8.44 (s, 1H).

[5-Bromo-2-(2H-tetrazol-5-ylmethoxy)phenyl](1-phenyl-1H-pyrazol-4-yl)ketone. [4-Bromo-2-(1-phenyl-1H-pyrazole-4-carbonyl)phenoxy]-acetonitrile (38 mg) was added NaN3 (66 mg), ZnBr$_2$ (59 mg), isopropanol (1.3 mL) and water (1.6 mL), and the reaction mixture was heated to reflux for 1 h. The mixture was added 3% HCl (1 mL) and EtOAc (4 mL) and stirred until two clear phases appeared. The aqueous phase was added 3% HCl until pH<1 and extracted with EtOAc. The combined organic phases were washed with brine, dried (MgSO$_4$) and concentrated to give 47 mg white foam: LC/MS (an10n8): Rt 2.93, m/z 243.0 [M−H]$^-$; $^1$H NMR (CDCl$_3$): δ 5.69 (s, 2H), 7.13 (d, J=8.6 Hz, 1H), 7.39-7.45 (m, 1H), 7.49-7.56 (m, 2H), 7.62-7.71 (m, 2H), 7.71-7.79 (m, 1H), 8.13 (s, 1H), 8.45 (s, 1H); $^{13}$C NMR (CDCl$_3$): δ 63.3, 115.6, 117.7, 120.3, 124.5, 128.6, 130.0, 131.2, 132.0, 132.9, 136.3, 139.1, 143.5, 154.7, 188.4.

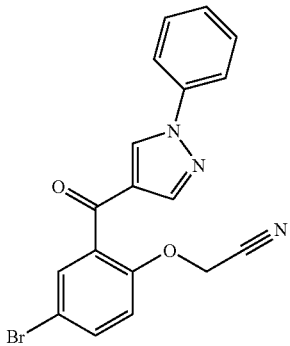

Intermediate-4

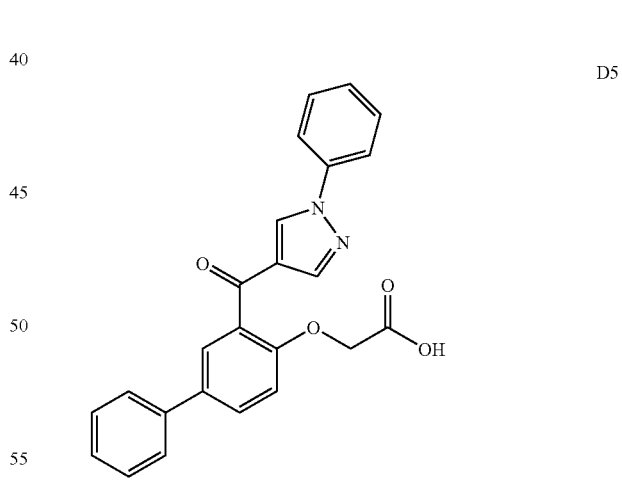

D5

4-Bromo-2-(1-phenyl-1H-pyrazole-4-carbonyl)phenoxyacetonitrile. (5-Bromo-2-hydroxy-phenyl)-(1-phenyl-1H-pyrazol-4-yl)ketone (342 mg) was added bromoacetonitrile (122 mg), acetone (2 mL) and K$_2$CO$_3$ (140 mg), and the reaction was stirred for 24 h. The reaction mixture was concentrated and the residue was partitioned between water and EtOAc. The organic phase was washed with brine, dried (MgSO4) and concentrated to give 383 mg (100%) yellow solid, that was used directly in the next step: LC/MS (an10p8): Rt 4.39 min, m/z 381.5 [M+1]$^+$; $^1$H NMR (CDCl$_3$): δ 4.80 (s, 2H), 7.07 (d, J=8.7 Hz, 1H), 7.35-7.42 (m, 1H), 7.45-7.54 (m, 2H), 7.60-7.69 (m, 2H), 7.69-7.75 (m, 2H), 8.03 (s, 1H), 8.31 (s, 1H); $^{13}$C NMR (CDCl$_3$): δ 55.2, 114.7, 116.6, 116.7, 120.1, 125.1, 128.2, 129.9, 131.0, 132.6, 133.2, 135.0, 139.3, 142.7, 153.0, 186.0.

3-(1-Phenyl-1H-pyrazole-4-carbonyl)biphenyl-4-yloxyacetic acid. Prepared from ethyl [4-bromo-2-(1-phenyl-1H-pyrazole-4-carbonyl)phenoxy]acetate and phenylboronic acid according to GP4: LC/MS (an 10p8): Rt 1.05 min, m/z 398.6 [M−H]$^-$; $^1$H NMR (CDCl$_3$): δ 4.86 (s, 2H), 7.17 (d, J=8.6 Hz, 1H), 7.35-7.57 (m, 8H), 7.70-7.75 (m, 2H), 7.78 (dd, J=8.6, 2.3 Hz, 1H), 7.84 (d, J=2.3 Hz, 1H), 8.20 (s, 1H), 8.54 (s, 1H); $^{13}$C NMR (CDCl$_3$): δ 67.7, 115.8, 120.1, 124.8, 127.1, 128.0, 128.3, 129.1, 129.3, 129.4, 129.9, 132.3, 136.2, 139.3, 139.3, 143.5, 155.8, 170.4, 189.3.

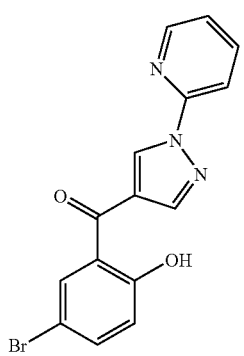

Intermediate-5

(5-Bromo-2-hydroxyphenyl)-(1-pyridin-2-yl-1H-pyrazol-4-yl)ketone. To a suspension of 6-bromo-3-formylchromone (253 mg) in isopropanol (3 mL) and $CH_2Cl_2$ (2 mL) was added 2-hydrazinopyridine (109 mg), and the mixture was stirred for 15 min to form a yellow slurry. The slurry was added KOH (0.25 g) in water (0.25 mL), and the reaction was heated to reflux for 1 h. The reaction mixture was diluted with water, added 3% HCl until pH<1 and extracted with $CH_2Cl_2$ (2×). The extract was washed with water and brine, dried ($MgSO_4$) and concentrated to give 342 mg orange foam, which was purified by flash chromatography ($SiO_2$, EA:Hep, 1:1) to give 53 mg (15%) yellow solid: LC/MS (an10p8): Rt 5.0 min, m/z 343.5 $[M+H]^+$; $^1H$ NMR ($CDCl_3$): δ 6.98 (d, J=8.9 Hz, 1H), 7.31 (ddd, J=7.3, 4.9, 0.9 Hz, 1H), 7.60 (dd, J=8.9, 2.5 Hz, 1H), 7.87-7.93 (m, 1H), 8.03 (d, J=2.4 Hz, 1H), 8.04-8.09 (m, 1H), 8.02 (s, 1H), 8.47-8.51 (m, 1H), 9.13 (s, 1H), 11.94 (s, 1H); $^{13}C$ NMR ($CDCl_3$): δ 110.9, 113.3, 120.8, 121.6, 122.8, 123.1, 130.5, 133.5, 138.9, 139.3, 143.3, 148.7, 161.9, 191.4.

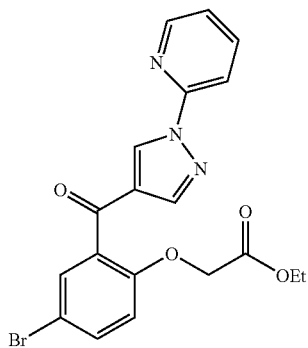

Intermediate-6

Ethyl 4-bromo-2-(1-pyridin-2-yl-1H-pyrazole-4-carbonyl)phenoxyacetate. Prepared from (5-bromo-2-hydroxyphenyl)-(1-pyridin-2-yl-1H-pyrazol-4-yl)ketone (43 mg) according to GP2 and purified by flash chromatography ($SiO_2$, EtOAc:heptane, 1:2) to give 34 mg (63%) of a pale yellow solid: LC/MS (an 10p8): Rt 4.9 min, m/z 429.5 $[M+H]^+$; $^1H$ NMR ($CDCl_3$): δ 1.23 (t, J=7.2 Hz, 3H), 4.20 (q, J=7.2 Hz, 2H), 4.62 (s, 2H), 6.76 (d, J=8.6 Hz, 1H), 7.23-7.28 (m, 1H), 7.53 (ddd, J=8.9, 2.6, 1.0 Hz, 1H), 7.58 (d, J=2.5 Hz, 1H), 7.82-7.99 (m, 1H), 8.01 (d, J=8.1 Hz, 1H), 8.19 (s, 1H), 8.40-8.44 (m, 1H), 8.99 (s, 1H); $^{13}C$ NMR ($CDCl_3$): δ 14.3, 61.8, 66.1, 114.5, 114.7, 131.6, 132.3, 132.4, 134.6, 139.1, 148.5, 154.4, 168.3, 187.1.

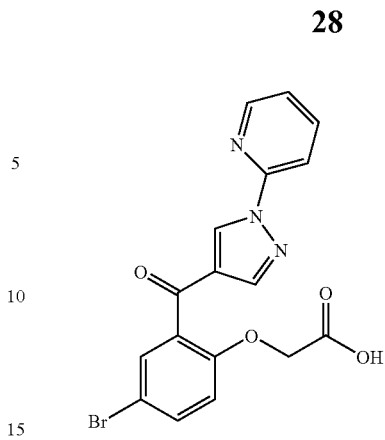

D6

4-Bromo-2-(1-pyridin-2-yl-1H-pyrazole-4-carbonyl)phenoxyacetic acid. Prepared from ethyl [4-bromo-2-(1-pyridin-2-yl-1H-pyrazole-4-carbonyl)phenoxy]-acetate (21 mg) according to GP3 to give 20 mg white foam: LC/MS (an10n8): Rt 2.8 min, m/z 401.9 $[M-H]^-$; $^1H$ NMR ($CDCl_3$): δ 4.79 (s, 2H), 6.98 (d, J=8.9 Hz, 1H), 7.28-7.34 (m, 1H), 7.67 (dd, J=8.9, 2.5 Hz, 1H), 7.75 (d, J=2.5 Hz, 1H), 7.86-7.94 (m, 1H), 8.02-8.08 (m, 1H), 8.22 (s, 1H), 8.43-8.48 (m, 1H), 9.04 (s, 1H).

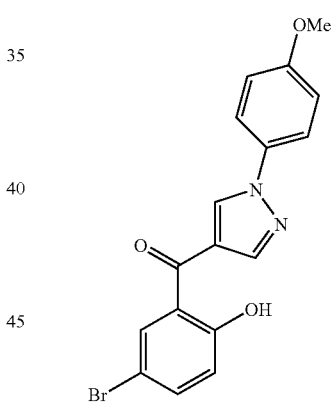

Intermediate-7

(5-Bromo-2-hydroxy-phenyl)-[1-(4-methoxyphenyl)-1H-pyrazol-4-yl]ketone. To a suspension of 6-bromo-3-formylcromone (253 mg, 1.0 mmol) in ethanol (5 mL) was added 4-methoxyphenylhydrazine (175 mg, 1.0 mmol), and the mixture was stirred under argon for 12 h an orange slurry. The slurry was added KOH (260 mg) in water (0.25 mL), and the reaction was heated to reflux for 1½ h. The reaction mixture was added 3% HCl until pH<1 and left on ice to precipitate. The precipitate was filtered off and washed with a small amount of cold ethanol to give 256 mg (69%) beige solid that was used without further purification: LC/MS (an 10p8): Rt 5.0 min, m/z 372.5 $[M+H]^+$; $^1H$ NMR ($CDCl_3$): δ 3.88 (s, 3H), 6.98 (d, J=8.9 Hz, 1H), 7.03 (d, J=9.1 Hz, 2H), 7.59 (dd, J=9.0, 2.5 Hz, 1H), 7.66 (d, J=9.1 Hz, 2H), 8.02 (d, J=2.4 Hz, 1H), 8.15 s, 1H), 8.39 (s, 1H), 11.92 (s, 1H); $^{13}C$ NMR ($CDCl_3$): δ 55.9, 110.9, 115.0, 120.8, 121.6, 121.8, 122.9, 130.7, 133.5, 138.8, 142.3, 159.7, 161.8.

Intermediate-8

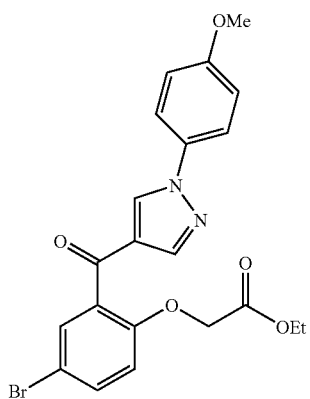

Ethyl 4-bromo-2-[1-(4-methoxyphenyl)-1H-pyrazole-4-carbonyl]phenoxyacetate. Prepared from (5-bromo-2-hydroxyphenyl)-[1-(4-methoxyphenyl)-1H-pyrazol-4-yl]ketone and ethyl bromoacetate according to GP2: LC/MS (an10p8): Rt 4.59 min, m/z 458.4/460.4 [M+H]+; $^1$H NMR (CDCl$_3$): δ 1.26 (t, J=7.1 Hz, 3H), 3.84 (s, 3H), 4.23 (q, J=7.1 Hz, 2H), 4.62 (s, 2H), 6.72 (d, J=8.9 Hz, 1H), 6.97 (d, J=8.7 Hz, 2H), 7.52 (dd, J=8.9, 2.6 Hz, 1H), 7.58 (d, J=2.5 Hz, 1H), 7.64 (d, J=8.9 Hz, 2H), 8.13 (s, 1H), 8.46 (s, 1H); $^{13}$C NMR (CDCl$_3$): δ14.3, 55.8, 61.9, 65.6, 114.1, 114.4, 114.8, 121.4, 125.0, 131.6, 132.4, 132.6, 133.2, 134.5, 142.5, 154.1, 159.2, 168.5, 186.9.

D8

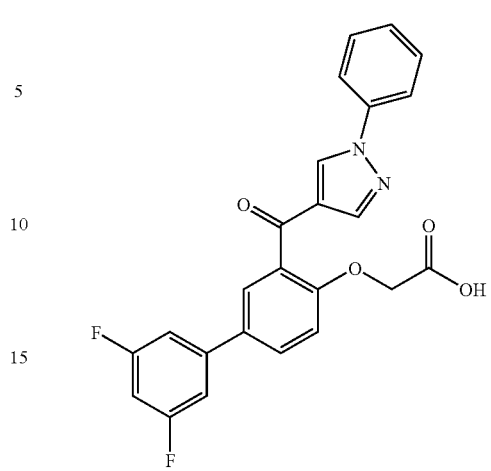

[3',5'-Difluoro-3-(1-phenyl-1H-pyrazole-4-carbonyl)biphenyl-4-yloxy]acetic acid. Prepared ethyl [4-bromo-2-(1-phenyl-1H-pyrazole-4-carbonyl)phenoxy]acetate and 3,5-difluorophenylboronic acid according to GP4: LC/MS (an10n8): Rt 3.03 min, m/z 434.5 [M+H]+; $^1$H NMR (CDCl$_3$): δ 4.85 (s, 2H), 6.81 (td, J=8.9, 2.3 Hz, 1H), 7.07 (d, J=8.3 Hz, 2H), 7.14 (d, J=8.9 Hz, 1H), 7.41 (d, J=6.6 Hz, 1H), 7.48 (s, 1H), 7.52 (d, J=8.5 Hz, 1H), 7.66-7.78 (m, 4H), 8.23 (s, 1H), 8.57 (s, 1H)

D7

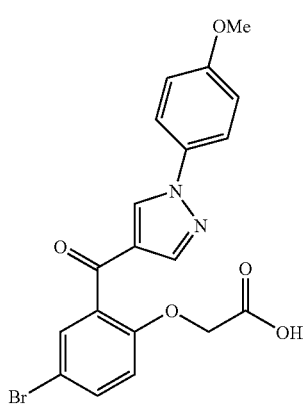

4-Bromo-2-[1-(4-methoxyphenyl)-1H-pyrazole-4-carbonyl]phenoxyacetic acid. Prepared from ethyl 4-bromo-2-[1-(4-methoxy-phenyl)-1H-pyrazole-4-carbonyl]phenoxyacetate (23 mg) according to GP3 to give 21 mg (97%) white foam: LC/MS (an10n8): Rt 5.76 min, m/z 428.9 [M−H]−; $^1$H NMR (CDCl$_3$): δ 3.86 (s, 3H), 4.77 (s, 2H), 6.94 (d, J=8.9 Hz, 1H), 6.99 (d, J=9.2 Hz, 2H), 7.59-7.66 (m, 3H), 7.71 (d, J=2.4 Hz, 1H), 8.14 (d, J=0.6 Hz, 1H), 8.40 (d, J=0.6 Hz, 1H) $^{13}$C NMR (CDCl$_3$): δ 55.9, 67.2, 115.0, 115.1, 116.6, 121.8, 124.2, 130.7, 131.8, 132.7, 133.2, 136.1, 143.2, 155.2, 159.7, 169.9, 187.6.

D9

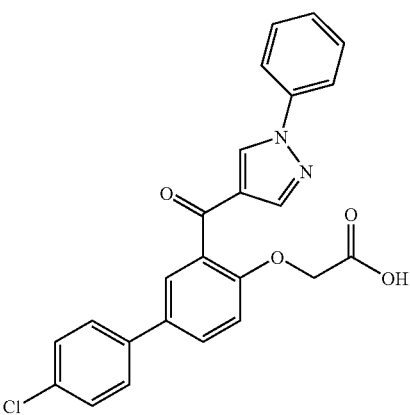

[4'-Chloro-3-(1-phenyl-1H-pyrazole-4-carbonyl)biphenyl-4-yloxy]acetic acid. Prepared from ethyl [4-bromo-2-(1-phenyl-1H-pyrazole-4-carbonyl)phenoxy]acetate and 4-chlorophenylboronic acid according to GP4: LC/MS (an10n8): Rt 3.08 min, m/z 432.5 [M−H]−.

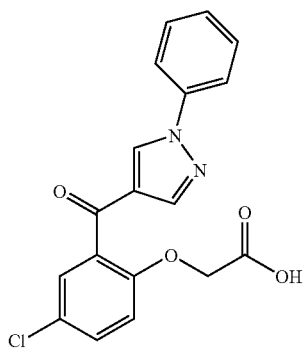

D10

[4-Chloro-2-(1-phenyl-1H-pyrazole-4-carbonyl)phenoxy]acetic acid. Prepared from (2-hydroxy-5-chlorophenyl)-(1-phenyl-1H-pyrazol-4-yl)-methanone and ethyl bromoacetate according to GP2 and GP3: LC/MS (an10p8): Rt 3.08 min, m/z 356.6 [M+1]$^+$; $^1$H NMR (CDCl$_3$): δ 4.75 (s, 2H), 6.95 (d, J=8.9 Hz, 1H), 7.33-7.41 (m, 1H), 7.44-7.52 (m, 3H), 7.55 (d, J=2.6 Hz, 1H), 7.69-7.75 (m, 2H), 8.18 (s, 1H), 8.52 (s, 1H).

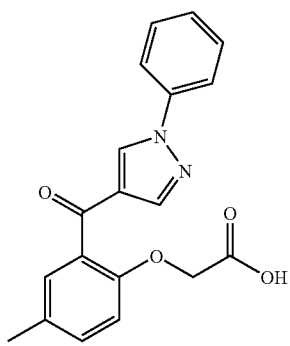

D11

[4-Methyl-2-(1-phenyl-1H-pyrazole-4-carbonyl)phenoxy]acetic acid. Prepared from (2-hydroxy-5-methylphenyl)-(1-phenyl-1H-pyrazol-4-yl)-methanone and ethyl bromoacetate according to GP2 and GP3: LC/MS (an 10p8): Rt 3.08 min, m/z 356.6 [M+1]$^+$; $^1$H NMR (CDCl$_3$): δ2.37 (s, 3H), 4.78 (s, 2H), 6.97 (d, J=9.0 Hz, 1H), 7.33-7.51 (m, 5H), 7.73 (d, J=6 Hz, 2H), 8.16 (s, 1H), 8.51 (s, 1H), 11.21 (br s, 1H)

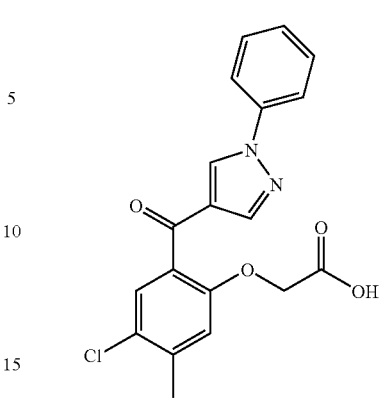

D12

[4-Chloro-3-methyl-2-(1-phenyl-1H-pyrazole-4-carbonyl)phenoxy]acetic acid. Prepared from (3-chloro-6-hydroxy-2-methyl-phenyl)-(1-phenyl-1H-pyrazol-4-yl)methanone and ethyl bromoacetate according to GP2 and GP3: LC/MS (an10p8): Rt 3.34 min, m/z 370.6 [M+1]$^+$; $^1$H NMR (CDCl$_3$): δ 2.44 (s, 3H), 4.77 (s, 2H), 6.92 (s, 1H), 7.39 (d, J=9.0 Hz, 1H), 7.46-7.51 (m, 2H), 7.59 (s, 1H), 7.72 (d, J=9.0 Hz, 2H), 8.19 (s, 1H), 8.52 (s, 1H), 10.39 (br s, 1H)

D13

[2,4-Dichloro-6-(1-phenyl-1H-pyrazole-4-carbonyl)phenoxy]acetic acid. Prepared from (3,5-dichloro-2-hydroxyphenyl)-(1-phenyl-1H-pyrazol-4-yl)methanone and ethyl bromoacetate according to GP2 and GP3: LC/MS (an10p8): Rt 3.27 min, m/z 390.5 [M+1]$^+$; $^1$H NMR (CDCl$_3$): δ 4.72 (s, 2H), 7.38-7.51 (m, 4H), 7.57-7.58 (m, 1H), 7.70 (d, J=8.1 Hz, 2H), 8.06 (s, 1H), 8.36 (s, 1H), 9.23 (br s, 1H).

D14

4-Bromo-2-[1-(2-chloro-phenyl)-1H-pyrazole-4-carbonyl]phenoxyacetic acid. Prepared from 6-bromo-3-formylchromone, 2-chlorophenylhydrazine and ethyl bromoacetate according to GP1, GP2 and GP3: LC/MS (an10p8) Rt 3.02 min, m/z 436.4 [M+H]+; ¹H NMR (CDCl₃): δ 4.76 (s, 2H), 6.94 (d, J=8.9 Hz, 1H), 7.39-7.47 (m, 2H), 7.53-7.67 (m, 3H), 7.74 (dd, J=2.4, 0.9 Hz, 1H), 8.21 (s, 1H), 8.40 (s, 1H); ¹³C NMR (CDCl₃): δ 67.2, 115.0, 116.7, 123.9, 127.9, 128.2, 128.7, 130.55, 130.59, 131.1, 133.3, 136.2, 136.6, 137.1, 143.1, 155.2, 170.0, 187.5.

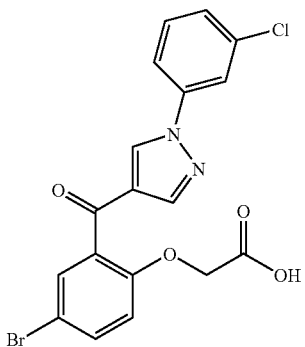

D15

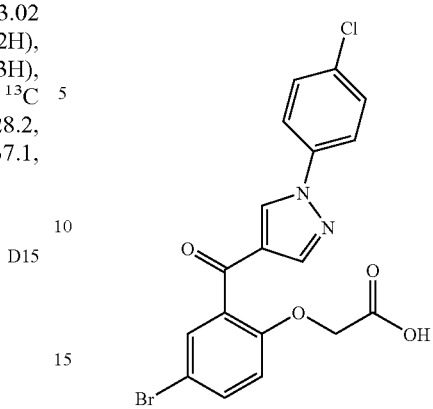

D17

4-Bromo-2-[1-(3-chloro-phenyl)-1H-pyrazole-4-carbonyl]phenoxyacetic acid. Prepared from 6-bromo-3-formylchromone and 3-chlorophenylhydrazine according to: LC/MS (an10p8) Rt 3.57 min, m/z 436.4 [M+H]+; ¹H NMR (CDCl₃): δ 4.76 (s, 2H), 6.90 (d, J=8.9 Hz, 1H), 7.34 (dm, J=6.8 Hz, 1H), 7.41 (t, J=8.3 Hz, 1H), 7.58-7.66 (m, 2H), 7.68 (d, J=2.0 Hz, 1H), 7.78 (m, 1H), 8.17 (s, 1H), 8.51 (s, 1H); ¹³C NMR (CDCl₃): δ66.8, 115.1, 116.2, 117.9, 120.4, 124.9, 128.3, 130.7, 131.0, 132.0, 133.2, 135.8, 136.1, 140.2, 143.4, 155.0, 170.1, 187.4.

4-Bromo-2-[1-(4-chlorophenyl)-1H-pyrazole-4-carbonyl]phenoxyacetic acid. Prepared from 6-bromo-3-formylchromone, 4-chlorophenylhydrazine and ethyl bromoacetate according to GP1, GP2 and GP3: LC/MS (an10p8): Rt 3.53 min, m/z 436.4 [M+H]+; ¹H NMR (CDCl₃): δ 4.74 (s, 2H), 6.88 (d, J=8.9 Hz, 1H), 7.44 (d, J=8.5 Hz, 2H), 7.61 (dd, J=8.9, 2.4 Hz, 1H), 7.63-7.70 (m, 3H), 8.17 (s, 1H), 8.49 (s, 1H); ¹³C NMR (CDCl₃): δ 66.4, 114.9, 115.7, 121.2, 124.9, 130.0, 130.9, 131.9, 133.1, 133.9, 135.9, 137.7, 143.3, 154.7, 170.8, 187.4.

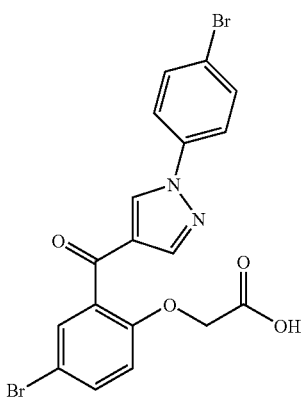

D16

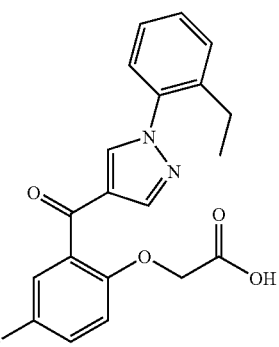

D18

4-Bromo-2-[1-(4-bromophenyl)-1H-pyrazole-4-carbonyl]phenoxyacetic acid. Prepared from 6-bromo-3-formylchromone, 4-bromophenylhydrazine and ethyl bromoacetate according to GP1, GP2 and GP3: LC/MS (an10p8) Rt 3.75 min, m/z 480.3 [M+H]+; ¹H NMR (CDCl₃): δ 4.75 (s, 2H), 6.89 (d, J=8.9 Hz, 1H), 7.59-7.65 (m, 5H), 7.66-7.69 (m, 1H), 8.16 (s, 1H), 8.50 (s, 1H); ¹³C NMR (CDCl₃): δ 66.5, 115.0, 115.9, 121.5, 121.8, 124.9, 130.8, 131.8, 133.0, 133.1, 135.9, 138.2, 143.4, 154.8, 170.6, 187.4.

4-Bromo-2-[1-(2-ethylphenyl)-1H-pyrazole-4-carbonyl] phenoxyacetic acid. Prepared from 6-bromo-3-formylchromone, 2-ethylphenylhydrazine and ethyl bromoacetate according to GP1, GP2 and GP3: LC/MS (an10n8): Rt 2.58 min, 427.0 m/z [M−H]+; ¹H NMR (CDCl₃): δ1.14 (t, J=7.5 Hz, 3H), 2.58 (q, J=7.5, 2H), 4.76 (s, 2H), 6.93 (d, J=8.9 Hz, 1H), 7.28-7.34 (m, 2H), 7.37-7.48 (m, 2H), 7.62 (dd, J=8.9, 2.6 Hz, 1H), 7.72 (d, J=2.5 Hz, 1H), 8.15 (s, 1H), 8.18 (s, 1H).

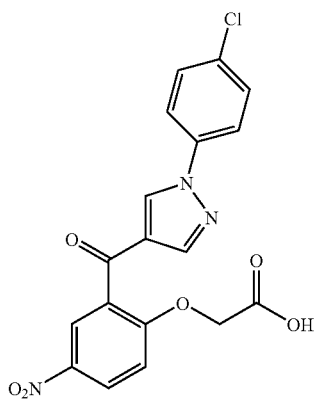

D19

4-Nitro-2-[1-(4-chlorophenyl)-1H-pyrazole-4-carbonyl]phenoxyacetic acid. Prepared from 6-nitro-3-formylchromone, 4-chlorophenylhydrazine and ethyl bromoacetate according to GP1, GP2 and GP3: LC/MS (an10p8): Rt 2.44 min, m/z 401.7 [M+H]$^+$; $^1$H NMR (CDCl$_3$): δ 4.84 (d, 2H), 7.1 (d, J=9.6 Hz, 1H), 7.44 (d, J=8.1 Hz, 2H), 7.67 (d, J=8.1 Hz, 2H), 8.22 (s, 1H), 8.36 (d, J=9.2 Hz, 1H), 8.41 (s, 1H), 8.53 (s, 1H); $^{13}$C NMR (CDCl$_3$): δ 65.6, 112.9, 121.3, 124.9, 126.2, 128.2, 130.0, 130.1, 131.9, 134.1, 137.6, 142.4, 143.3, 159.7, 169.9, 186.2.

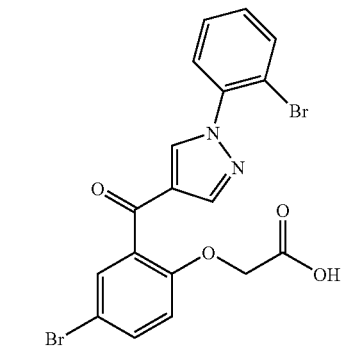

D21

4-Bromo-2-[1-(2-bromophenyl)-1H-pyrazole-4-carbonyl]phenoxyacetic acid. Prepared from 6-bromo-3-formylchromone, 2-bromophenylhydrazine and ethyl bromoacetate according to GP1, GP2 and GP3: LC/MS (an10p8): Rt 3.38 min, m/z 480.6 [M+H]$^+$; $^1$H NMR (CDCl$_3$): δ 4.75 (s, 2H), 6.91 (d, J=9.0 Hz, 1H), 7.34-7.64 (m, 6H), 7.73-7.74 (m, 2H), 8.22 (s, 1H), 8.36 (s, 1H).

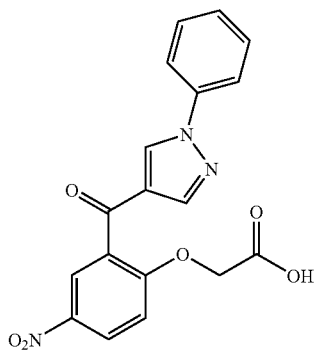

D20

4-Nitro-2-(1-phenyl-1H-pyrazole-4-carbonyl)phenoxyacetic acid. Prepared from 6-nitro-3-formylchromone, 2-ethylphenylhydrazine and ethyl bromoacetate according to GP1, GP2 and GP3: LC/MS (an10p8) Rt 2.05 min, m/z 367.8 [M+H]$^+$; $^1$H NMR (CDCl$_3$): δ 4.83 (s, 2H), 7.01 (d, J=9.0 Hz, 1H), 7.34-7.42 (m, 1H), 7.44-7.53 (m, 1H), 7.65-7.72 (m, 1H), 8.26 (s, 1H), 8.34 (dd, J=9.0, 2.6 Hz, 1H), 8.41 (d, J=2.6 Hz, 1H), 8.53 (s, 1H).

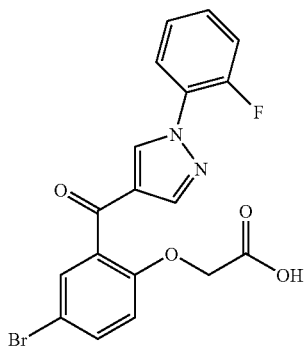

D22

4-Bromo-2-[1-(2-fluorophenyl)-1H-pyrazole-4-carbonyl]phenoxyacetic acid. Prepared from 6-bromo-3-formylchromone, 2-fluorophenylhydrazine and ethyl bromoacetate according to GP1, GP2 and GP3: LC/MS (an10p8): Rt 3.36 min, m/z 418.7 [M+H]$^+$; $^1$H NMR (CDCl$_3$): δ 4.75 (s, 2H), 6.91 (d, J=8.9 Hz, 1H), 7.21-7.42 (m, 3H), 7.62 (dd, J=8.9, 2.4 Hz, 1H), 7.70 (d, J=2.5 Hz, 1H), 7.85-7.92 (m, 1H), 8.20 (s, 1H), 8.51 (d, J=2.3 Hz, 1H); $^{13}$C NMR (CDCl$_3$): δ 66.9, 115.0, 116.3, 117.1, 117.4, 124.62, 124.63, 125.0, 125.39, 125.44, 127.4, 127.5, 129.6, 129.7, 130.8, 133.2, 135.8, 136.8, 143.0, 152.3, 155.0, 155.6, 170.5, 187.4.

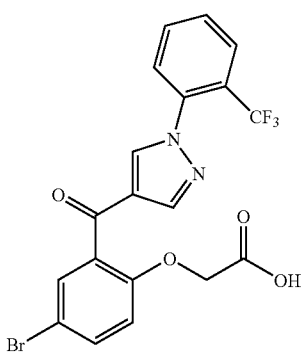

D23

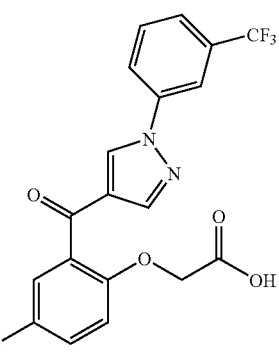

D25

4-Bromo-2-[1-(2-trifluoromethylphenyl)-1H-pyrazole-4-carbonyl]phenoxyacetic acid. Prepared from 6-bromo-3-formylchromone, 2-trifluoromethylphenylhydrazine and ethyl bromoacetate according to GP1, GP2 and GP3: LC/MS (an10p8): Rt 3.44 min, m/z 468.7 [M+H]$^+$; $^1$H NMR (CDCl$_3$): δ 4.72 (s, 2H), 6.89 (d, J=8.9 Hz, 1H), 7.53-7.75 (m, 5H), 7.84 (d, J=7.9 Hz, 1H), 8.20 (s, 2H); $^{13}$C NMR (CDCl$_3$): δ 66.8, 114.9, 116.2, 124.3, 126.3, 126.7, 127.58, 127.64, 129.2, 130.3, 130.7, 133.2, 136.0, 136.9, 143.1, 155.0, 170.3, 187.4.

4-Bromo-2-[1-(3-trifluoromethylphenyl)-1H-pyrazole-4-carbonyl]phenoxyacetic acid. Prepared from 6-bromo-3-formylchromone, 3-trifluoromethylphenylhydrazine and ethyl bromoacetate according to GP1, GP2 and GP3: LC/MS (an10p8): Rt 4.54 min, m/z 468.7 [M+H]$^+$; $^1$H NMR (CDCl$_3$): δ 4.76 (s, 2H), 6.89 (d, J=8.9 Hz, 1H), 7.57-7.66 (m, 3H), 7.68 (d, J=2.4 Hz, 1H), 7.89-7.96 (m, 1H), 8.04 (s, 1H), 8.20 (s, 1H), 8.59 (s, 1H), 9.15 (br s, 1H).

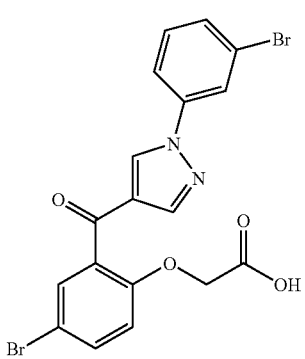

D24

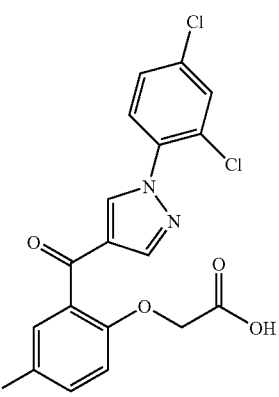

D26

4-Bromo-2-[1-(3-bromophenyl)-1H-pyrazole-4-carbonyl]phenoxyacetic acid. Prepared from 6-bromo-3-formylchromone, 3-bromophenylhydrazine and ethyl bromoacetate according to GP1, GP2 and GP3: LC/MS (an 10p8): Rt 4.29 min, m/z 480.5 [M+H]$^+$; $^1$H NMR (CDCl$_3$): δ 4.79 (s, 2H), 6.95 (d, J=9.0 Hz, 1H), 7.28-7.40 (m, 1H), 7.53 (d, J=9 Hz, 1H), 7.65-7.73 (m, 3H), 7.96 (s, 1H), 8.18 (s, 1H); 8.51 (s, 1H).

4-Bromo-2-[1-(2,4-dichlorophenyl)-1H-pyrazole-4-carbonyl]phenoxyacetic acid. Prepared from 6-bromo-3-formylchromone, 2,4-dichlorophenylhydrazine and ethyl bromoacetate according to GP1, GP2 and GP3: LC/MS (an 10p8): Rt 4.35 min, m/z 468.6 [M+H]$^+$; $^1$H NMR (DMSO-d$_6$): δ 4.76 (s, 2H), 7.03 (d, J=9.0 Hz, 1H), 7.52 (m, 1H), 7.57-7.69 (m, 3H), 7.89 (m, 1H), 8.19 (s, 1H), 8.69 (s, 1H); $^{13}$C NMR (DMSO-d$_6$): δ 55.8, 103.6, 106.2, 115.2, 119.5, 120.6, 120.7, 121.1, 122.4, 125.5, 125.6, 127.1, 128.3, 133.4, 145.1, 160.9, 177.4.

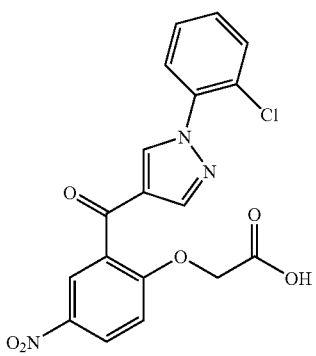

4-Nitro-2-[1-(2-chlorophenyl)-1H-pyrazole-4-carbonyl]phenoxyacetic acid. Prepared from 6-nitro-3-formylchromone 2-chlorophenylhydrazine and ethyl bromoacetate according to GP1, GP2 and GP3: LC/MS (an10p8): Rt 2.42 min, m/z 401.8 [M+H]$^+$; $^1$H NMR (CDCl$_3$): δ 4.83 (s, 2H), 7.01 (d, J=9.0 Hz, 2H), 7.42-7.48 (m, 2H), 7.56-7.63 (m, 2H), 8.34-8.40 (m, 2H), 8.5 (s, 2H).

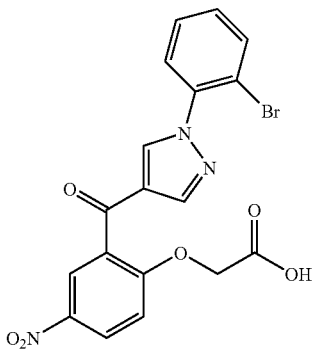

4-Nitro-2-[1-(2-bromophenyl)-1H-pyrazole-4-carbonyl]phenoxyacetic acid. Prepared from 6-nitro-3-formylchromone, 2-bromophenylhydrazine and ethyl bromoacetate according to GP1, GP2 and GP3: LC/MS (an10p8): Rt 2.33 min, m/z 445.9 [M−H]$^+$; $^1$H NMR (CDCl$_3$): δ 4.85 (s, 2H), 7.04 (d, J=9 Hz, 1H), 7.37-7.81 (m, 4H), 8.32-8.44 (m, 3H), 8.50 (s, 1H).

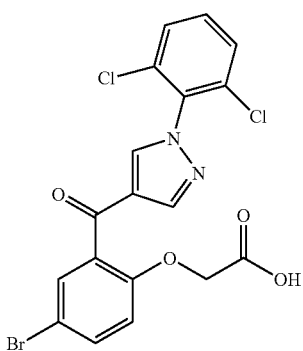

4-Bromo-2-[1-(2,6-dichlorophenyl)-1H-pyrazole-4-carbonyl]phenoxyacetic acid. Prepared from 6-bromo-3-formylchromone, 2,6-dichlorophenylhydrazine and ethyl bromoacetate according to GP1, GP2 and GP3: LC/MS (an10p8): Rt 2.56 min, m/z 468.6 [M+H]$^+$; $^1$H NMR (CDCl$_3$): δ 4.72, 6.88 (d, J=8.9 Hz, 1H), 7.37-7.44 (m, 1H), 7.45-7.52 (m, 2H), 7.59 (d, J=8.7 Hz, 1H), 7.70 (m, 1H), 8.14 (s, 1H), 8.26 (s, 1H).

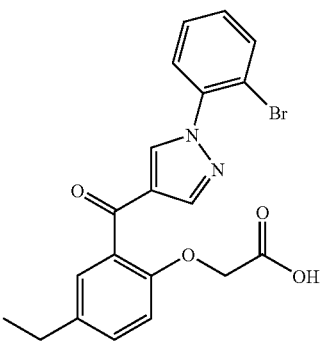

4-Ethyl-2-[1-(2-bromophenyl)-1H-pyrazole-4-carbonyl]phenoxyacetic acid. Prepared from 6-ethyl-3-formylchromone, 2-bromophenylhydrazine and ethyl bromoacetate according to GP1, GP2 and GP3: LC/MS (an10p8): Rt 2.88 min, m/z 428.8 [M+H]$^+$.

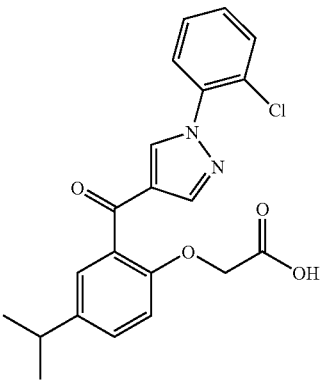

2-[1-(2-Chlorophenyl)-1H-pyrazole-4-carbonyl]-4-isopropylphenoxyacetic acid. Prepared from 6-isopropyl-3-formylchromone, 2-chlorophenylhydrazine and ethyl bromoacetate according to GP1, GP2 and GP3: LC/MS (an10p8): Rt 2.83 min, m/z 398.8 [M+H]$^+$; $^1$H NMR (CDCl$_3$): δ 1.28 (d, J=7.0 Hz, 6H), 2.93 (septet, J=6.9 Hz, 1H), 4.82 (s, 2H), 7.04 (d, J=8.5 Hz, 1H), 7.40-7.65 (m, 6H), 8.28 (s, 1H), 8.40 (s, 1H).

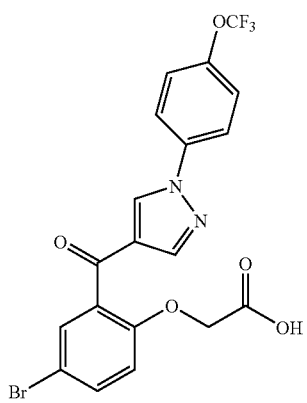

D32

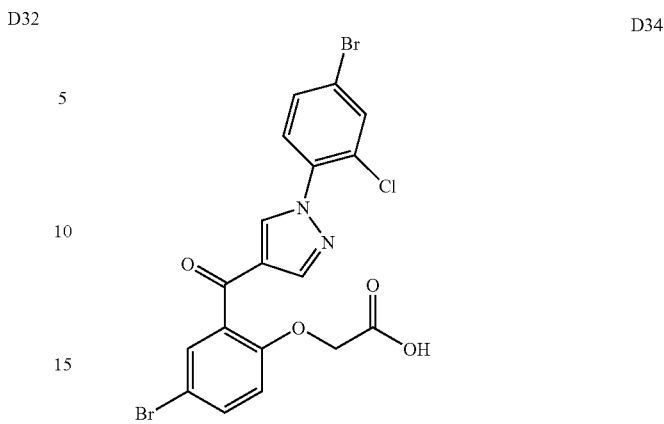

D34

{4-Bromo-2-[1-(4-trifluoromethoxyphenyl)-1H-pyrazole-4-carbonyl]phenoxy-acetic acid. Prepared from 6-bromo-3-formylchromone, 4-trifluoromethoxy-phenylhydrazine and ethyl bromoacetate according to GP1, GP2 and GP3: LC/MS (an10p8): Rt 3.24 min, m/z 484.6 [M+H]$^+$; $^1$H NMR (CDCl$_3$): δ 4.75 (s, 2H), 6.89 (d, J=8.9 Hz, 1H), 7.34 (d, J=9.0 Hz, 2H), 7.61 (dd, J=8.9, 2.6 Hz, 1H), 7.67 (m, 1H), 7.72-7.80 (m, 2H), 8.17 (s, 1H), 8.51 (s, 1H); $^{13}$C NMR (CDCl$_3$): δ 66.5, 115.0, 115.8, 121.4, 122.5, 125.0, 130.8, 132.0, 133.1, 136.0, 137.6, 143.4, 148.6, 148.7, 154.8, 170.8, 187.4.

4-Bromo-2-[1-(4-bromo-2-chlorophenyl)-1H-pyrazole-4-carbonyl]phenoxyacetic acid. Prepared from 6-bromo-3-formylchromone, 4-bromo-2-chlorophenylhydrazine and ethyl bromoacetate according to GP1, GP2 and GP3: LC/MS (an10p8): Rt 3.34 min, m/z 512.5 [M+H]$^+$; $^1$H NMR (CDCl$_3$): δ 4.78 (s, 2H), 6.95 (d, J=8.6 Hz, 1H), 7.51-7.76 (m, 5H), 8.21 (s, 1H), 8.42 (s, 1H).

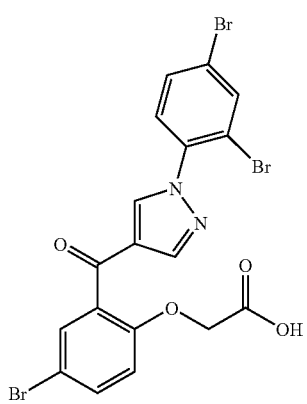

D33

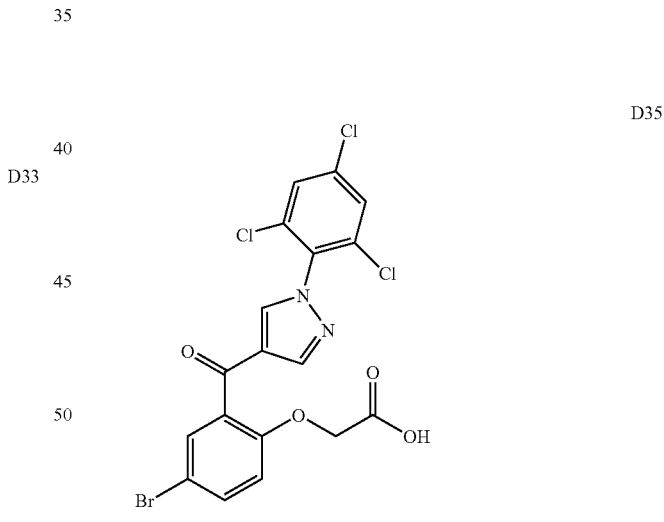

D35

4-Bromo-2-[1-(2,4-dibromophenyl)-1H-pyrazole-4-carbonyl]phenoxyacetic acid. Prepared from 6-bromo-3-formylchromone, 2,4-dibromophenylhydrazine according and ethyl bromoacetate to GP1, GP2 and GP3: LC/MS (an10p8): Rt 3.41 min, m/z 556.4 [M+H]$^+$; $^1$H NMR (CDCl$_3$): δ 4.75 (s, 2H), 6.92 (d, J=9.0 Hz, 1H), 7.45 (d, J=8.5 Hz, 1H), 7.63 (m, 2H), 7.73 (d, J=2.5 Hz, 1H), 7.92 (d, J=2.1 Hz, 1H), 8.22 (s, 1H), 8.37 (s, 1H).

4-Bromo-2-[1-(2,4,6-trichlorophenyl)-1H-pyrazole-4-carbonyl]phenoxyacetic acid. Prepared from 6-bromo-3-formylchromone, 2,4,6-trichlorophenylhydrazine and ethyl bromoacetate according to GP1, GP2 and GP3: LC/MS (an10p8): Rt 3.35 min, m/z 502.6 [M+H]$^+$; $^1$H NMR (CDCl$_3$): δ 4.91 (s, 2H), 7.05 (d, J=8.9 Hz, 1H), 7.68 (s, 2H), 7.78 (d, J=8.5 Hz, 1H), 7.88 (s, 1H), 8.31 (s, 1H), 8.43 (s, 1H), 9.03 (br s, 1H).

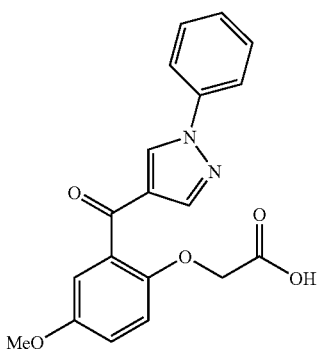

4-Methoxy-2-[1-phenyl-1H-pyrazole-4-carbonyl]phenoxyacetic acid. Prepared from 6-bromo-3-formylchromone, 2,4-dichlorophenylhydrazine and ethyl bromoacetate according to GP1, GP2 and GP3: LC/MS (an10n8): Rt 2.46 min, m/z 350.9 [M−H]⁺; ¹H NMR (CDCl₃): δ 3.81 (s, 3H), 4.77 (s, 2H), 7.02-7.16 (m, 3H), 7.41 (d, J=7.5 Hz, 1H), 7.50 (t, J=8.1 Hz, 2H), 7.73 (d, J=8.5 Hz, 2H), 8.17 (s, 1H), 8.52 (s, 1H).

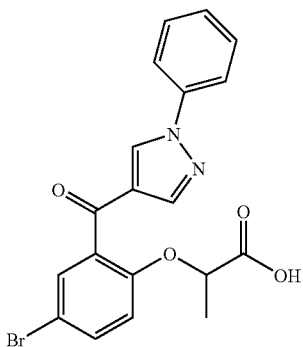

2-[4-Bromo-2-(1-phenyl-1H-pyrazole-4-carbonyl)phenoxy]propionic acid. Prepared from (5-bromo-2-hydroxyphenyl)-(1-phenyl-1H-pyrazol-4-yl)ketone and ethyl 2-bromopropionate according to GP2 and GP3: LC/MS (an 10p8) Rt 2.51 min, m/z 415 [M+H]⁺; ¹H NMR (CDCl₃): δ 1.65 (d, J=6.8 Hz, 3H), 4.93 (q, J=6.8 Hz, 1H), 6.96 (d, J=8.9 Hz, 1H), 7.35-7.43 (m, 1H), 7.46-7.53 (m, 2H), 7.62 (dd, J=8.9, 2.5 Hz, 1H), 7.70-7.76 (m, 3H), 8.17 (s, 1H), 8.52 (s, 1H); ¹³C NMR (CDCl₃): δ18.8, 75.2, 114.8, 116.7, 120.1, 124.4, 128.3, 130.0, 133.3, 136.2, 139.2, 143.3, 155.0, 173.1, 187.8.

2(S)-[4-Bromo-2-(1-phenyl-1H-pyrazole-4-carbonyl)-phenoxy]-propionic acid. (5-Bromo-2-hydroxyphenyl)-(1-phenyl-1H-pyrazol-4-yl)ketone (100 mg, 0.29 mmol), (R)-(+)-bromoacetic acid (44 mg, 0.29 mmol) ethyl 2-bromopropionate and K2CO3 (80 mg, 0.58 mmol) in acetone was stirred at room temperature for 16 h. The reaction mixture was concentrated and the residue was partitioned between EtOAc and dilute HCl (pH~1). The organic phase was dried (Na₂SO₄) and concentrated, and the residue was purified by flash chromatography (EtOAc:heptane, 1:1) to yield 55 mg (46%) of the title compound: Chiral HPLC (Column: Ciracel OD (0.46 cm×24 cm); Eluent: isocratic, 85% hexane+15% 2-propanol+0.1% TFA; Flow 0.5 mL/min) Rt 15.7 min, >90% e.e. (Racemic material eluates with baseline separation of enantiomers: Rt 15.7 and 16.7 min.) MS and NMR spectra correspond to racemic material.

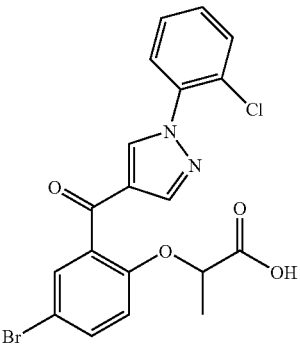

2-{4-Bromo-2-[1-(2-chlorophenyl)-1-H-pyrazole-4-carbonyl]phenoxy}propionic acid. Prepared from 6-bromo-3-formylchromone, 2-chlorophenylhydrazine and ethyl 2-bromopropionate according to GP1, GP2 and GP3: LC/MS (an10n8): Rt 2.56 min, 448.9 m/z [M−H]⁺; ¹H NMR (CDCl₃): δ 1.65 (d, J=7.0 Hz, 3H), 4.93 (q, J=7.0 Hz, 1H), 6.96 (d, J=8.9 Hz, 1H), 7.41-7.47 (m, 2H), 7.55-7.64 (m, 3H), 7.74 (s, 1H), 8.23 (s, 1H), 8.42 (s, 1H); ¹³C NMR (CDCl₃): δ18.9, 75.4, 115.0, 117.0, 124.1, 128.1, 128.4, 128.9, 130.7, 131.3, 133.6, 136.4, 136.8, 137.3, 143.3, 155.2, 173.5, 188.0.

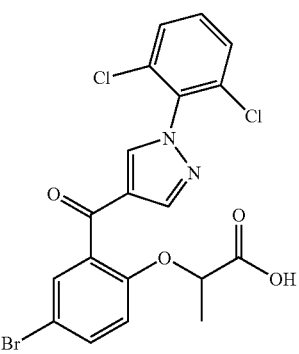

2-{4-Bromo-2-[1-(2,6-dichlorophenyl)-1H-pyrazole-4-carbonyl]phenoxy}-propionic acid. Prepared from 6-bromo-3-formylchromone, 2,6-dichlorophenyl-hydrazine and ethyl 2-bromopropionate according to GP1, GP2 and GP3: LC/MS (an10n8): Rt 2.55 min, 482.9 m/z [M−H]⁺; ¹H NMR (CDCl₃): δ 1.65 (d, J=6.8 Hz, 3H), 4.91 (q, J=6.8 Hz, 1H), 6.93 (d, J=8.9 Hz, 1H), 7.41-7.53 (m, 3H), 7.62 (dd, J=8.9, 2.5 Hz, 1H), 7.74 (d, J=2.4, 1H), 8.17 (s, 1H), 8.28 (s, 1H); ¹³C NMR (CDCl₃): δ18.9, 75.1, 114.9, 116.8, 124.2, 129.3, 130.7, 132.0, 133.6, 134.5, 135.6, 136.4, 137.6, 143.6, 155.1, 173.6, 187.8.

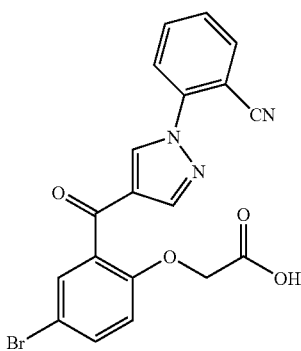

D40

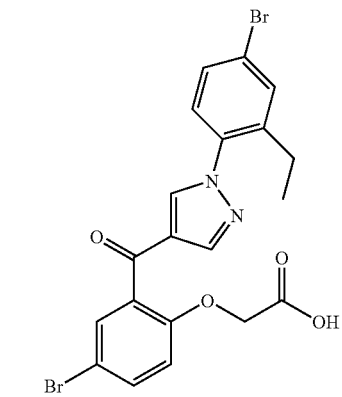

D42

{4-Bromo-2-[1-(2-cyano-phenyl)-1H-pyrazole-4-carbonyl]phenoxy}acetic acid. Prepared from 6-bromo-3-formylchromone, 2-hydrazinobenzonitril (prepared according to van der Mey, et al. *J. Med. Chem.* 2003, 2008-2016) and ethyl bromoacetate according to GP1, GP2 and GP3: $^1$H NMR (DMSO-d$_6$): δ 4.72 (s, 2H), 7.17 (d, J=8.9 Hz, 1H), 7.36 (t, J=15.1, 7.3 Hz, 1H), 7.8 (m, 4H), 8.29 (d, J=8.3 Hz, 1H), 9.03 (s, 1H), 9.66 (s, 1H), 13.04 (br s, 1H).

{4-Bromo-2-[1-(4-bromo-2-ethylphenyl)-1H-pyrazole-4-carbonyl]phenoxy}acetic acid. Prepared from 6-bromo-3-formylchromone, 4-bromo-2-ethylphenylhydrazine and ethyl bromoacetate according to GP1, GP2 and GP3: LC/MS (an10n8): Rt 2.78 min, m/z 506.6 [M−H]$^−$; $^1$H NMR (CDCl$_3$): δ 1.16 (td, J=7.8, 2.4 Hz, 3H), 2.58 (qd, J=7.8, 1.8 Hz, 2H), 4.77 (s, 2H), 6.94 (d, J=9.0 Hz, 1H), 7.22 (d, J=8.5 Hz, 1H), 7.47 (d, J=8.5 Hz, 1H), 7.56 (s, 1H), 7.65 (d, J=8.7 Hz, 1H), 7.72 (s, 1H), 8.15 (s, 1H), 8.19 (s, 1H).

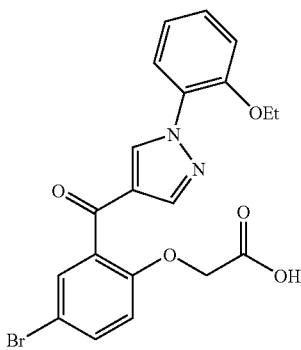

D41

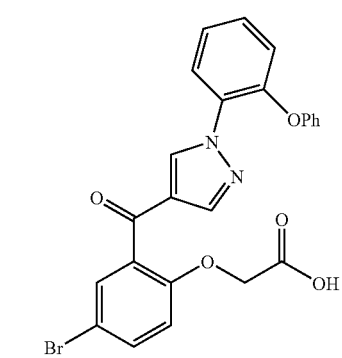

D43

{4-Bromo-2-[1-(2-ethoxyphenyl)-1H-pyrazole-4-carbonyl]phenoxy}acetic acid. Prepared from 6-bromo-3-formylchromone, 2-ethoxyphenylhydrazine and ethyl 2-bromoacetate according to GP1, GP2 and GP3: LC/MS (an10p8): Rt 2.33 min, m/z 446.7 [M+H]$^+$; $^1$H NMR (CDCl$_3$): δ 1.47 (t, J=7.0 Hz, 3H), 4.18 (q, J=7.0 Hz, 2H), 4.78 (s, 2H), 6.97 (d, J=8.9 Hz, 1H), 7.09 (d, J=8.7 Hz, 2H), 7.36 (td, J=7.9, 1.8 Hz, 1H), 7.64 (dd, J=8.9, 2.5 Hz, 1H), 7.79 (d, J=2.5 Hz, 1H), 7.80 (dd, J=7.9, 1.6 Hz, 1H), 8.22 (s, 1H), 8.65 (s, 1H).

{4-Bromo-2-[1-(2-phenoxyphenyl)-1H-pyrazole-4-carbonyl]phenoxy}acetic acid. Prepared from 6-bromo-3-formylchromone, 4-bromo-2-ethylphenylhydrazine and ethyl bromoacetate according to GP1, GP2 and GP3: LC/MS (an10n8): Rt 2.77 min, m/z 492.7 [M−H]$^−$; $^1$H NMR (CDCl$_3$): δ4.75 (s, 2H), 6.95 (d, J=8.6 Hz, 1H), 7.00-7.09 (m, 3H), 7.15 (t, J=7.5 Hz, 1H), 7.29-7.40 (m, 4H), 7.62-7.68 (m, 2H), 7.90 (d, J=9.0 Hz, 1H), 8.17 (s, 1H), 8.60 (s, 1H).

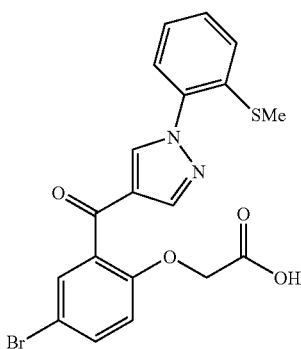

D44

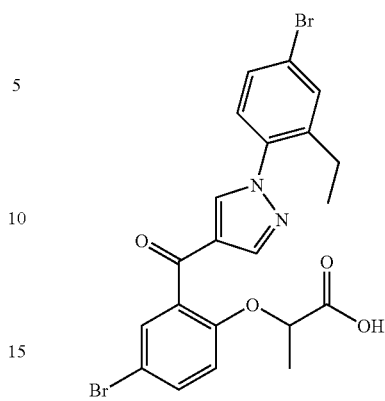

D46

{4-Bromo-2-[1-(2-methylthiophenyl)-1H-pyrazole-4-carbonyl]phenoxy}acetic acid. Prepared from 6-bromo-3-formylchromone, 2-methylthiophenylhydrazine and ethyl bromoacetate according to GP1, GP2 and GP3: LC/MS (an10n8): Rt 2.26 min, m/z 446.7 [M−H]⁻; $^1$H NMR (CDCl$_3$): δ2.46 (s, 3H), 4.77 (s, 2H), 6.93 (d, J=8.9 Hz, 1H), 7.28-7.32 (m, 1H), 7.39-7.49 (m, 3H), 7.62 (dd, J=9.0, 2.5 Hz, 1H), 7.76 (s, 1H), 8.23 (s, 1H), 8.31 (s, 1H).

2-{4-Bromo-2-[1-(4-bromo-2-ethylphenyl)-1H-pyrazole-4-carbonyl]phenoxy}-propionic acid. Prepared from 6-bromo-3-formylchromone, 4-bromo-2-ethylphenylhydrazine and ethyl bromoacetate according to GP1, GP2 and GP3: LC/MS (an10p8): Rt 2.72 min, m/z 522.6 [M+H]⁺; $^1$H NMR (CDCl$_3$): δ1.16 (t, J=7.7 Hz, 3H), 1.67 (d, J=6.8 Hz, 3H), 2.59 (q, J=7.5 Hz, 2H), 4.95 (q, J=7.0 Hz, 1H), 6.96 (d, J=9.0 Hz, 1H), 7.21 (d, J=8.3 Hz, 1H), 7.47 (d, J=8.7 Hz, 1H), 7.55 (s, 1H), 7.63 (d, J=9.0 Hz, 1H), 7.73 (s, 1H), 8.17 (s, 1H), 8.18 (s, 1H).

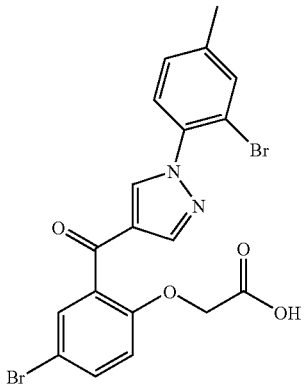

D45

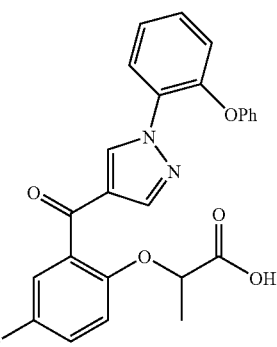

D47

{4-Bromo-2-[1-(2-bromo-4-methylphenyl)-1H-pyrazole-4-carbonyl]phenoxy}-acetic acid. Prepared from 6-bromo-3-formylchromone, 2-bromo-4-methylphenyl-hydrazine and ethyl bromoacetate according to GP1, GP2 and GP3: LC/MS (an10n8): Rt 2.47 min, m/z 492.6 [M−H]⁻; $^1$H NMR (CDCl$_3$): δ 2.44 (s, 3H), 4.80 (s, 2H), 6.99 (d, J=8.9 Hz, 1H), 7.27-7.30 (m, 1H), 7.46 (d, J=8.1 Hz, 1H), 7.58 (s, 1H), 7.67 (d, J=9.0 Hz, 1H), 7.80 (s, 1H), 8.20 (s, 1H), 8.33 (s, 1H).

2-{4-Bromo-2-[1-(2-phenoxyphenyl)-1H-pyrazole-4-carbonyl]phenoxy}propionic acid. Prepared from 6-bromo-3-formylchromone, 2-phenoxyphenylhydrazine and ethyl 2-bromopropionate according to GP1, GP2 and GP3: LC/MS (an 10p8): Rt 2.68 min, m/z 508.7 [M+H]⁺; $^1$H NMR (CDCl$_3$): δ 1.65 (d, J=6.8 Hz, 3H), 4.92 (q, J=7.3 Hz, 1H), 6.96-7.18 (m, 5H), 7.26-7.39 (m, 4H), 7.62 (d, J=8.6 Hz, 1H), 7.67 (s, 1H), 7.90 (d, J=7.5 Hz, 1H), 8.17 (s, 1H), 8.61 (s, 1H).

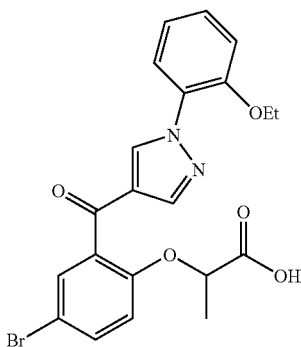

D48

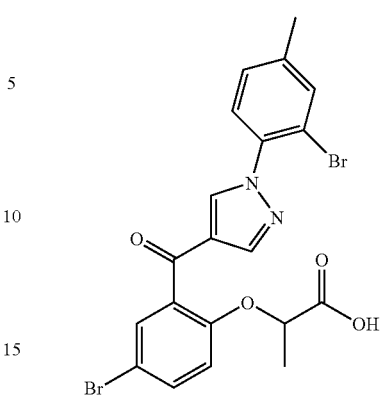

D50

2-{4-Bromo-2-[1-(2-ethoxyphenyl)-1H-pyrazole-4-carbonyl]phenoxy}propionic acid. Prepared from 6-bromo-3-formylchromone, 2-ethoxyphenylhydrazine and ethyl 2-bromopropionate according to GP1, GP2 and GP3:

LC/MS (an10p8): Rt 2.39 min, m/z 458.7 [M+H]$^+$; $^1$H NMR (CDCl$_3$): δ 1.49 (t, J=7.1 Hz, 3H), 1.86 (d, J=7.1 Hz, 3H), 4.19 (m, 2H), 4.98 (q, J=6.9 Hz, 1H), 7.02-7.12 (m, 3H), 7.37 (t, J=8.2 Hz, 1H), 7.66 (d, J=8.9 Hz, 1H), 7.78 (s, 1H), 7.83 (d, J=7.9 Hz, 1H), 8.20 (s, 1H), 8.67 (s, 1H).

2-{4-Bromo-2-[1-(2-bromo-4-methylphenyl)-1H-pyrazole-4-carbonyl]phenoxy}propionic acid. Prepared from 6-bromo-3-formylchromone, 2-bromo-4-methylphenylhydrazine and ethyl 2-bromopropionate according to GP1, GP2 and GP3: LC/MS (an10n8): Rt 2.74 min, 506.8 m/z [M−H]$^+$; $^1$H NMR (CDCl$_3$): δ 1.72 (d, J=7.0 Hz, 3H), 2.45 (s, 3H), 4.98 (q, J=7.0 Hz, 1H), 7.03 (d, J=8.9 Hz, 1H), 7.28-7.30 (m, 1H), 7.46 (d, J=8.1 Hz, 1H), 7.59 (s, 1H), 7.67 (dd, J=8.9, 2.43 Hz, 1H), 7.81 (d, J=2.6 Hz, 1H), 8.19 (s, 1H), 8.34 (s, 1H).

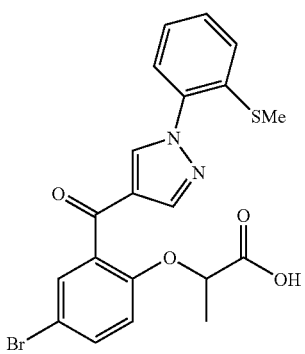

D49

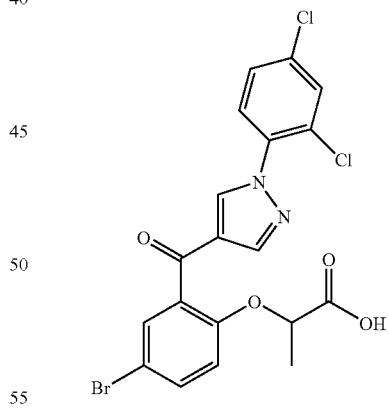

D51

2-{4-Bromo-2-[1-(2-methylthio)-1H-pyrazole-4-carbonyl]phenoxy}propionic acid. Prepared from 6-bromo-3-formylchromone, 2-ethoxyphenylhydrazine and ethyl 2-bromopropionate according to GP1, GP2 and GP3: LC/MS (an10n8): Rt 2.56 min, 460.9 m/z [M−H]$^+$; $^1$H NMR (CDCl$_3$): δ 1.71 (d, J=6.8 Hz, 3H), 2.46 (s, 3H), 4.96 (q, J=7.0 Hz, 1H), 7.00 (d, J=8.9 Hz, 1H), 7.29-7.34 (m, 1H), 7.40-7.50 (m, 3H), 7.64 (dd, J=8.9, 2.5 Hz, 1H), 7.80 (s, 1H), 8.22 (s, 1H), 8.32 (s, 1H).

2-{4-Bromo-2-[1-(2,4-dichlorophenyl)-1H-pyrazole-4-carbonyl]phenoxy}-propionic acid. Prepared from 6-bromo-3-formylchromone, 2,4-dichlorophenyl-hydrazine and ethyl 2-bromopropionate according to GP1, GP2 and GP3: LC/MS (an10n8): Rt 2.83 min, 482.8 m/z [M−H]$^+$; $^1$H NMR (CDCl$_3$): δ 1.50 (d, J=6.0 Hz, 3H), 4.75 (q, J=4.5 Hz, 1H), 6.88 (d, J=8.5 Hz, 1H), 7.40 (dd, J=8.5, 1.9 Hz, 1H), 7.50 (d, J=7.5 Hz, 1H), 7.54-7.57 (m, 2H), 7.61 (s, 1H), 8.16 (s, 1H), 8.32 (s, 1H).

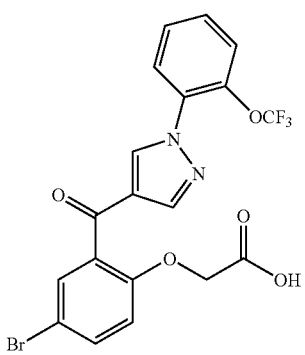

D52

{4-Bromo-2-[1-(2-trifluoromethoxyphenyl)-1H-pyrazole-4-carbonyl]phenoxy}acetic acid. Prepared from 6-bromo-3-formylchromone, 2-trifluoromethoxyphenylhydrazine and ethyl bromoacetate according to GP1, GP2 and GP3: LC/MS (an10n8): Rt 2.43 min, m/z 482.7 [M–H]$^-$; $^1$H NMR (CDCl$_3$): δ 4.77 (s, 2H), 6.95 (d, J=8.6 Hz, 1H), 7.45-7.50 (m, 3H), 7.65 (dd, J=8.9, 2.5 Hz, 1H), 7.73 (d, J=2.4 Hz, 1H), 7.82 (s, 1H), 8.23 (s, 1H), 8.40 (s, 1H).

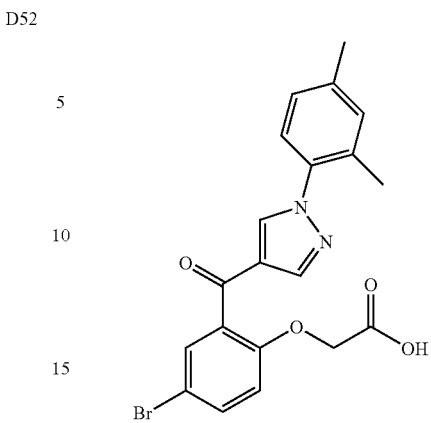

D54

{4-Bromo-2-[1-(2,4-dimethylphenyl)-1H-pyrazole-4-carbonyl]phenoxy}acetic acid. Prepared from 6-bromo-3-formylchromone, 2,4-dimethylphenylhydrazine and ethyl bromoacetate according to GP1, GP2 and GP3: LC/MS (an10n8): Rt 2.41 min, m/z 428.7 [M–H]$^-$; $^1$H NMR (CDCl$_3$): δ 2.26 (s, 3H), 2.40 (s, 3H), 4.75 (s, 2H), 6.91 (d, J=8.9 Hz, 1H), 7.11 (d, J=8.1 Hz, 1H), 7.17 (s, 1H), 7.23 (d, J=8.1 Hz, 1H), 7.60 (dd, J=8.9, 2.46 Hz, 1H), 7.71 (s, 1H), 8.15 (s, 1H), 8.22 (s, 1H).

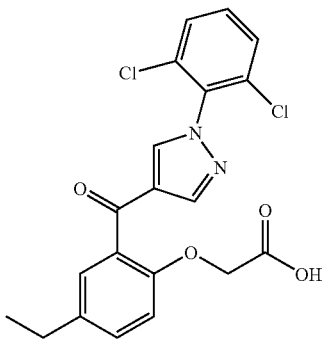

D53

{2-[1-(2,6-Dichlorophenyl)-1H-pyrazole-4-carbonyl]-4-ethylphenoxy}acetic acid. Prepared from 6-ethyl-3-formylchromone, 2,6-dichlorophenylhydrazine and ethyl bromoacetate according to GP1, GP2 and GP3: LC/MS (an10n8): Rt 2.25 min, m/z 416.8 [M–H]$^-$; $^1$H NMR (CDCl$_3$): δ 1.26 (t, J=7.5 Hz, 3H), 2.69 (q, J=7.7 Hz, 2H), 4.82 (s, 2H), 7.04 (d, J=8.7 Hz, 1H), 7.39-7.44 (m, 1H), 7.46-7.54 (m, 4H), 8.14 (s, 1H), 8.25 (s, 1H).

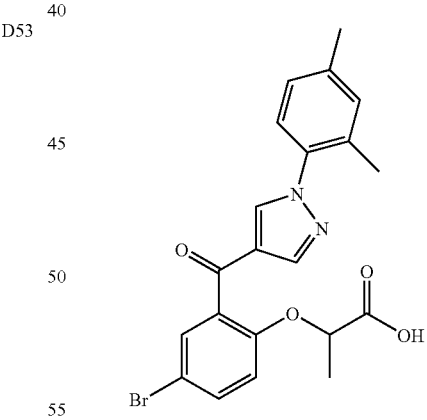

D55

2-{4-Bromo-2-[1-(2,4-dimethylphenyl)-1H-pyrazole-4-carbonyl]phenoxy}-propionic acid. Prepared from 6-bromo-3-formylchromon, 2,4-dimethylphenyl-hydrazine and ethyl 2-bromopropionate according to GP1, GP2 and GP3: LC/MS (an10n8): Rt 2.40 min, m/z 442.7 [M–H]$^-$; $^1$H NMR (CDCl$_3$): δ 1.67 (d, J=6.9 Hz, 3H), 2.25 (s, 3H), 2.40 (s, 3H), 4.93 (q, J=6.8 Hz, 1H), 6.97 (d, J=8.9 Hz, 1H), 7.12 (d, J=8.1 Hz, 1H), 7.17 (s, 1H), 7.25 (d, J=8.1 Hz, 1H), 7.62 (dd, J=8.7, 1.52 Hz, 1H), 7.73 (s, 1H), 8.15-8.16 (m, 2H).

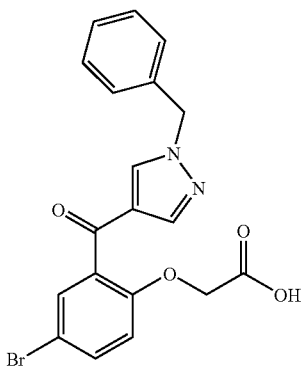

D56

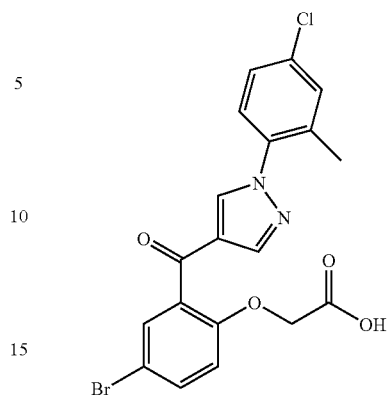

D58

[2-(1-Benzyl-1H-pyrazole-4-carbonyl)-4-bromophenoxy]acetic acid. Prepared from 6-bromo-3-formylchromone, benzylhydrazine and ethyl bromoacetate according to GP1, GP2 and GP3: LC/MS (an10n8): Rt 2.14 min, m/z 414.7 [M−H]⁻; $^1$H NMR (CDCl$_3$): δ 4.70 (s, 2H), 5.36 (s, 2H), 6.88 (d, J=8.7 Hz, 1H), 7.28-7.30 (m, 2H), 7.40-7.46 (m, 3H), 7.57 (d, J=8.9 Hz, 1H), 7.63 (s, 1H), 8.01 (s, 1H), 8.04 (s, 1H).

{4-Bromo-2-[1-(4-chloro-2-methylphenyl)-1H-pyrazole-4-carbonyl]phenoxy}-acetic acid. Prepared from 6-bromo-3-formylchromone, 4-chloro-2-methylphenyl-hydrazine and ethyl bromoacetate according to GP1, GP2 and GP3: LC/MS (an10n8): Rt 2.49 min, m/z 448.7 [M−H]⁻; $^1$H NMR (CDCl$_3$): δ 2.27 (s, 3H), 4.75 (s, 2H), 6.91 (d, J=8.9 Hz, 1H), 7.31 (s, 2H), 7.36 (s, 1H), 7.63 (d, J=8.7 Hz, 1H), 7.70 (s, 1H), 8.17 (s, 1H), 8.21 (s, 1H).

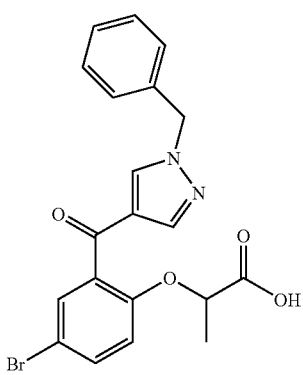

D57

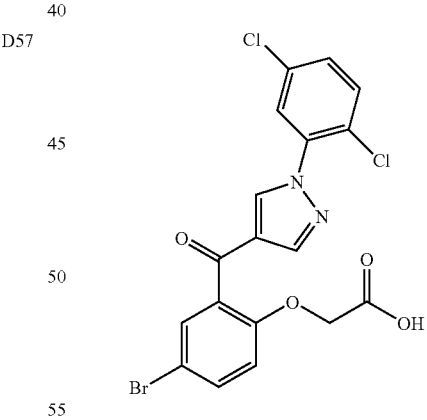

D59

2-[2-(1-Benzyl-1H-pyrazole-4-carbonyl)-4-bromophenoxy]propionic acid. Prepared from 6-bromo-3-formylchromone, benzylhydrazine and ethyl 2-bromopropionate according to GP1, GP2 and GP3: LC/MS (an10n8): Rt 2.16 min, m/z 428.8 [M−H]⁻; $^1$H NMR (CDCl$_3$): δ 1.59 (d, J=6.8 Hz, 3H), 4.88 (q, J=7.1 Hz, 1H), 5.35 (s, 2H), 6.91 (d, J=8.9 Hz, 1H), 7.30-7.42 (m, 5H), 7.53-7.71 (m, 2H), 8.01 (s, 2H).

{4-Bromo-2-[1-(2,5-dichlorophenyl)-1H-pyrazole-4-carbonyl]phenoxy}acetic acid. Prepared from 6-bromo-3-formylchromone, 2,5-dichlorophenylhydrazine and ethyl bromoacetate according to GP1, GP2 and GP3: LC/MS (an10n8): Rt 2.46 min, m/z 468.6 [M−H]⁻; $^1$H NMR (CDCl$_3$): δ4.78 (s, 2H), 6.92 (d, J=8.9 Hz, 1H), 7.39 (dd, J=8.7, 2.44 Hz, 1H), 7.50 (d, J=8.7 Hz, 1H), 7.61 (dd, J=8.9, 2.53 Hz, 1H), 7.70 (dd, J=8.1, 2.36 Hz, 2H), 8.22 (s, 1H), 8.45 (s, 1H).

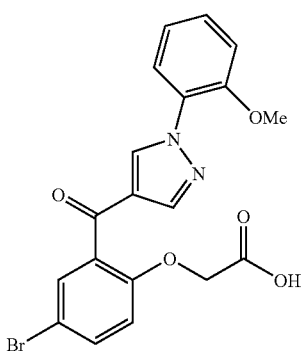

D60

{4-Bromo-2-[1-(2-methoxyphenyl)-1H-pyrazole-4-carbonyl]phenoxy}acetic acid. Prepared from 6-bromo-3-formylchromone, 2-methylphenylhydrazine and ethyl bromoacetate according to GP1, GP2 and GP3: LC/MS (an10n8): Rt 2.20 min, m/z 430.7 [M–H]$^-$; $^1$H NMR (CDCl$_3$): δ 3.96 (s, 3H), 4.79 (s, 2H), 6.96 (d, J=8.9 Hz, 1H), 7.11 (t, J=8.2 Hz, 2H), 7.40 (t.d, J=8.1, 1.5 Hz, 1H), 7.65 (dd, J=8.9, 2.5 Hz, 1H), 7.76 (d, J=2.5 Hz, 2H), 8.18 (s, 1H), 8.60 (s, 1H).

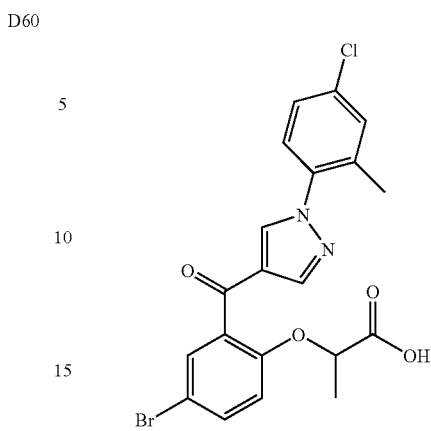

D62

2-{4-Bromo-2-[1-(4-chloro-2-methylphenyl)-1H-pyrazole-4-carbonyl]phenoxy}-propionic acid. Prepared from 6-bromo-3-formylchromone, 4-chloro-2-methylphenylhydrazine and ethyl 2-bromopropionate according to GP1, GP2 and GP3: LC/MS (an10n8): Rt 2.55 min, m/z 462.7 [M–H]$^-$; $^1$H NMR (CDCl$_3$): δ 1.65 (d, J=6.9 Hz, 3H), 2.28 (s, 3H), 4.92 (d, J=6.8 Hz, 1H), 6.95 (d, J=8.9 Hz, 1H), 7.30 (s, 2H), 7.37 (s, 1H), 7.63 (d, J=8.9 Hz, 1H), 7.72 (s, 1H), 8.19 (s, 2H).

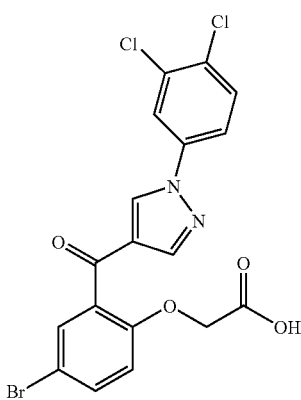

D61

{4-Bromo-2-[1-(3,4-dichlorophenyl)-1H-pyrazole-4-carbonyl]phenoxy}acetic acid. Prepared from 6-bromo-3-formylchromone, 3,4-chlorophenylhydrazine and ethyl bromoacetate according to GP1, GP2 and GP3: LC/MS (an10n8): Rt 2.77 min, m/z 468.6 [M–H]$^-$; $^1$H NMR (CDCl$_3$): δ 4.78 (s, 2H), 6.90 (d, J=8.7 Hz, 1H), 7.59 (d, J=8.1 Hz, 1H), 7.64 (d, J=8.9 Hz, 1H), 7.69 (d, J=2.43 Hz, 2H), 7.91 (d, J=2.46 Hz, 1H), 8.18 (s, 1H), 8.53 (s, 1H).

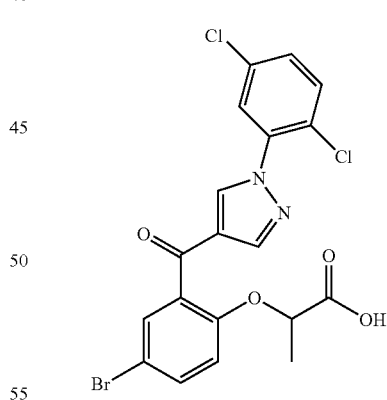

D63

2-{4-Bromo-2-[1-(2,5-dichlorophenyl)-1H-pyrazole-4-carbonyl]phenoxy}-propionic acid. Prepared from 6-bromo-3-formylchromone, 2,5-dichlorophenyl-hydrazine and ethyl 2-bromopropionate according to GP1, GP2 and GP3: LC/MS (an10n8): Rt 2.51 min, m/z 482.6 [M–H]$^-$; $^1$H NMR (CDCl$_3$): δ 1.70 (d, J=6.8 Hz, 3H), 4.90 (q, J=6.9 Hz, 1H), 6.93 (d, J=9.1 Hz, 1H), 7.40 (dd, J=8.7, 2.5 Hz, 1H), 7.50 (d, J=8.6 Hz, 1H), 7.62 (dd, J=8.9, 2.5 Hz, 1H), 7.68 (d, J=2.3 Hz, 1H), 7.71 (d, J=2.4 Hz, 1H), 8.22 (s, 1H) 8.45 (s, 1H).

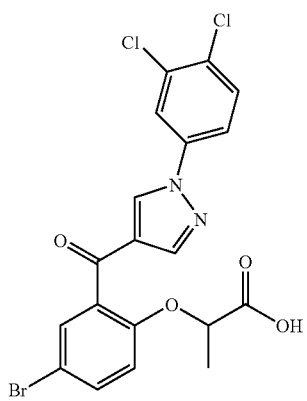

D64

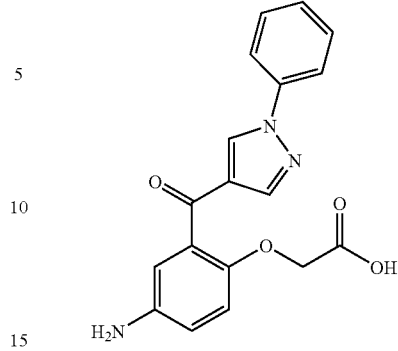

D66

2-{4-Bromo-2-[1-(3,4-dichloro-phenyl)-1H-pyrazole-4-carbonyl]phenoxy}-propionic acid. Prepared from 6-bromo-3-formylchromon, 3,4-dichlorophenyl-hydrazine and ethyl 2-bromopropionate according to GP1, GP2 and GP3: LC/MS (an10n8): Rt 2.83 min, m/z 482.6 [M–H]⁻; $^1$H NMR (CDCl$_3$): δ 1.63 (d, J=6.8 Hz, 3H), 4.93 (q, J=6.9 Hz, 1H), 6.92 (d, J=9.03 Hz, 1H), 7.55-7.65 (m, 3H), 7.70 (s, 1H), 7.93 (d, J=2.25 Hz, 1H), 8.20 (s, 1H), 8.57 (s, 1H).

[4-Amino-2-(1-phenyl-1H-pyrazole-4-carbonyl)phenoxy]acetic acid. A mixture of ethyl 4-nitro-2-(phenyl-1H-pyrazole-4-carbonyl)phenoxyacetate (190 mg, 0.48 mmol) and 10% Pd/C (100 mg) in MeOH (50 mL) was stirred under an atmosphere of hydrogen of 12 h, then filtered through a pad of celite and concentrated, and the product was hydrolyzed according to GP3 to give the title compound.

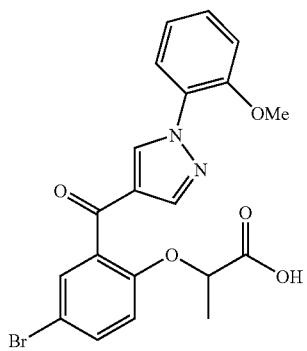

D65

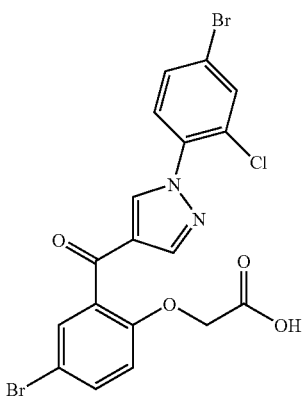

D67

2-{4-Bromo-2-[1-(2-methoxyphenyl)-1H-pyrazole-4-carbonyl]phenoxy}propionic acid. Prepared from 6-ethyl-3-formylchromone, 2,6-dichlorophenylhydrazine and ethyl 2-bromopropionate according to GP1, GP2 and GP3: LC/MS (an10n8): Rt 2.23 min, m/z 444.7 [M–H]⁻; $^1$H NMR (CDCl$_3$): δ 1.68 (d, J=7.0 Hz, 3H), 3.95 (s, 3H), 4.95 (d, J=7.0 Hz, 1H), 6.99 (d, J=8.7 Hz, 1H), 7.10 (d, J=8.5 Hz, 1H), 7.14 (s, 1H), 7.37-7.43 (m, 1H), 7.63 (dd, J=8.9, 2.6 Hz, 1H), 7.77 (s, 1H), 7.79 (s, 1H), 8.19 (s, 1H), 8.62 (s, 1H).

{4-Bromo-2-[1-(4-bromo-2-chlorophenyl)-1H-pyrazole-4-carbonyl]phenoxy}-acetic acid. Prepared from 6-bromo-3-formylchromone, 4-bromo-2-chlorophenyl-hydrazine and ethyl bromoacetate according to GP1, GP2 and GP3: LC/MS (an10n8): Rt 2.57 min, m/z 526.6 [M–H]⁻; $^1$H NMR (DMSO): δ 1.31 (d, J=6.8 Hz, 3H), 4.94 (q, J=6.6 Hz, 1H), 6.92 (d, J=8.9 Hz, 1H), 7.53 (d, J=2.5 Hz, 1H), 7.59 (d, J=8.5 Hz, 1H), 7.66 (dd, J=9.0, 2.5 Hz, 1H), 7.76 (dd, J=8.5, 2.3 Hz, 1H), 8.04 (d, J=2.1 Hz, 1H), 8.22 (s, 1H), 8.77 (s, 1H).

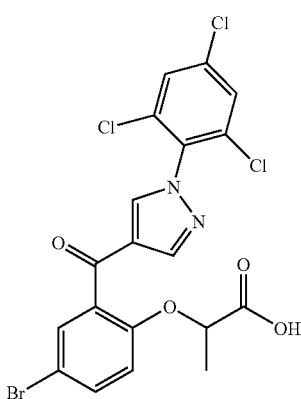

D68

2-{4-Bromo-2-[1-(2,4,6-trichlorophenyl)-1H-pyrazole-4-carbonyl]phenoxy}-propionic acid. Prepared from 6-bromo-3-formylchromone, 2,4,6-trichlorophenylhydrazine and ethyl 2-bromopropionate according to GP1, GP2 and GP3: LC/MS (an10n8): Rt 2.61 min, m/z 516.6 [M−H]+; 1H NMR (DMSO): δ 1.33 (d, J=6.8 Hz, 3H), 4.94 (q, J=7.0 Hz, 1H), 6.92 (d, J=9.2 Hz, 1H), 7.54 (d, J=2.4 Hz, 1H), 7.66 (dd, J=8.9, 2.5 Hz, 1H), 7.99 (s, 2H), 8.26 (s, 1H), 8.72 (s, 1H).

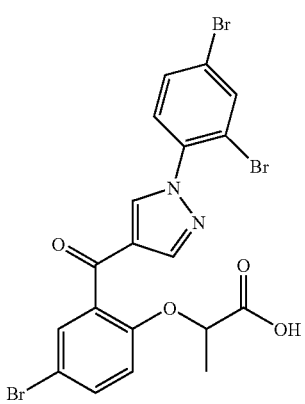

D69

2-{4-Bromo-2-[1-(2,4-dibromophenyl)-1H-pyrazole-4-carbonyl]phenoxy}-propionic acid. Prepared from 6-bromo-3-formylchromone, 2,4-dibromo-phenylhydrazine and ethyl 2-bromopropionate according to GP1, GP2 and GP3: LC/MS (an 10p8): Rt 2.87 min, m/z 572.7 [M+H]+; 1H NMR (DMSO): δ 1.32 (d, J=6.8 Hz, 3H), 4.93 (q, J=6.8 Hz, 1H), 6.91 (d, J=8.9 Hz, 1H), 7.54 (dd, J=8.3, 2.3 Hz, 2H), 7.66 (dd, J=8.9, 2.5 Hz, 1H), 7.78 (dd, J=8.6, 2.2 Hz, 1H), 8.15 (d, J=2.1 Hz, 1H), 8.21 (s, 1H), 8.72 (s, 1H).

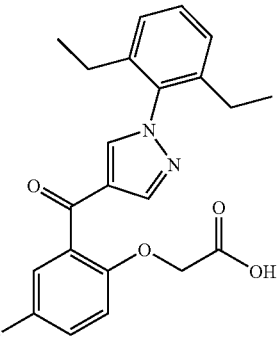

D70

{4-Bromo-2-[1-(2,6-diethyl-phenyl)-1H-pyrazole-4-carbonyl]phenoxy}acetic acid. Prepared from 6-bromo-3-formylchromone, 2,6-diethylphenylhydrazine and ethyl bromoacetate according to GP1, GP2 and GP3: LC/MS (an10n8): Rt 2.54 min, m/z 457.0 [M−H]+; 1H NMR (CDCl3): δ 1.27 (t, J=7.3 Hz, 6H), 2.35 (q, J=7.3 Hz, 4H), 4.82 (s, 2H), 6.99 (d, J=8.9 Hz, 1H), 7.29 (d, J=7.5 Hz, 2H), 7.48 (m, 1H), 7.67 (m, 1H), 7.79 (s, 1H), 8.11 (s, 1H), 8.27 (s, 1H), 8.87 (br s, 1H).

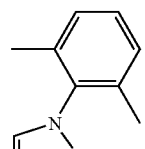

D71

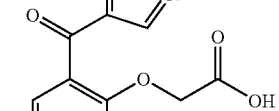

{4-Bromo-2-[1-(2,6-dimethylphenyl)-1H-pyrazole-4-carbonyl]phenoxy}acetic acid. Prepared from 6-bromo-3-formylchromone, 2,6-diethylphenylhydrazine and ethyl bromoacetate according to GP1, GP2 and GP3: LC/MS (an10n8): Rt 2.27 min, m/z 428.9 [M−H]+; 1H NMR (CDCl3): δ 2.07 (s, 6H), 4.74 (s, 2H), 6.91 (d, J=8.7 Hz, 1H), 7.19 (d, J=7.3 Hz, 2H), 7.25-7.35 (m, 1H), 7.55-7.66 (m, 1H), 7.71 (s, 1H), 8.06 (s, 1H), 8.23 (s, 1H), 8.91 (br s, 1H).

D72

{4-Bromo-2-[1-(2-ethyl-6-methylphenyl)-1H-pyrazole-4-carbonyl]phenoxy}acetic acid. Prepared from 6-bromo-3- formylchromone, 2-ethyl-6-methylphenylhydrazine and ethyl bromoacetate according to GP1, GP2 and GP3: LC/MS (an10n8): Rt 2.43 min, m/z 443.0 [M−H]+; 1H NMR (CDCl3): δ1.12 (t, J=7.8 Hz, 3H), 2.05 (s, 3H), 2.33 (q, J=7.8 Hz, 2H), 4.76 (s, 2H), 6.94 (d, J=8.7 Hz, 1H), 7.14-7.25 (m, 2H), 7.31-7.41 (m, 1H), 7.56-66 (m, 1H), 7.72 (s, 1H), 8.06 (s, 1H), 8.22 (s, 1H), 8.93 (br s, 1H).

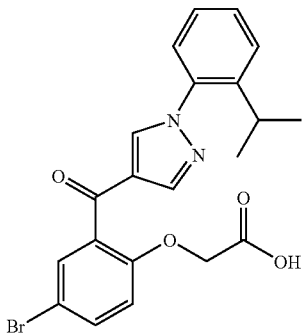

D73

{4-Bromo-2-[1-(2-isopropylphenyl)-1H-pyrazole-4-carbonyl]phenoxy}acetic acid. Prepared from 6-bromo-3-formylchromone, 2-ethyl-6-methylphenylhydrazine and ethyl bromoacetate according to GP1, GP2 and GP3: LC/MS (an10p8): Rt 2.76 min, m/z 444.9 [M+H]+; 1H NMR (CDCl3-d): δ 1.22 (d, J=6.5 Hz, 6H), 2.89 (septet, J=6.1 Hz, 1H), 4.76 (s, 2H), 6.92 (d, J=8.7 Hz, 1H), 7.30 (s, 2H), 7.49 (s, 2H), 7.62 (d, 1H), 7.72 (s, 1H), 8.15 (s, 1H), 8.20 (s, 1H), 8.92 (br s, 1H).

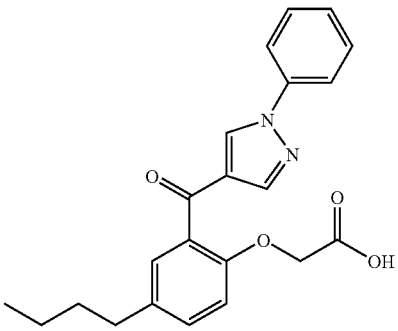

D75

[4-Butyl-2-(1-phenyl-1H-pyrazole-4-carbonyl)phenoxy]acetic acid. A solution of ethyl [4-bromo-2-(1-phenyl-1H-pyrazole-4-carbonyl)phenoxy]acetate (472 mg, 1.1 mmol), 1-butylboronic acid (102 mg, 1.0 mmol) and Pd (dppf)Cl2 (72 mg, 0.05 mmol) in THF (10 mL) and water (1 mL) under argon was refluxed for 24 h. The reaction mixture was extracted with CH2Cl2, the organic phase was filtered through celite and concentrated, and the residue was purified by flash chromatography (SiO2, EtOAc:heptane, 1:10 to 1:1). The purest fraction was concentrated (~10 mg), and the residue was hydrolysed according to GP3: LC/MS (an 10p8): Rt 2.59 min, m/z 379.1 [M+H]+; 1H NMR (CDCl3): δ 0.88 (t, J=7.5 Hz, 3H), 1.29 (m, 2H), 1.49 (m, 2H), 2.48 (m, 2H), 4.51 (s, 2H), 6.84 (m, 1H), 7.14 (m, 1H), 7.30 (m, 2H), 7.42 (m, 2H), 7.65 (m, 2H), 7.97 (s, 1H), 8.46 (s, 1H).

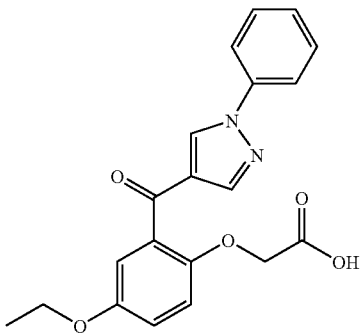

D74

[4-Ethoxy-2-(1-phenyl-1H-pyrazole-4-carbonyl)phenoxy]acetic acid. Prepared from 6-ethoxy-3-formylchromone, phenylhydrazine and ethyl bromoacetate according to GP1, GP2 and GP3: LC/MS (an10p8): Rt 1.97 min, m/z 367.1 [M+H]+; 1H NMR (CDCl3): δ 1.43 (t, J=6.8 Hz, 3H), 4.03 (q, J=6.9 Hz, 2H), 4.78 (s, 2H), 7.01-7.13 (m, 2H), 7.15 (s, 1H), 7.36-7.43 (m, 1H), 7.46-7.57 (m, 2H), 7.71-7.75 (m, 2H), 8.16 (s, 1H), 8.50 (s, 1H).

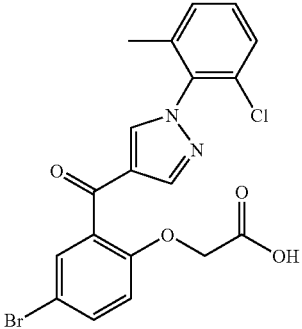

D76

{4-Bromo-2-[1-(2-chloro-6-methylphenyl)-1H-pyrazole-4-carbonyl]phenoxy}-acetic acid. Prepared from 6-bromo-3-formylchromone, 2-chloro-6-methyl-phenylhydrazine and ethyl bromoacetate according to GP1, GP2 and GP3: LC/MS (an 10p8): Rt 2.49 min, m/z 450.9 [M+H]+; 1H NMR (CDCl3): δ 2.16 (s, 3H), 4.80 (s, 2H), 6.98 (d, J=9.1 Hz, 1H), 7.30 (m, 1H), 7.34-7.40 (m, 2H), 7.66 (d, 1H), 7.77 (m, 1H), 8.13 (s, 1H); 8.24 (s, 1H).

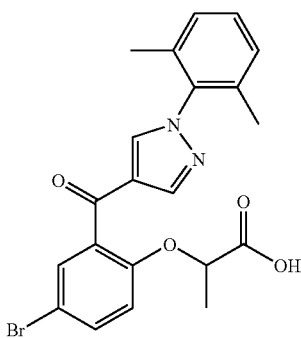

D77

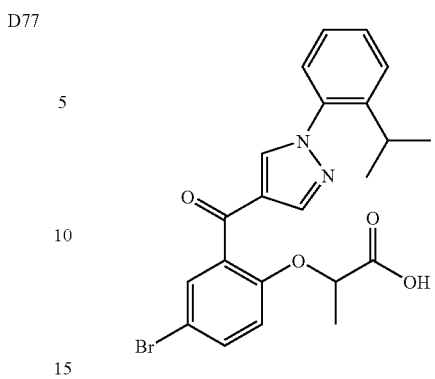

D79

2-{4-Bromo-2-[1-(2,6-dimethylphenyl)-1H-pyrazole-4-carbonyl]phenoxy}-propionic acid. Prepared from 6-bromo-3-formylchromone, 2,6-dimethyl-phenylhydrazine and ethyl 2-bromopropionate according to GP1, GP2 and GP3: LC/MS (an10n8): Rt 2.55 min, m/z 440.9 [M−H]+; $^1$H NMR (CDCl$_3$): δ 1.68 (d, J=6.8 Hz, 3H), 2.11 (s, 6H), 4.94 (q, J=7.0 Hz 1H), 6.97 (d, J=8.9 Hz, 1H), 7.19 (d, J=7.5 Hz 2H), 7.28-7.32 (m, 1H), 7.63 (d, J=8.1 Hz, 1H), 7.75 (m, 1H), 8.05 (s, 1H), 8.22 (s, 1H).

2-{4-Bromo-2-[1-(2-isopropylphenyl)-1H-pyrazole-4-carbonyl]phenoxy}-propionic acid. Prepared from 6-bromo-3-formylchromone, 2,6-diethyl-phenylhydrazine and ethyl 2-bromopropionate according to GP1, GP2 and GP3: LC/MS (an10p8): Rt 2.54 min, m/z 459.0 [M+H]+; $^1$H NMR (CDCl$_3$): δ 1.19-1.27 (m, 7H), 1.67 (d, J=7.0 Hz, 2H), 4.92 (q, J=6.8 Hz, 1H), 6.96 (d, J=8.9 Hz, 1H), 7.27-7.53 (m, 4H), 7.58-7.67 (m, 1H), 7.73 (s, 1H), 8.17 (s, 1H), 8.20 (s, 1H).

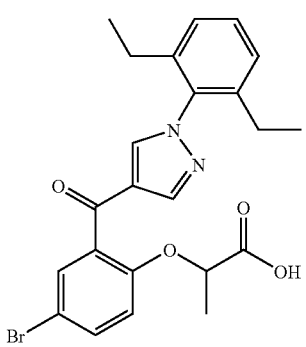

D78

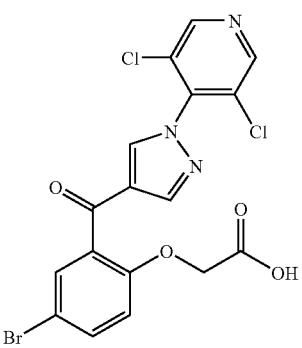

D80

2-{4-Bromo-2-[1-(2,6-diethylphenyl)-1H-pyrazole-4-carbonyl]phenoxy}propionic acid. Prepared from 6-bromo-3-formylchromone, 2,6-diethylphenylhydrazine and ethyl 2-bromopropionate according to GP1, GP2 and GP3: LC/MS (an10n8): Rt 2.85 min, m/z 469.0 [M−H]+; $^1$H NMR (CDCl$_3$): δ 1.08-1.21 (m, 6H), 1.69-1.76 (m, 3H), 2.18-2.48 (m, 4H), 2.67 (s, 1H), 4.97 (q, J=6.8 Hz 1H), 6.84 (d, J=9.0 Hz, 1H), 7.00 (d, J=9.0 Hz, 1H), 7.24 (d, J=7.7 Hz, 1H), 7.42 (d, J=8.1 Hz, 1H), 7.65 (d, J=9.0 Hz, 1H), 7.77 (s, 1H), 7.86 (s, 1H), 8.06 (s, 1H), 8.22 (s, 1H).

{4-Bromo-2-[1-(3,5-dichloropyridin-4-yl)-1H-pyrazole-4-carbonyl]phenoxy}acetic acid. Prepared from 6-bromo-3-formylchromone, 2,6-dichloropyridine-4-hydrazine and ethyl bromoacetate according to GP1, GP2 and GP3: LC/MS (an10n8): Rt 2.08 min, m/z 469.8 [M−H]−; $^1$H NMR (DMSO-d$_6$): δ 4.75 (s, 2H), 7.05 (d, J=9.1 Hz, 1H), 7.56 (s, 1H), 7.64 (d, J=9.1 Hz, 1H), 8.32 (s, 1H), 8.77 (s, 1H), 8.93 (s, 2H).

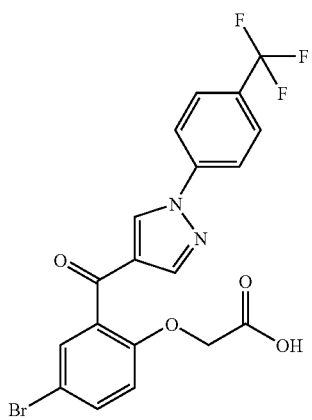

D81

{4-Bromo-2-[1-(4-trifluoromethylphenyl)-1H-pyrazole-4-carbonyl]phenoxy}-acetic acid. Prepared from 6-bromo-3-formylchromone, 4-trifluoromethylphenyl-hydrazine and ethyl bromoacetate according to GP1, GP2 and GP3: LC/MS (an10n8): Rt 2.88 min, m/z 468.9 [M–H]⁻; ¹H NMR (CDCl₃): δ 4.78 (s, 2H), 6.92 (d, J=8.9 Hz, 1H), 7.65 (d, J=8.9 Hz, 1H), 7.71 (s, 1H), 7.79 (d, J=8.9 Hz, 2H), 7.91 (d, J=8.9 Hz, 2H), 8.23 (s, 1H), 8.65 (s, 1H).

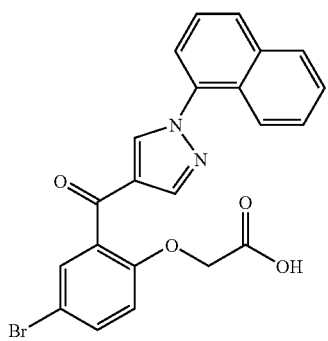

D82

[4-Bromo-2-(1-naphthalen-1-yl-1H-pyrazole-4-carbonyl)phenoxy]acetic acid. Prepared from 6-bromo-3-formylchromone, 1-naphtylhydrazine and ethyl bromoacetate according to GP1, GP2 and GP3: LC/MS (an10p8): Rt 2.649 min, m/z 451.0 [M+H]⁺; ¹H NMR (CDCl₃): δ 4.78 (s, 2H), 6.93 (d, J=8.85 Hz, 1H), 7.52-7.68 (m, 6H), 7.73-7.82 (m, 2H), 7.93-8.05 (m, 2H), 8.33 (s, 1H), 8.38 (s, 1H).

General synthetic route IV

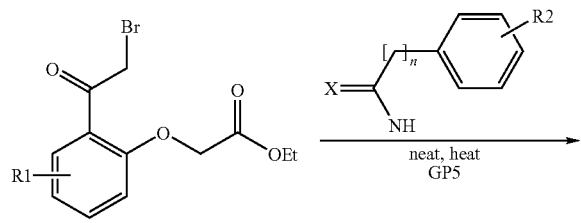

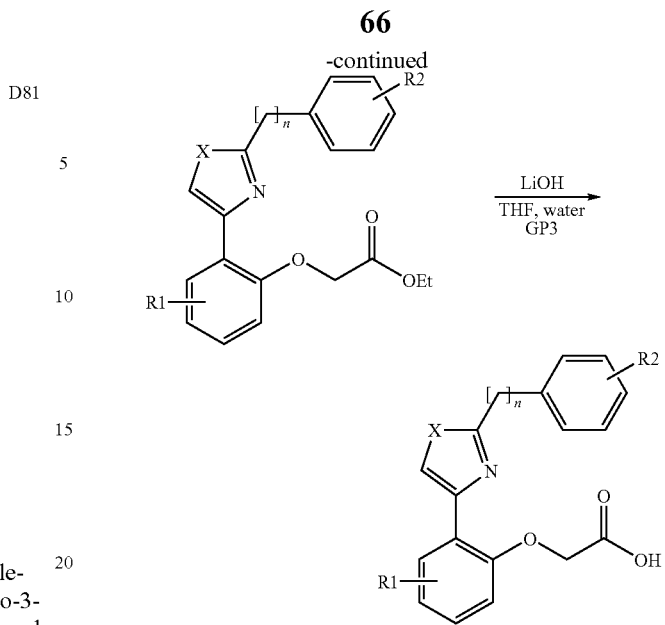

General Procedure 5 (GP5):

A mixture of ethyl 2-(2-bromoacetyl)phenoxyacetate (0.1 mmol) and amide (X=O) or thioamide (X=S) (2.5 mmol) was heated neat in the microwave for 3 hours at 140° C. After cooling, the solid residue was partitioned between EtOAc and saturated aq. NaHCO₃. The phases were separated and the organic phase was dried (MgSO₄) and concentrated in vacuo. The crude solid was purified by flash chromatography to give the corresponding oxazole or thiazole derivative.

Intermediate-9

(2-Acetyl-4-bromophenoxy)acetic acid ethyl ester Prepared from 5'-bromo-2'-hydroxyacetophenone (2 g, 9.3 mmol) and ethyl bromoacetate (1.03 mL, 9.3 mmol) according to GP2 to give the title compound as a white solid (2.64 g, 8.7 mmol, 94%): LC/MS (an10p8) Rt 3.3 min, m/z 301 [M+H]⁺; ¹H NMR (CDCl₃): δ 1.32 (t, 3H), 2.71 (s, 3H), 4.30 (q, 2H), 4.72 (s, 2H), 6.76 (d, 1H), 7.55 (dd, 1H), 7.88 (s, 1H).

Intermediate-10

[4-Bromo-2-(2-bromoacetyl)phenoxy]acetic acid ethyl ester. To a cooled (0° C.) solution of (2-acetyl-4-bromophenoxy)acetic acid ethyl ester (2.5 g, 8.3 mmol) in CHCl₃ (25 mL) was slowly added bromine (425 uL, 8.3 mmol). After completion the reaction mixture was allowed to stir at room temperature for 1 hour. The mixture was partitioned between CH$_2$Cl$_2$ and brine. The organic phase was washed with brine, dried (MgSO$_4$) and concentrated in vacuo to give the title compound as a white solid (2.97 g, 7.8 mmol, 94%): $^1$H NMR (CDCl$_3$): δ 1.35 (t, 3H), 4.32 (q, 2H), 4.75 (s, 2H), 4.76 (s, 2H), 6.77 (d, 1H), 7.60 (dd, 1H), 7.97 (s, 1H)

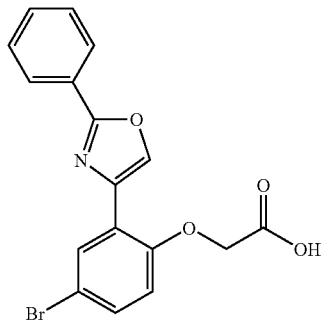

D83

[4-Bromo-2-(2-phenyloxazol-4-yl)phenoxy]acetic acid. Title compound was prepared from [4-bromo-2-(2-bromoacetyl)phenoxy]acetic acid ethyl ester and benzamide according to GP5 and GP3: LC/MS (an10p8) Rt 2.6 min, m/z 374/376 [M+H]$^+$.

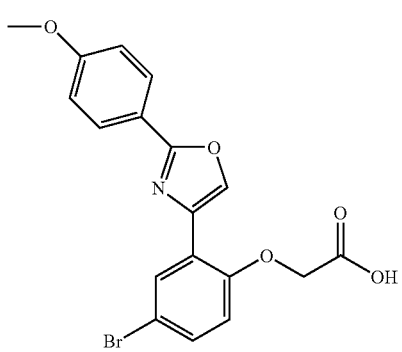

D84

{4-Bromo-2-[2-(4-methoxyphenyl)oxazol-4-yl]phenoxy}acetic acid. Title compound was prepared from [4-bromo-2-(2-bromoacetyl)phenoxy]acetic acid ethyl ester and 4-methoxybenzamide according to GP5 and GP3: LC/MS (an10p8) Rt 2.61 min, m/z 404 [M+H]$^+$.

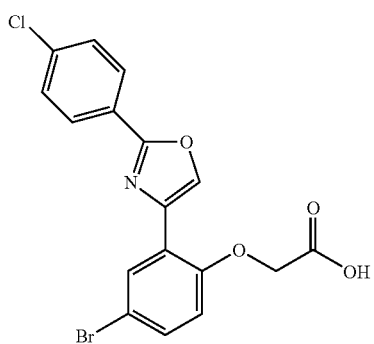

D85

{4-Bromo-2-[2-(4-chlorophenyl)oxazol-4-yl]phenoxy}acetic acid. Title compound was prepared from [4-bromo-2-(2-bromoacetyl)phenoxy]acetic acid ethyl ester and 4-chlorobenzamide according to GP5 and GP3: LC/MS (an10p8) Rt 2.90 min, m/z 407.7 [M+H]$^+$; $^1$H NMR (CDCl$_3$): δ 4.89 (s, 2H), 7.09 (d, 1H), 7.48 (d, 1H), 7.64 (d, 2H), 8.08 (d, 2H), 8.20 (s, 1H), 8.89 (s, 1H), 13.2 (br s, 1H).

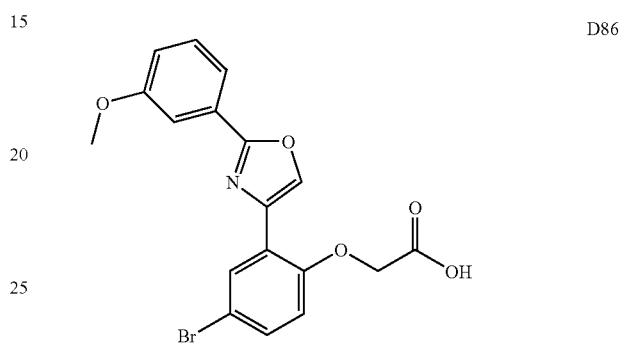

D86

{4-Bromo-2-[2-(3-methoxyphenyl)oxazol-4-yl]phenoxy}acetic acid. Title compound was prepared from [4-bromo-2-(2-bromoacetyl)phenoxy]acetic acid ethyl ester and 3-methoxybenzamide according to GP5 and GP3: LC/MS (an10p8) Rt 2.68 min, m/z 404 [M+H]$^+$; $^1$H NMR (CDCl$_3$): δ 3.87 (s, 1H), 4.89 (s, 2H), 7.09 (m, 2H), 7.4-7.7 (m, 4H), 8.22 (s, 1H), 8.89 (s, 1H), 13.3 (br s, 1H).

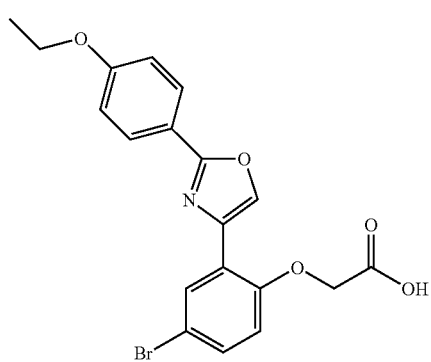

D87

{4-Bromo-2-[2-(4-ethoxyphenyl)oxazol-4-yl]phenoxy}acetic acid. Title compound was prepared from [4-bromo-2-(2-bromoacetyl)phenoxy]acetic acid ethyl ester and 4-ethylbenzamide according to GP5 and GP3: LC/MS (an10p8) Rt 2.80 min, m/z 418/420 [M+H]$^+$; $^1$H NMR (CDCl$_3$): δ 1.36 (t, 3H), 4.10 (q, 2H), 4.88 (s, 2H), 7.07 (m, 3H), 7.47 (d, 1H), 8.00 (d, 2H), 8.20 (s, 1H), 8.82 (s, 1H), 13.4 (br s, 1H).

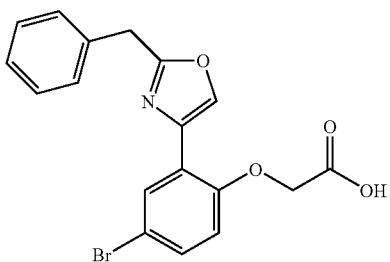

D88

[2-(2-Benzyloxazol-4-yl)-4-bromophenoxy]acetic acid. Title compound was prepared from [4-bromo-2-(2-bromoacetyl)phenoxy]acetic acid ethyl ester and 2-phenylacetamide according to GP5 and GP3: LC/MS (an10p8) Rt 2.47 min, m/z 388 [M+H]$^+$; $^1$H NMR (CDCl$_3$): δ 4.22 (s, 2H), 4.84 (s, 2H), 7.04 (d, 1H), 7.25 (m, 5H), 7.43 (d, 1H), 8.06 (s, 1H), 8.69 (s, 1H), 13 (br s, 1H).

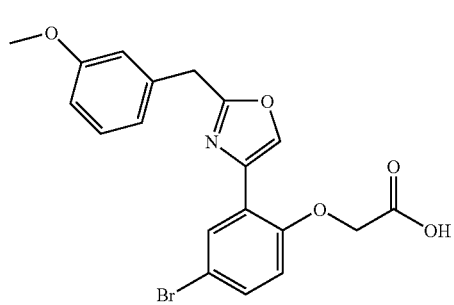

D89

{4-Bromo-2-[2-(3-methoxybenzyl)oxazol-4-yl]phenoxy}acetic acid. Title compound was prepared from [4-bromo-2-(2-bromoacetyl)phenoxy]acetic acid ethyl ester and 2-(3-methoxyphenyl)acetamide according to GP5 and GP3: LC/MS (an 10p8) Rt 2.45 min, m/z 418 [M+H]$^+$.

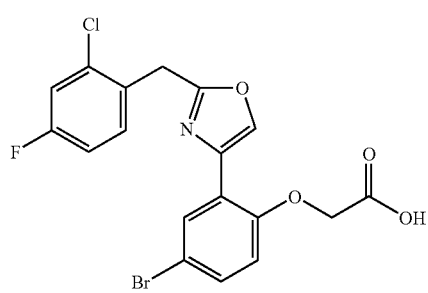

D90

{4-Bromo-2-[2-(2-chloro-4-fluorobenzyl)oxazol-4-yl]phenoxy}acetic acid. Title compound was prepared from [4-bromo-2-(2-bromoacetyl)phenoxy]acetic acid ethyl ester and 2-(2-chloro-4-fluorophenyl)acetamide according to GP5 and GP3: LC/MS (an 10p8) Rt 2.75 min, m/z 440 [M+H]$^+$.

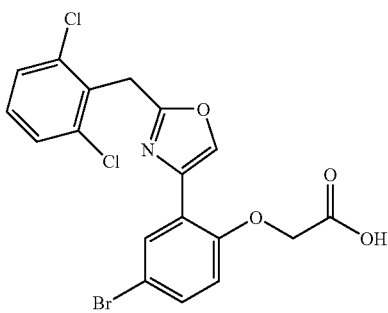

D91

{4-Bromo-2-[2-(2,6-dichlorobenzyl)oxazol-4-yl]phenoxy}acetic acid. Title compound was prepared from [4-bromo-2-(2-bromoacetyl)phenoxy]acetic acid ethyl ester and 2-(2,6-dichlorophenyl)acetamide according to GP5 and GP3: LC/MS (an 10p8) Rt 2.75 min, m/z 456/458/460 [M+H]$^+$.

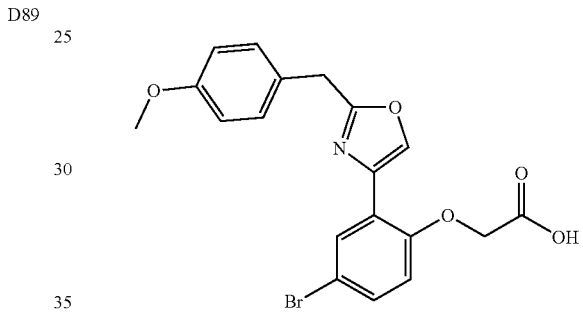

D92

{4-Bromo-2-[2-(4-methoxybenzyl)oxazol-4-yl]phenoxy}acetic acid. Title compound was prepared from [4-bromo-2-(2-bromoacetyl)phenoxy]acetic acid ethyl ester and 2-(4-methoxyphenyl)acetamide according to GP5 and GP3: LC/MS (an10p8) Rt 2.40 min, m/z 418 [M+H]$^+$; $^1$H NMR (CDCl$_3$): δ 3.72 (s, 3H), 4.14 (s, 1H), 4.85 (s, 1H), 6.92 (m, 2H), 7.02 (d, 1H), 7.2 (d, 1H), 7.23 (d, 1H), 7.44 (d, 1H), 8.05 (s, 1H), 8.67 (s, 1H), 13.2 (br s, 1H).

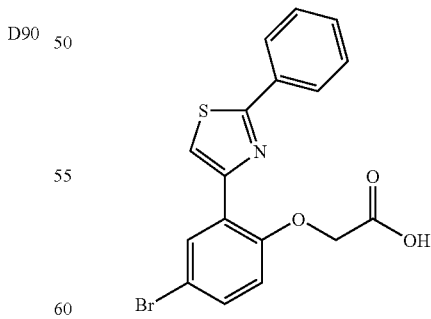

D93

[4-Bromo-2-(2-phenylthiazol-4-yl)phenoxy]acetic acid. Title compound was prepared from [4-bromo-2-(2-bromoacetyl)phenoxy]acetic acid ethyl ester and thiobenzamide according to GP5 and GP3: LC/MS (an10p8) Rt 2.69 min, m/z 390 [M+H]$^+$.

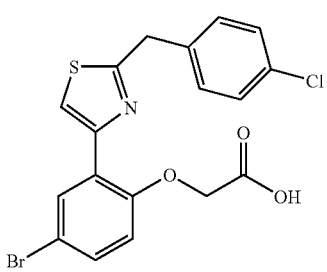

D94

{4-Bromo-2-[2-(4-chlorobenzyl)thiazol-4-yl]phenoxy}acetic acid Title compound was prepared from [4-bromo-2-(2-bromoacetyl)phenoxy]acetic acid ethyl ester and 2-(4-chlorophenyl)thioacetamide according to GP5 and GP3: LC/MS (an10p8) Rt 2.69 min, m/z 390 [M+H]$^+$; $^1$H NMR (CDCl$_3$): δ 4.42 (s, 2H), 4.86 (s, 2H), 7.06 (d, 1H), 7.45 (m, 5H), 8.33 (s, 1H), 8.41 (s, 1H), 13.2 (br s, 1H).

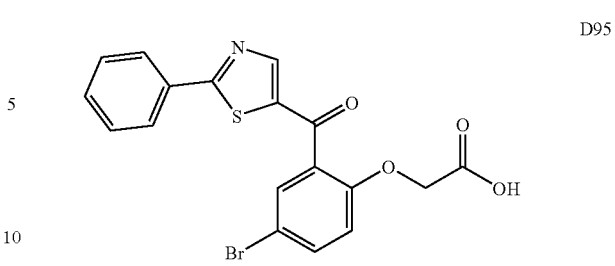

D95

[4-Bromo-2-(2-phenylthiazole-5-carbonyl)phenoxy]acetic acid. Title compound was prepared from [4-bromo-2-(2-bromoacetyl)phenoxy]acetic acid ethyl ester and thiobenzamide according to GP6 and GP3: LC/MS (an10p8) Rt 2.44 min, m/z 418 [M+H]$^+$.

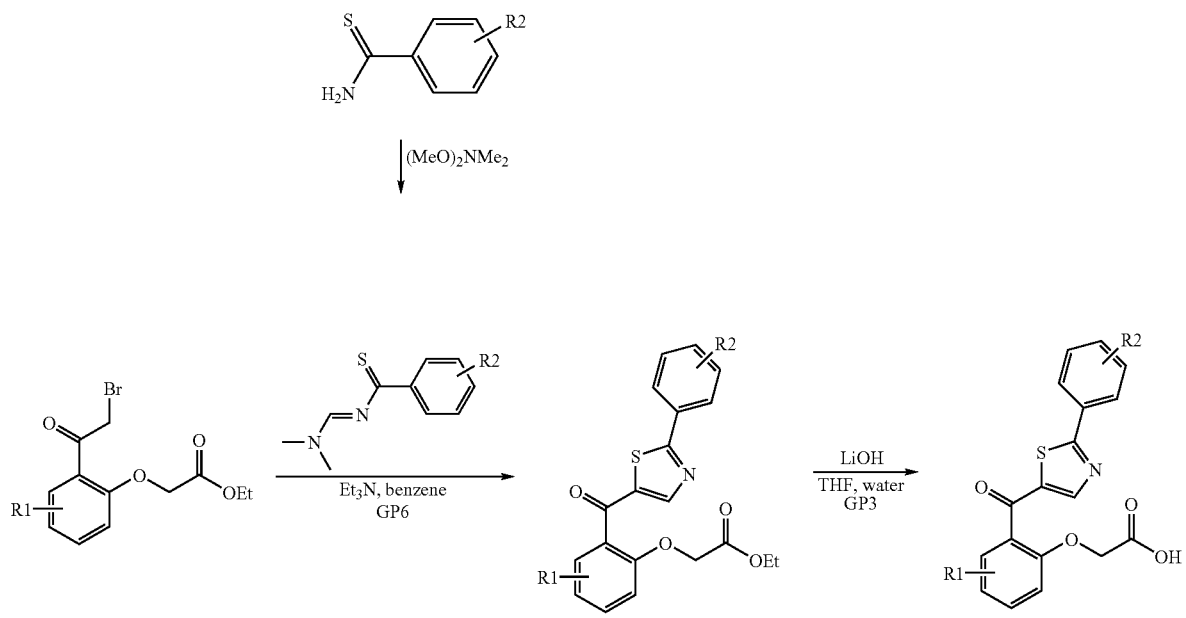

General synthetic route V

General Procedure 6 (GP6)

Synthesis of Carbonylthiazoles

A mixture of the thioamide (1.0 mmol) and N,N-dimethylformamide dimethylacetal (1.2 mmol) was stirred for 1 hour at room temperature under argon. The volatile materials were removed under reduced pressure without heating to give the corresponding N'-thioaroylformamidine which was used without further purification in the next step.

To a solution of the ethyl 2-(2-bromoacetyl)phenoxyacetate (1 mmol) and the N'-thioaroylformamidine (1 mmol) in benzene (2.6 mL) was added an excess of triethylamine (5 mmol). After stirring overnight at room temperature, solvent was removed in vacuo. The residue was partitioned between EtOAc and saturated aq. NaHCO$_3$. The organic phase was dried (MgSO$_4$) and concentrated in vacuo. The crude material was purified by flash chromatography to give the thioamide.

General synthetic route VI

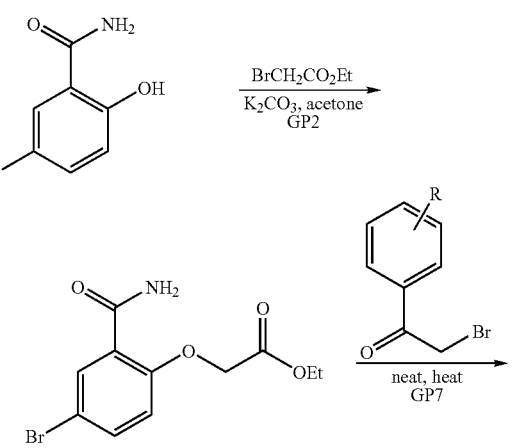

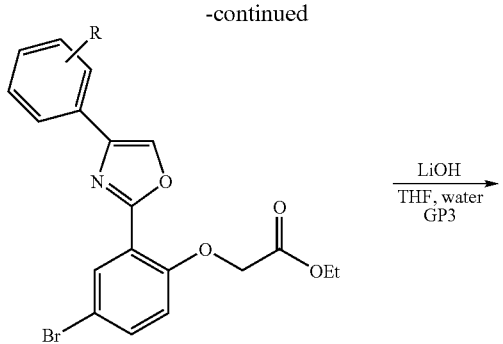

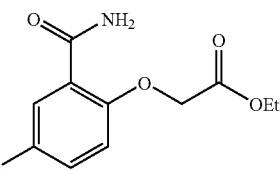

Intermediate-11

(4-Bromo-2-carbamoylphenoxy)acetic acid ethyl ester. Prepared from bromosalicylamide and ethyl bromoacetate according GP2: $^1$H NMR (CDCl$_3$): δ 1.35 (t, 3H), 4.34 (q, 2H), 4.73 (s, 2H), 5.87 (br s, 1H), 6.76 (d, 1H), 7.56 (d, 1H), 8.33 (br s, 1H), 8.39 (s, 1H).

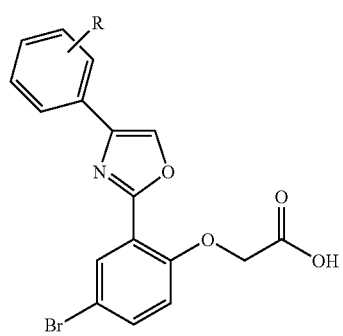

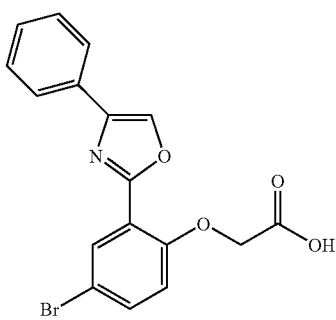

D96

General Procedure 7 (GP7)
Synthesis of Oxazole

A mixture of benzamide (1.0 mmol) and 2-bromoacetophenone (0.5 mmol) was heated neat in an Emrys Optimizer microwave oven for 3 hours at 140° C. After cooling EtOAc and CH$_2$Cl$_2$ were added and the formed precipitate was filtered off. The filtrate was concentrated in vacuo and purified by flash chromatography to give the corresponding oxazole.

[4-Bromo-2-(4-phenyl-oxazol-2-yl)-phenoxy]acetic acid. Title compound was prepared from (4-bromo-2-carbamoylphenoxy)acetic acid ethyl ester and 2-bromoacetophenone according to GP7: LC/MS (an 10p8) Rt 2.32 min, m/z 374/376 [M+H]$^+$.

General synthetic route VII

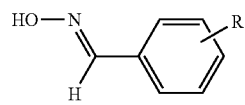

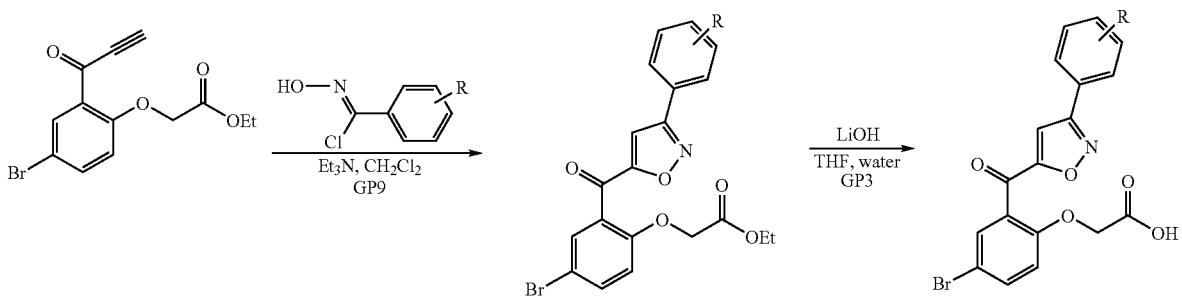

General Procedure 8 (GP8):
Synthesis of Hydroximic Acid Chloride

To a solution of the aldoxime (1.0 mmol) in $CH_2Cl_2$ (1.7 mL) was added N-chlorosuccinimide (1.0 mmol) in one portion. The reaction mixture was stirred for 3 hours at room temperature under an argon atmosphere. Water was added. The phases were separated. The organic phase was dried ($MgSO_4$) and concentrated in vacuo to give the corresponding hydroximic acid chloride derivative which was used without further purification.

General Procedure 9 (GP9):
Synthesis of Isoxazole

To a solution of the hydroximic acid chloride (1.0 mmol) and (4-bromo-2-propynoylphenoxy)acetic acid ethyl ester (1.0 mmol) in dry $CH_2Cl_2$ (3.7 mL) was slowly added a solution of $Et_3N$ (1.0 mmol) in dry $CH_2Cl_2$ (0.6 mL) over a period of 4 hours (use of syringe-pump). After completion of the addition, the reaction mixture was washed with water, brine, dried ($MgSO_4$) and concentrated in vacuo. The crude oil was purified by flash chromatography to give the corresponding isoxazol derivative.

the reaction mixture followed by $Et_2O$ (40 mL). The quenched reaction mixture was allowed to warm up to room temperature. The phases were separated and the aqueous phase was extracted with $Et_2O$ (2×). The combined organic phases were washed with brine, dried ($MgSO_4$) and concentrated in vacuo. The crude oil was purified by column chromatography ($SiO_2$), then was stirred for 90 min with polystyrene-supported trisamine (PS-Trisamine, 4.17 mmol/g, 8 g) in $CH_2Cl_2$ (160 mL). The resin was filtered off and the filtrate was concentrated in vacuo to give the title compound as pale yellow oil (7.6 g, 19.7 mmol, 54%). LC/MS (an10p8) Rt 4.30 min, m/z 408 [M+Na]$^+$; $^1$H NMR (CDCl$_3$): δ 0.24 (s, 9H), 1.31 (t, 3H), 4.27 (q, 2H), 4.71 (s, 2H), 5.79 (s, 1H), 6.74 (d, 1H), 7.39 (dd, 1H), 7.79 (d, 1H).

[4-Bromo-2-(3-trimethylsilanylpropynoyl)phenoxy]acetic acid ethyl ester. To a solution of [4-bromo-2-(1-hydroxy-3-trimethylsilanylprop-2-ynyl)phenoxy]acetic acid ethyl ester (0.95 g, 2.46 mmol) in $CH_2Cl_2$ (10 mL) was added activated $MnO_2$ in 2 portions (1.5 g+1 g), and the reaction was stirred for 90 min. The solid was filtered off through a celite pad and the filtrate was concentrated in vacuo to give the title Synthesis of Intermediate-12

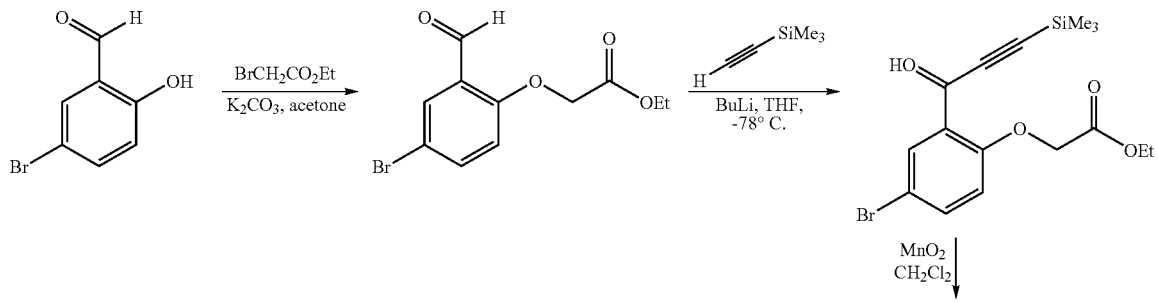

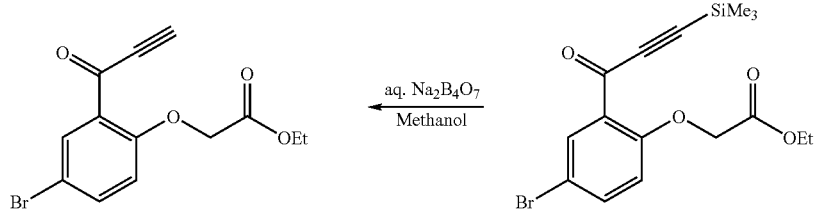

(4-Bromo-2-formylphenoxy)acetic acid ethyl ester. Prepared from 5-bromo-2-hydroxybenzaldehyde according GP2: LC/MS (an10p8) Rt 3.45 min, m/z 287 [M+H]$^+$; $^1$H NMR (CDCl$_3$): δ 1.29 (t, 3H), 4.25 (q, 2H), 4.74 (s, 2H), 6.79 (d, 1H), 7.60 (d, 1H), 7.94 (s, 1H), 10.46 (s, 1H)

[4-Bromo-2-(1-hydroxy-3-trimethylsilanylprop-2-ynyl)phenoxy]acetic acid ethyl ester. To a cooled (−78° C.) solution of (trimethylsilyl)acetylene (3.93 g, 40.0 mmol) in dry THF (40 mL) was slowly added a 2.5 M solution of butyllithium in hexanes (14.54 mL, 36.36 mmol). After stirring for 30 minutes at −78° C., the mixture was transferred to a cooled (−78° C.) solution of (4-bromo-2-formylphenoxy)acetic acid ethyl ester (10.44 g, 36.36 mmol) in dry THF (120 mL). Upon completion, the reaction mixture was stirred at −78° C. for 45 minutes. Saturated aq. $NH_4Cl$ (40 mL) was slowly added to compound as yellow oil (0.83 g, 2.16 mmol, 87%). LC/MS (an 10p8) Rt 4.70 min, m/z 383 [M+H]$^+$; $^1$H NMR (CDCl$_3$): δ 0.30 (s, 9H), 1.30 (t, 3H), 4.27 (q, 2H), 4.72 (s, 2H), 6.81 (d, 1H), 7.58 (dd, 1H), 8.10 (s, 1H).

(4-Bromo-2-propynoylphenoxy)acetic acid ethyl ester. To a solution of [4-bromo-2-(3-trimethylsilanylpropynoyl)phenoxy]acetic acid ethyl ester (0.83 g, 2.16 mmol) in methanol (20 mL) was added a 0.1M aqueous solution of $Na_2B_4O_7$ (10 mL). After stirring for 2-3 minutes at room temperature, $Et_2O$ and 1N aq. HCl were added. The phases were separated, and the organic phase was washed with brine, dried ($MgSO_4$) and concentrated in vacuo to give the title compound as yellow oil which crystallized upon standing (0.65 g, 2.09 mmol, 96%). LC/MS (an 10p8) Rt 3.58 min, m/z 311 [M+H]$^+$; $^1$H NMR (CDCl$_3$): δ1.31 (t, 3H), 3.45 (s, 1H), 4.27 (q, 2H), 4.74 (s, 2H), 6.83 (d, 1H), 7.61 (dd, 1H), 8.14 (d, 1H).

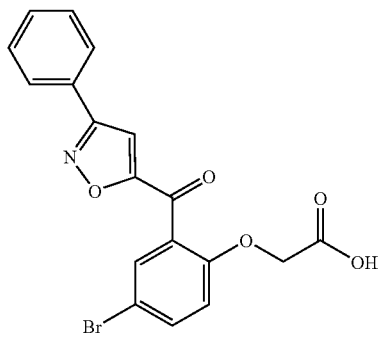

D97

[4-Bromo-2-(3-phenylisoxazole-5-carbonyl)phenoxy] acetic acid Title compound was prepared from benzaldoxime and (4-bromo-2-propynoylphenoxy)acetic acid ethyl ester according to GP8 and GP9: LC/MS (an10n8) Rt 3.07 min, m/z 400 [M−H]−; $^1$H NMR (DMSO): δ 4.77 (s, 2H), 7.13 (d, 1H), 7.53 (m, 3H), 7.73-7.92 (m, 5H).

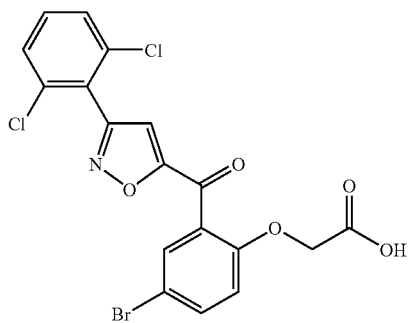

D98

{4-Bromo-2-[3-(2,6-dichloro-phenyl)isoxazole-5-carbonyl]phenoxy}acetic acid. Title compound was prepared from 2,6-dichlorobenzalddoxime and (4-bromo-2-propynoylphenoxy)acetic acid ethyl ester according to GP8 and GP9: LC/MS (an10n8) Rt 2.74 min, m/z 471.9 [M+H]+.

General Synthetic Route VIII

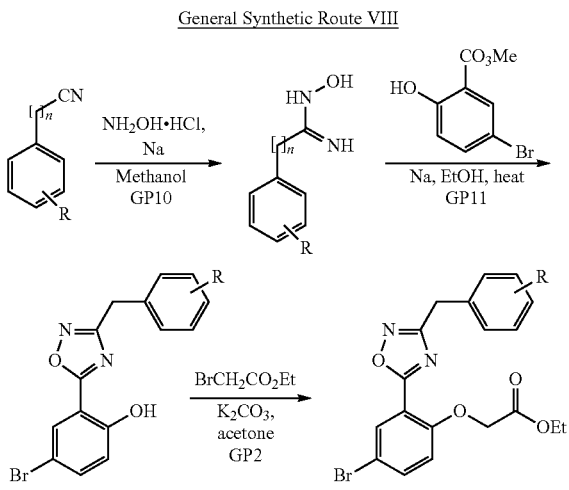

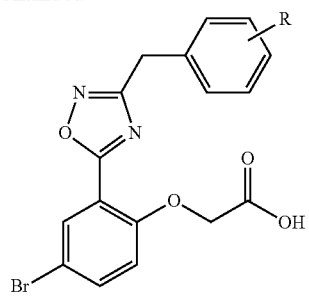

General Procedure 10 (GP10)

Synthesis of Amidoximes

Sodium (1.25 mmol) was added to dry methanol (1 ml) to give solution A. Hydroxylamine hydrochloride (1.2 mmol) was dissolved in dry methanol (1 mL) to give solution B. Solution A and B were mixed, cooled in an ice-bath and filtered. To the filtrate was then added the nitrile (1 mmol) and the reaction mixture was stirred over night at room temperature. The solvent was removed in vacuo to give the corresponding amidoxime. The compound was purified over silica gel chromatography (EtOAc/Heptane: 1/2) or used without further purification.

General Procedure 11 (GP11)

Synthesis of Oxadiazoles

To a solution of sodium (3.3 mmol) in dry ethanol (10 mL) were successively added the amidoxime (1.15 mmol), molecular sieves (1 g) and methyl benzoate (1 mmol). After stirring for 12 h under reflux, the reaction mixture was cooled and filtered through a celite pad. The celite pad was washed with methanol and $CH_2Cl_2$. The solvent was removed in vacuo and the residue was stirred with water. The precipitate was filtered off and dried to give the corresponding oxadiazole. The compound was purified over silica gel chromatography (EtOAc:Heptane, 1:2) or used without further purification in.

D99

[4-Bromo-2-(3-phenyl-[1,2,4]oxadiazol-5-yl)phenoxy] acetic acid. Title compound was prepared from 5-bromo-2-hydroxybenzoic acid methyl ester and benzonitrile according to GP10, GP11, GP2 and GP3: LC/MS (an10n8): Rt 2.41 min, m/z 373.4 [M−H]−; $^1$H NMR (DMSO-$d_6$): δ 4.97 (s, 2H), 7.2 (d, 1H), 7.62 (s, 3H), 7.82 (d, 2H), 8.10 (d, 1H), 8.2 (s, 1H).

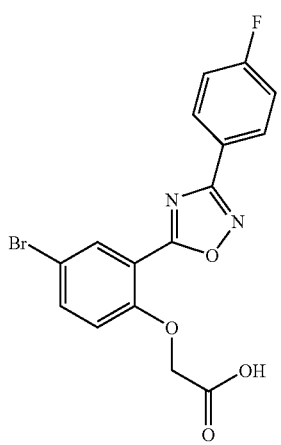

{4-Bromo-2-[3-(4-fluoro-phenyl)-[1,2,4]oxadiazol-5-yl]phenoxy}acetic acid. Title compound was prepared from 5-bromo-2-hydroxybenzoic acid methyl ester and 4-fluorobenzonitrile according to GP10, GP11, GP2 and GP3: LC/MS (an10n8) Rt 2.49, m/z 391.4 [M−H]−.

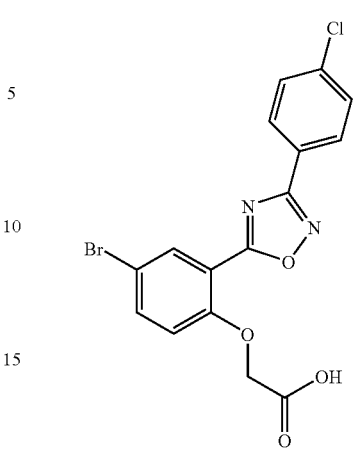

{4-Bromo-2-[3-(4-chlorophenyl)-[1,2,4]oxadiazol-5-yl]phenoxy}acetic acid. Title compound was prepared from 5-bromo-2-hydroxybenzoic acid methyl ester and 4-chlorobenzonitrile according to GP10, GP11, GP2 and GP3: LC/MS (an10n8) Rt 2.68 min, m/z 407.4 [M−H]−.

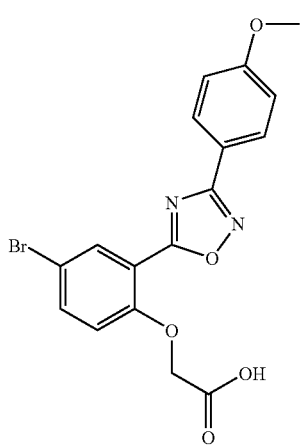

{4-Bromo-2-[3-(4-methoxy-phenyl)-[1,2,4]oxadiazol-5-yl]phenoxy}acetic acid. Title compound was prepared from 5-bromo-2-hydroxybenzoic acid methyl ester and 4-methoxybenzonitrile according to GP10, GP11, GP2 and GP3: LC/MS (an10n8) Rt 2.44 min, m/z 403.4 [M−H]−.

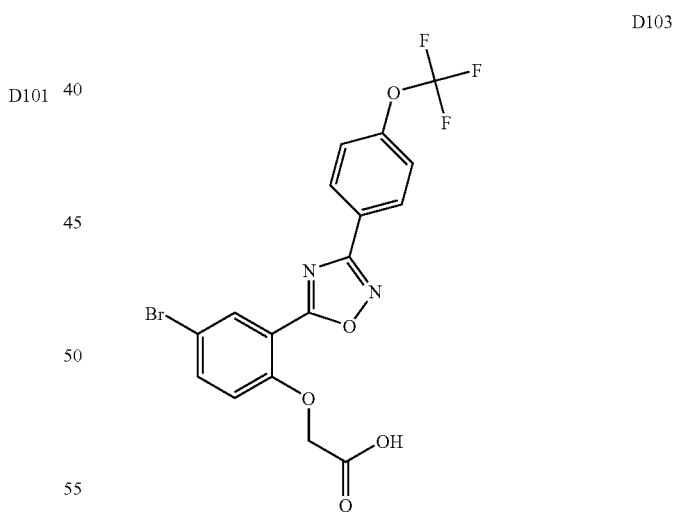

{4-Bromo-2-[3-(4-trifluoromethoxyphenyl)-[1,2,4]oxadiazol-5-yl]phenoxy}acetic acid. Title compound was prepared from 5-bromo-2-hydroxybenzoic acid methyl ester and 4-trifluoromethoxybenzonitrile according to GP10, GP11, GP2 and GP3: LC/MS (an10n8) Rt 2.09 min, m/z 457.5 [M−H]−; $^1$H NMR (DMSO-$d_6$): δ 4.96 (s, 2H), 7.21 (d, 1H), 7.59 (d, 2H), 7.82 (d, 1H), 8.22 (d, 3H).

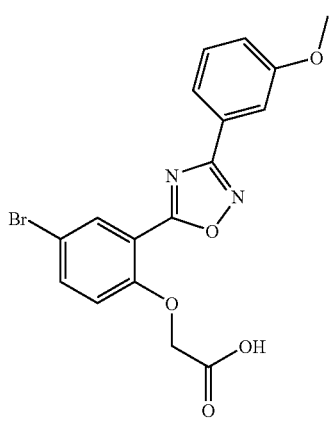

D104

{4-Bromo-2-[3-(3-methoxyphenyl)-[1,2,4]oxadiazol-5-yl]phenoxy}acetic acid. Title compound was prepared from 5-bromo-2-hydroxybenzoic acid methyl ester and 3-methoxybenzonitrile according to GP10, GP11, GP2 and GP3: LC/MS (an10n8) Rt 2.47 min, m/z 403.4 [M−H]−; $^1$H NMR (DMSO-d$_6$): δ 3.86 (s, 3H), 4.96 (s, 2H), 7.20 (d, 2H), 7.5 (t, 1H), 7.6 (s, 1H), 7.67 (d, 1H), 7.8 (d, 1H), 8.2 (s, 1H).

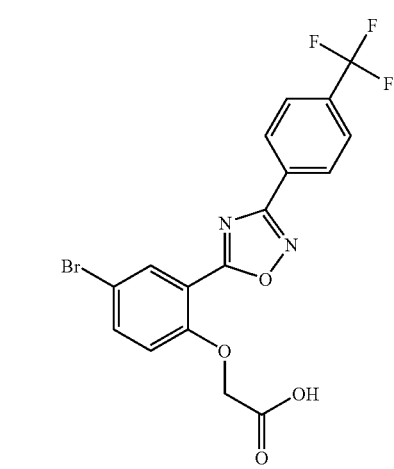

D106

{4-Bromo-2-[3-(4-trifluoromethyl-phenyl)-[1,2,4]oxadiazol-5-yl]phenoxy}-acetic acid. Title compound was prepared from 5-bromo-2-hydroxybenzoic acid methyl ester and 4-trifluoromethylbenzonitrile according to GP10, GP11, GP2 and GP3: LC/MS (an10n8) Rt 2.83 min, m/z 441.4 [M−H]−; $^1$H NMR (DMSO-d$_6$): δ 4.97 (s, 2H), 7.2 (d, 1H), 7.8 (dd, 1H), 7.9 (d, 2H), 8.2 (d, 1H), 8.3 (d, 2H).

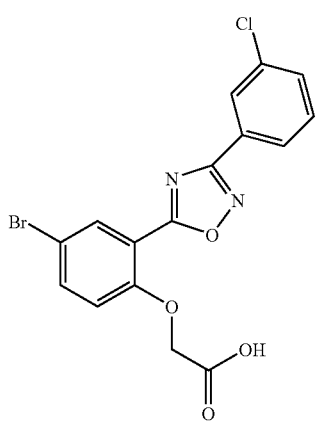

D105

{4-Bromo-2-[3-(3-chlorophenyl)-[1,2,4]oxadiazol-5-yl]phenoxy}acetic acid. Title compound was prepared from 5-bromo-2-hydroxybenzoic acid methyl ester and 3-chlorobenzonitrile according to GP10, GP11, GP2 and GP3: LC/MS (an10n8) Rt 2.69 min, m/z 407.4 [M−H]−; $^1$H NMR (DMSO): δ 4.97 (s, 2H), 7.2 (d, 1H), 7.6 (m, 2H), 7.7 (d, 1H), 7.8 (d 2H), 8.2, (s, 1H).

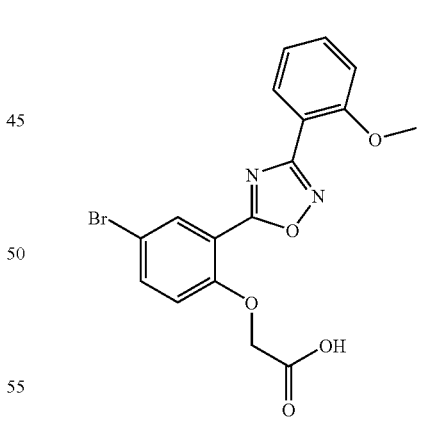

D107

{4-Bromo-2-[3-(2-methoxyphenyl)-[1,2,4]oxadiazol-5-yl]phenoxy}acetic acid. Title compound was prepared from 5-bromo-2-hydroxybenzoic acid methyl ester and 2-methoxybenzonitrile according to GP10, GP11, GP2 and GP3: LC/MS (an10n8) Rt 2.31 min, m/z 403.4 [M−H]−; $^1$H NMR (DMSO-d$_6$): δ 2.5 (s, 3H), 4.94 (s, 2H), 7.2 (m, 3H), 7.5 (t, 1H), 7.7 (d, 1H), 7.9 (d, 1H), 8.1 (s, 1H).

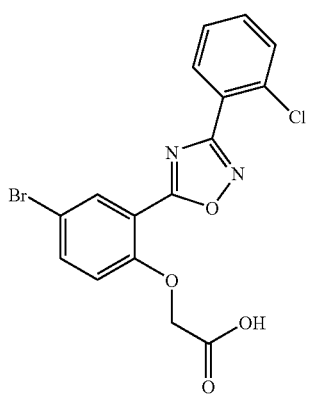

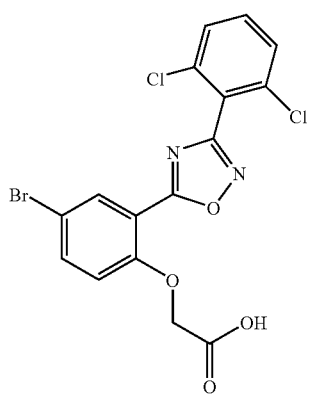

{4-Bromo-2-[3-(2-chlorophenyl)-[1,2,4]oxadiazol-5-yl]phenoxy}acetic acid. Title compound was prepared from 5-bromo-2-hydroxybenzoic acid methyl ester and 2-chlorobenzonitrile according to GP10, GP11, GP2 and GP3: LC/MS (an10n8) Rt 2.50 min, m/z 407.4 [M–H]$^-$; $^1$H NMR (DMSO-d$_6$): δ 4.94 (s, 2H), 7.2 (d, 1H), 7.5-7.7 (m, 3H), 7.8 (dd, 1H), 8.0 (d, 1H), 8.1 (s, 1H).

{4-Bromo-2-[3-(2,6-dichlorophenyl)-[1,2,4]oxadiazol-5-yl]phenoxy}acetic acid. Title compound was prepared from 5-bromo-2-hydroxybenzoic acid methyl ester and 2,6-Dichloro-benzonitrile according to GP10, GP11, GP2 and GP3: LC/MS (an10n8) Rt 2.59 min, m/z 441.4 [M–H]$^-$.

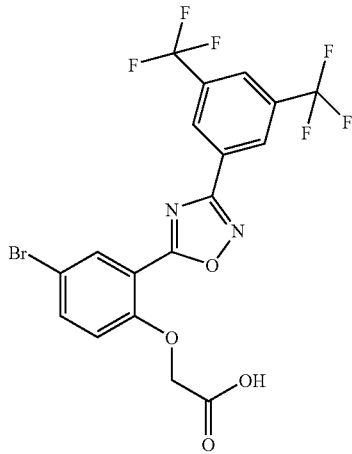

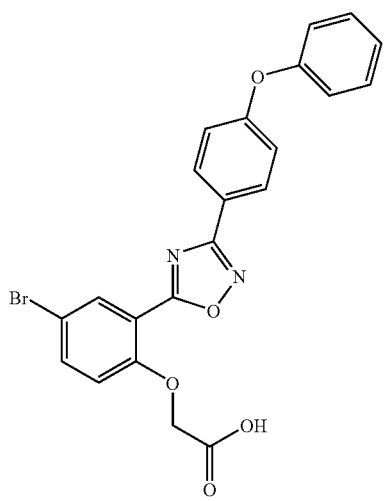

{2-[3-(3,5-Bis-trifluoromethyl-phenyl)-[1,2,4]oxadiazol-5-yl]-4-bromo-phenoxy}-acetic acid. Title compound was prepared from 5-bromo-2-hydroxybenzoic acid methyl ester and 3,5-bistrifluoromethoxybenzonitrile according to GP10, GP11, GP2 and GP3: LC/MS (an10n8) Rt 3.332 min, m/z 509.5 [M–H]$^-$; $^1$H NMR (DMSO-d$_6$): δ 4.96 (s, 2H), 7.2 (d, 1H), 7.8 (d, 1H), 8.2 (s, 1H), 8.4 (s, 1H), 8.5 (s, 1H), 8.6 (s, 1H).

{4-Bromo-2-[3-(4-phenoxy-phenyl)-[1,2,4]oxadiazol-5-yl]-phenoxy}-acetic acid. Title compound was prepared from 5-bromo-2-hydroxybenzoic acid methyl ester and 4-phenoxybenzonitrile according to GP10, GP11, GP2 and GP3: LC/MS (an10n8) Rt 3.29 min, m/z 465.5 [M–H]$^-$; $^1$H NMR (DMSO-d$_6$): δ 4.95 (s, 2H), 7.2 (m, 6H), 7.4 (t, 2H), 7.8 (d, 1H), 8.0 (d, 2H), 8.1 (s, 1H).

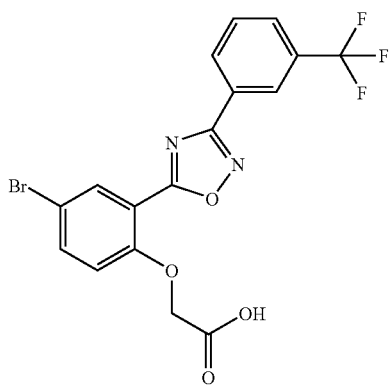

D112

{4-Bromo-2-[3-(3-trifluoromethylphenyl)-[1,2,4]oxadiazol-5-yl]phenoxy}-acetic acid. Title compound was prepared from 5-bromo-2-hydroxybenzoic acid methyl ester and 3-trifluoromethylbenzonitrile according to GP10, GP11, GP2 and GP3: LC/MS (an10n8) Rt 2.96 min, m/z 441.4 [M−H]−; $^1$H NMR (DMSO-$d_6$): δ 4.97 (s, 2H), 7.2 (d, 1H), 7.8 (m, 2H), 8.0 (d, 1H), 8.2 (s, 1H), 8.3 (s, 1H), 8.4 (d, 1H).

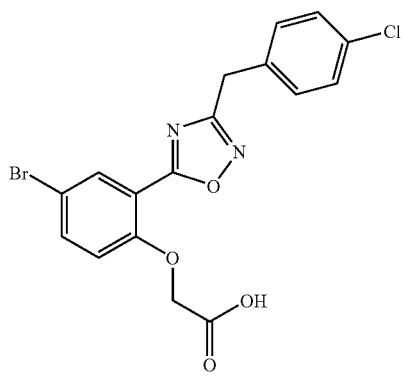

D114

{4-Bromo-2-[3-(4-chloro-benzyl)-[1,2,4]oxadiazol-5-yl]-phenoxy}-acetic acid. Title compound was prepared from 5-bromo-2-hydroxybenzoic acid methyl ester and (4-chlorophenyl)acetonitrile according to GP10, GP11, GP2 and GP3: LC/MS (an10n8) Rt 2.54 min, m/z 421.4 [M−H]−; $^1$H NMR (DMSO-$d_6$): δ 4.2 (s, 2H), 4.9 (s, 2H), 7.1 (d, 1H), 7.4 (s, 4H), 7.8 (d, 1H), 8.0 (s, 1H).

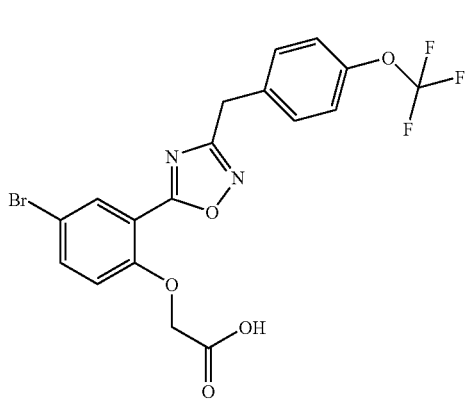

D113

{4-Bromo-2-[3-(4-trifluoromethoxy-benzyl)-[1,2,4]oxadiazol-5-yl]-phenoxy}-acetic acid. Title compound was prepared from 5-bromo-2-hydroxybenzoic acid methyl ester and (4-trifluoromethoxyphenyl)acetonitrile according to GP10, GP11, GP2 and GP3: LC/MS (an10n8) Rt 2.76 min, m/z 4715 [M−H]−; $^1$H NMR (DMSO-$d_6$): δ 4.2 (s, 2H), 4.9 (s, 2H), 7.1 (d, 1H), 7.3 (d, 2H), 7.5 (d, 2H), 7.7 (d, 1H), 8.0 (s, 1H).

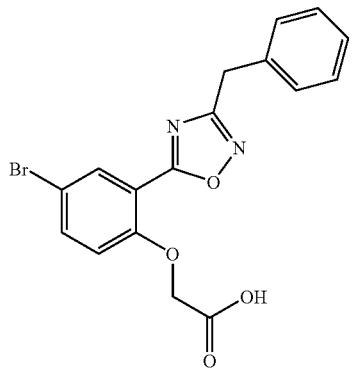

D115

[2-(3-Benzyl-[1,2,4]oxadiazol-5-yl)-4-bromo-phenoxy]-acetic acid. Title compound was prepared from 5-bromo-2-hydroxybenzoic acid methyl ester and phenylacetonitrile according to GP10, GP11, GP2 and GP3: LC/MS (an10n8) Rt 2.26 min, m/z 387.4 [M−H]−; $^1$H NMR (DMSO-$d_6$): δ 4.2 (s, 2H), 4.9 (s, 2H), 7.1 (d, 1H), 7.3 (m, 5H), 7.7 (d, 1H), 8.0 (s, 1H).

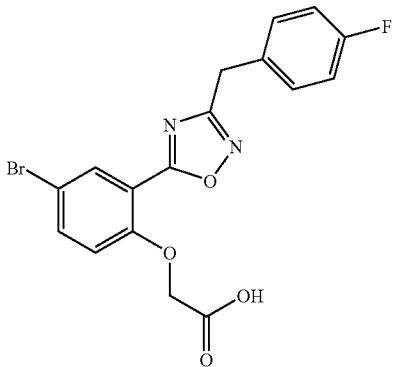

D116

{4-Bromo-2-[3-(4-fluoro-benzyl)-[1,2,4]oxadiazol-5-yl]-phenoxy}-acetic acid. Title compound was prepared from 5-bromo-2-hydroxybenzoic acid methyl ester and (4-fluorophenyl)acetonitrile according to GP10, GP11, GP2 and GP3: LC/MS (an10n8) Rt 2.38 min, m/z 405.4 [M−H]⁻.

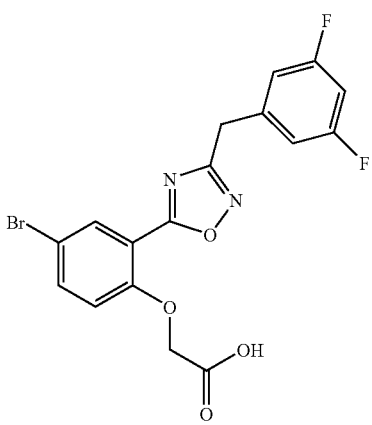

D117

{4-Bromo-2-[3-(3,5-difluoro-benzyl)-[1,2,4]oxadiazol-5-yl]-phenoxy}-acetic acid. Title compound was prepared from 5-bromo-2-hydroxybenzoic acid methyl ester and (3,5-difluorophenyl)acetonitrile according to GP10, GP11, GP2 and GP3: LC/MS (an10n8) Rt 2.44 min, m/z 423.4 [M−H]⁻.

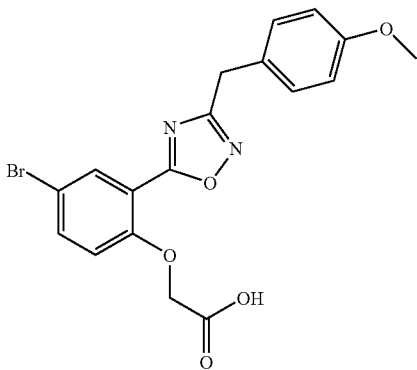

D118

{4-Bromo-2-[3-(4-methoxy-benzyl)-[1,2,4]oxadiazol-5-yl]-phenoxy}-acetic acid. Title compound was prepared from 5-bromo-2-hydroxybenzoic acid methyl ester and (4-methoxyphenyl)acetonitrile according to GP10, GP11, GP2 and GP3: LC/MS (an10n8) Rt 2.25 min, m/z 417.4 [M−H]⁻; ¹H NMR (DMSO-d₆): δ 4.1 (s, 2H), 4.9 (s, 2H), 6.9 (d, 2H), 7.1 (d, 1H), 7.2 (d, 2H), 7.7 (d, 1H), 8.0 (s, 1H).

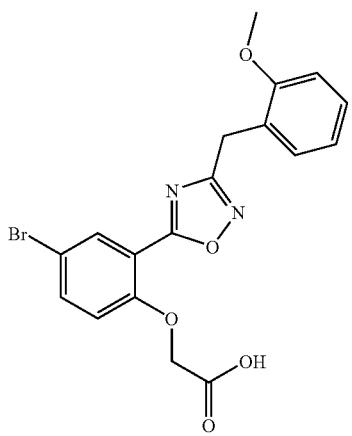

D119

{4-Bromo-2-[3-(2-methoxy-benzyl)-[1,2,4]oxadiazol-5-yl]-phenoxy}-acetic acid. Title compound was prepared from 5-bromo-2-hydroxybenzoic acid methyl ester and (2-Methoxy-phenyl)-acetonitrile according to GP10, GP11, GP2 and GP3: LC/MS (an10n8) Rt 2.25 min, m/z 417.4 [M−H]⁻; ¹H NMR (DMSO-d₆): δ 3.7 (s, 3H), 4.1 (s, 2H), 4.9 (s, 2H), 6.9 (t, 1H), 7.0 (d, 1H), 7.1 (d, 1H), 7.2 (m, 2H), 7.7 (d, 1H), 8.0 (s, 1H).

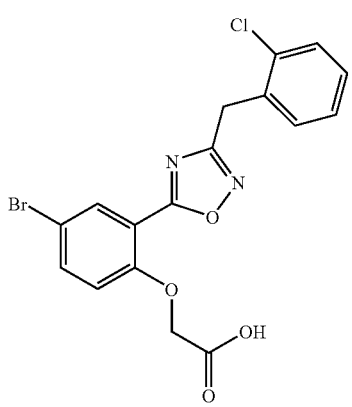

D120

{4-Bromo-2-[3-(2-chloro-benzyl)-[1,2,4]oxadiazol-5-yl]-phenoxy}-acetic acid. Title compound was prepared from 5-bromo-2-hydroxybenzoic acid methyl ester and (2-chlorophenyl)acetonitrile according to GP10, GP11, GP2 and GP3: LC/MS (an10n8) Rt 2.48 min, m/z 421.4 [M−H]⁻; ¹H NMR (DMSO-d₆): δ 4.2 (s, 2H), 4.9 (s, 2H), 7.1 (d, 1H), 7.3 (m, 2H), 7.4 (m, 2H), 7.7 (dd, 1H), 8.0 (d, 1H).

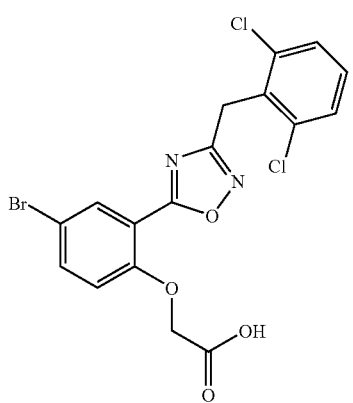

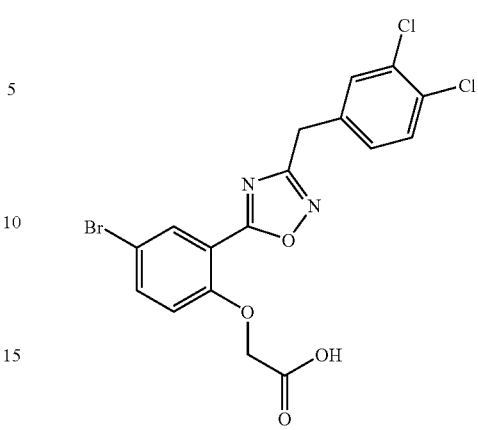

{4-Bromo-2-[3-(2,6-dichloro-benzyl)-[1,2,4]oxadiazol-5-yl]-phenoxy}-acetic acid. Title compound was prepared from 5-bromo-2-hydroxybenzoic acid methyl ester and (2,6-dichlorophenyl)acetonitrile according to GP10, GP11, GP2 and GP3: LC/MS (an10n8) Rt 2.58 min, m/z 455/457/459 [M−H]−; 1H NMR (DMSO-d6): δ 4.4 (s, 2H), 4.9 (s, 2H), 7.1 (d, 1H), 7.4 (t, 1H), 7.5 (d, 2H), 8.7-7.8 (dd, 1H), 8.0 (d, 1H).

{4-Bromo-2-[3-(3,4-dichlorobenzyl)-[1,2,4]oxadiazol-5-yl]-phenoxy}acetic acid. Title compound was prepared from 5-bromo-2-hydroxybenzoic acid methyl ester and (3,4-dichlorophenyl)acetonitrile according to GP10, GP11, GP2 and GP3: LC/MS (an10n8) Rt 2.81 min, m/z 455/457/459 [M−H]−; 1H NMR (DMSO-d6): δ 4.3 (s, 2H), 4.8 (s, 2H), 7.1 (d, 1H), 7.3 (dd, 1H), 7.6 (d, 1H), 7.6 (d, 1H), 7.7 (dd, 1H), 8.0 (d, 1H).

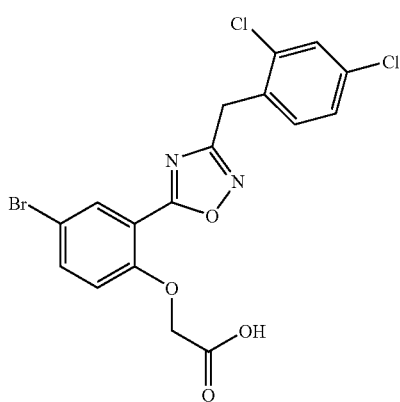

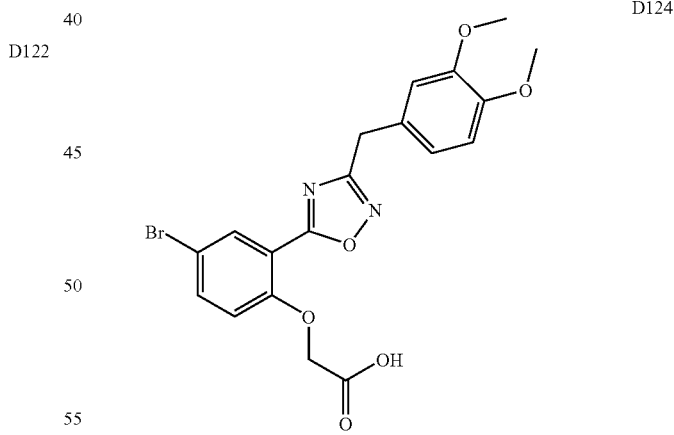

{4-Bromo-2-[3-(2,4-dichloro-benzyl)-[1,2,4]oxadiazol-5-yl]-phenoxy}-acetic acid. Title compound was prepared from 5-bromo-2-hydroxybenzoic acid methyl ester and (2,4-dichlorophenyl)acetonitrile according to GP10, GP11, GP2 and GP3: LC/MS (an10n8) Rt 2.78 min, m/z 455/457/459 [M−H]−.

{4-Bromo-2-[3-(3,4-dimethoxybenzyl)-[1,2,4]oxadiazol-5-yl]phenoxy}-acetic acid. Title compound was prepared from 5-bromo-2-hydroxybenzoic acid methyl ester and (3,4-bismethoxyphenyl)acetonitrile according to GP10, GP11, GP2 and GP3: LC/MS (an10n8) Rt 2.20 min, m/z 447.4 [M−H]−; 1H NMR (DMSO-d6): δ 3.72 (s, 3H), 3.74 (s, 3H), 4.1 (s, 2H), 4.9 (s, 2H), 6.8 (m, 2H), 6.9 (s, 1H), 7.1 (d, 1H), 7.7 (dd, 1H), 8.0 (d, 1H).

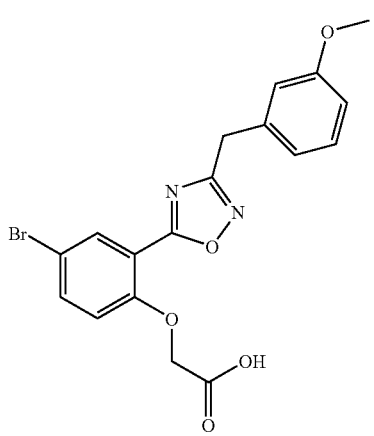

{4-Bromo-2-[3-(3-methoxybenzyl)-[1,2,4]oxadiazol-5-yl]phenoxy}acetic acid. Title compound was prepared from 5-bromo-2-hydroxybenzoic acid methyl ester and (3-methoxyphenyl)acetonitrile according to GP10, GP11, GP2 and GP3: LC/MS (an10n8) Rt 2.38 min, m/z 417.4 [M–H]⁻; ¹H NMR (DMSO-d₆): δ 4.1 (s, 2H), 4.9 (s, 2H), 6.8 (d, 1H), 6.9 (m, 2H), 7.1 (d, 1H), 7.2 (t, 1H), 7:8 (m, 1H), 8.0 (d, 1H).

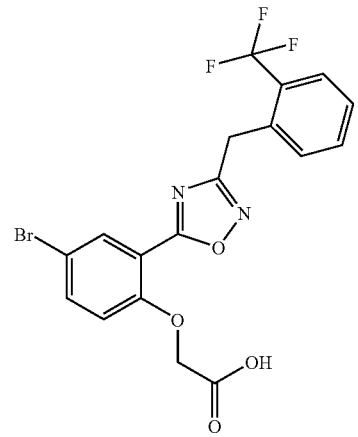

{4-Bromo-2-[3-(2-trifluoromethylbenzyl)-[1,2,4]oxadiazol-5-yl]phenoxy}-acetic acid. Title compound was prepared from 5-bromo-2-hydroxybenzoic acid methyl ester and (2-trifluoromethylphenyl)acetonitrile according to GP10, GP11, GP2 and GP3: LC/MS (an10n8) Rt 2.77 min, m/z 455.5 [M–H]⁻; ¹H NMR (DMSO-d₆): δ 4.3 (s, 2H), 4.9 (s, 2H), 7.1 (d, 1H), 7.5-7.6 (m, 2H), 7:6-7.7 (t, 1H), 7.7-7.8 (m, 2H), 8.0 (d, 1H).

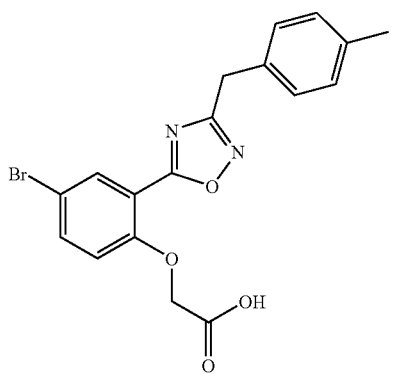

{4-Bromo-2-[3-(4-methylbenzyl)-[1,2,4]oxadiazol-5-yl]phenoxy}acetic acid. Title compound was prepared from 5-bromo-2-hydroxybenzoic acid methyl ester and (4-methylphenyl)acetonitrile according to GP10, GP11, GP2 and GP3: LC/MS (an10n8) Rt 2.72 min, m/z 401.4 [M–H]⁻; ¹H NMR (DMSO-d₆): δ 3.3 (s, 3H), 4.1 (s, 2H), 4.9 (s, 2H), 7.1 (m, 3H), 7.2 (d, 2H), 7.7 (dd, 1H), 8.0 (d, 1H).

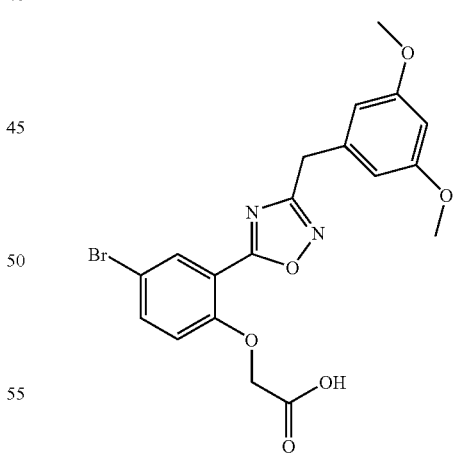

{4-Bromo-2-[3-(3,5-dimethoxybenzyl)-[1,2,4]oxadiazol-5-yl]phenoxy}acetic acid. Title compound was prepared from 5-bromo-2-hydroxybenzoic acid methyl ester and (3,5-bismethoxyphenyl)acetonitrile according to GP10, GP11, GP2 and GP3: LC/MS (an10n8) Rt 2.61 min, m/z 447.4 [M–H]⁻; ¹H NMR (DMSO-d₆): δ 3.7 (s, 6H), 4.1 (s, 2H), 4.9 (s, 2H), 6.4 (d, 1H), 6.5 (d, 2H), 7.1 (d, 1H), 7.8 (dd, 1H), 8.0 (d, 1H).

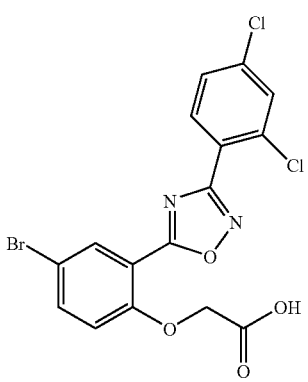

D129

{4-Bromo-2-[3-(2,4-dichlorophenyl)-[1,2,4]oxadiazol-5-yl]phenoxy}acetic acid. Title compound was prepared from 5-bromo-2-hydroxy-benzoic acid methyl ester and 2,4-dichlorobenzonitrile according to GP10, GP11, GP2 and GP3: LC/MS (an10n8) Rt 2.93 m/z 441/443/445 [M–H]⁻; $^1$H NMR (DMSO): δ 4.7 (s, 1H), 6.95-6.98 (d, 1H), 7.42-7.44 (d, 1H), 7.58-7.60 (d, 1H), 7.67 (s, 1H), 7.82-7.85 (d, 1H), 7.94-7.95 (s, 1H).

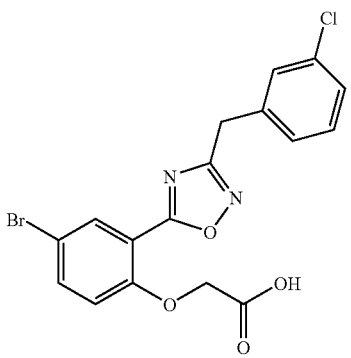

D130

{4-Bromo-2-[3-(3-chlorobenzyl)-[1,2,4]oxadiazol-5-yl]phenoxy}acetic acid. Title compound was prepared from 5-bromo-2-hydroxy-benzoic acid methyl ester and 3-chlorophenylacetonitrile according to GP10, GP11, GP2 and GP3: LC/MS (an10n8) Rt 2.79 m/z 421.4 [M–H]⁻; $^1$H NMR (DMSO): δ 4.21 (s, 2H), 4.92 (s, 2H), 7.15-7.18 (d, 1H), 7.32-7.39 (m, 3H), 7.45 (s, 1H), 7.76-7.80 (dd, 1H), 8.03-8.04 (d, 1H).

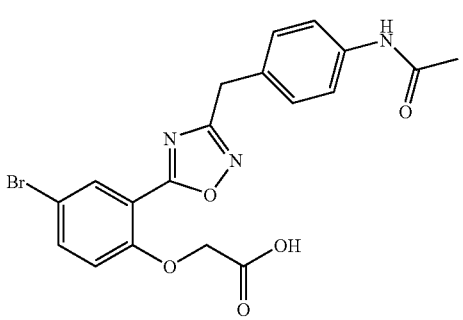

D131

{2-[3-(4-Acetylaminobenzyl)-[1,2,4]oxadiazol-5-yl]-4-bromophenoxy}acetic acid. Title compound was prepared from 5-bromo-2-hydroxybenzoic acid methyl ester and 4-acetamidophenylacetonitrile according to GP10, GP11, GP2 and GP3: LC/MS (an10n8) Rt 2.15 m/z 444.4 [M–H]⁻; $^1$H NMR (DMSO): δ 2.02 (s, 3H), 4.10 (s, 2H), 4.92 (s, 2H), 7.14-7.17 (d, 1H), 7.25-7.27 (d, 2H), 7.52-7.54 (d, 2H), 7.76-7.78 (d, 1H), 8.03 (s, 1H).

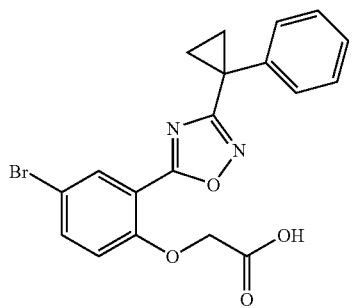

D132

{4-Bromo-2-[3-(1-phenylcyclopropyl)-[1,2,4]oxadiazol-5-yl]phenoxy}acetic acid. Title compound was prepared from 5-bromo-2-hydroxy-benzoic acid methyl ester and 1-phenyl-1-cyclopropanecarbonitrile according to GP10, GP11, GP2 and GP3: LC/MS (an10n8) Rt. 2.756 m/z 413.4 [M–H]⁻; $^1$H NMR (DMSO-d$_6$): δ 0.92 (m, 2H), 1.11 (m, 2H), 4.38 (s, 2H), 6.63-6.66 (d, 1H), 6.79-6.88 (m, 3H), 6.93-6.95 (m, 2H), 7.25-7.29 (dd, 1H), 7.50-7.51 (d, 1H).

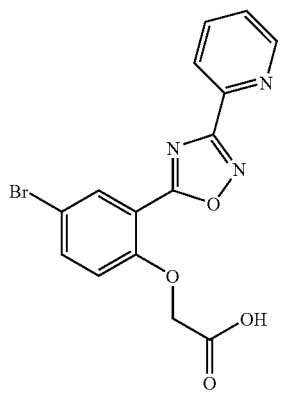

D133

[4-Bromo-2-(3-pyridin-2-yl-[1,2,4]oxadiazol-5-yl)phenoxy]acetic acid. Title compound was prepared from 5-bromo-2-hydroxybenzoic acid methyl ester and Pyridine-2-carbonitrile according to GP10, GP11, GP2 and GP3: LC/MS (an10n8) Rt 1.89 min, m/z 374.4 [M–H]⁻; $^1$H NMR (DMSO-d$_6$): δ 4.9 (s, 2H), 7.2 (d, 1H), 7.6 (m, 1H), 7.8 (d, 1H), 8.0 (t, 1H), 8.2 (m, 2H), 8.8 (d, 1H).

General Synthetic route IX

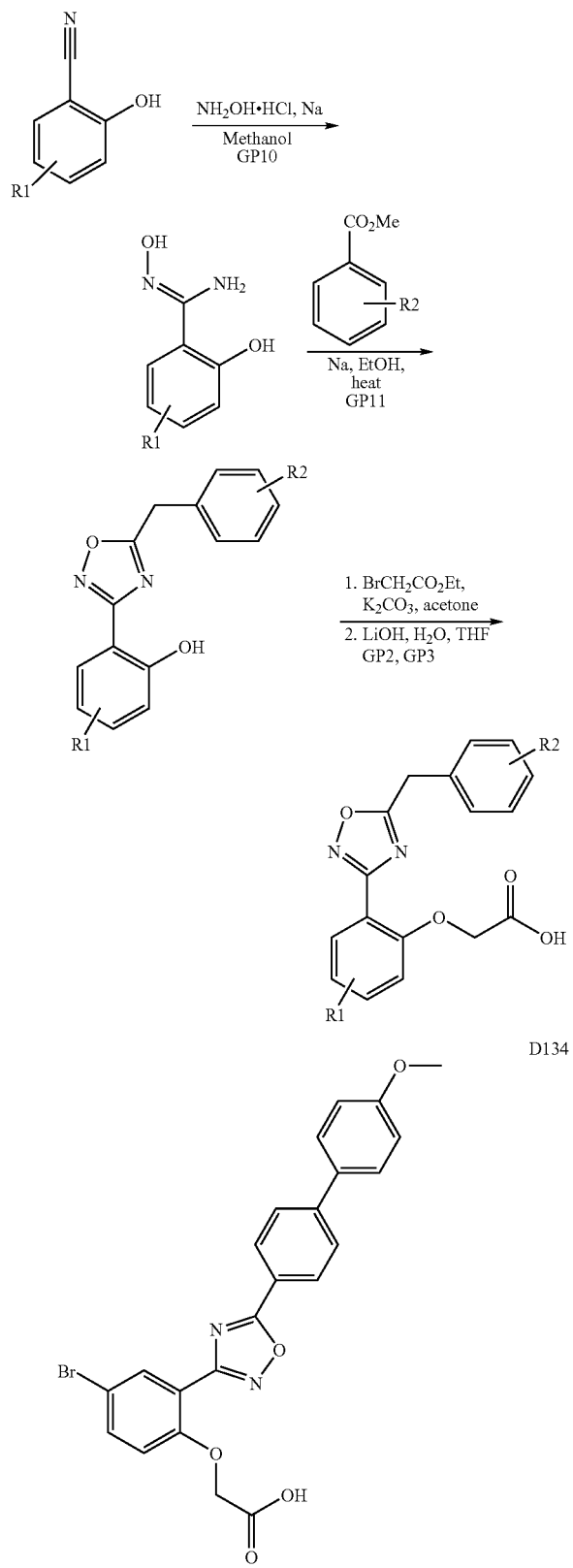

D134

{4-Bromo-2-[5-(4'-methoxybiphenyl-4-yl)-[1,2,4]oxadiazol-3-yl]phenoxy}acetic acid. Title compound was prepared from 2-hydroxy-5-bromo-benzonitrile and 4'-methoxy-biphenyl-4-carboxylic acid methyl ester according to GP10, GP11, GP2 and GP3: LC/MS (an10n8) Rt 2.96 min, m/z 479.5 [M–H]⁻.

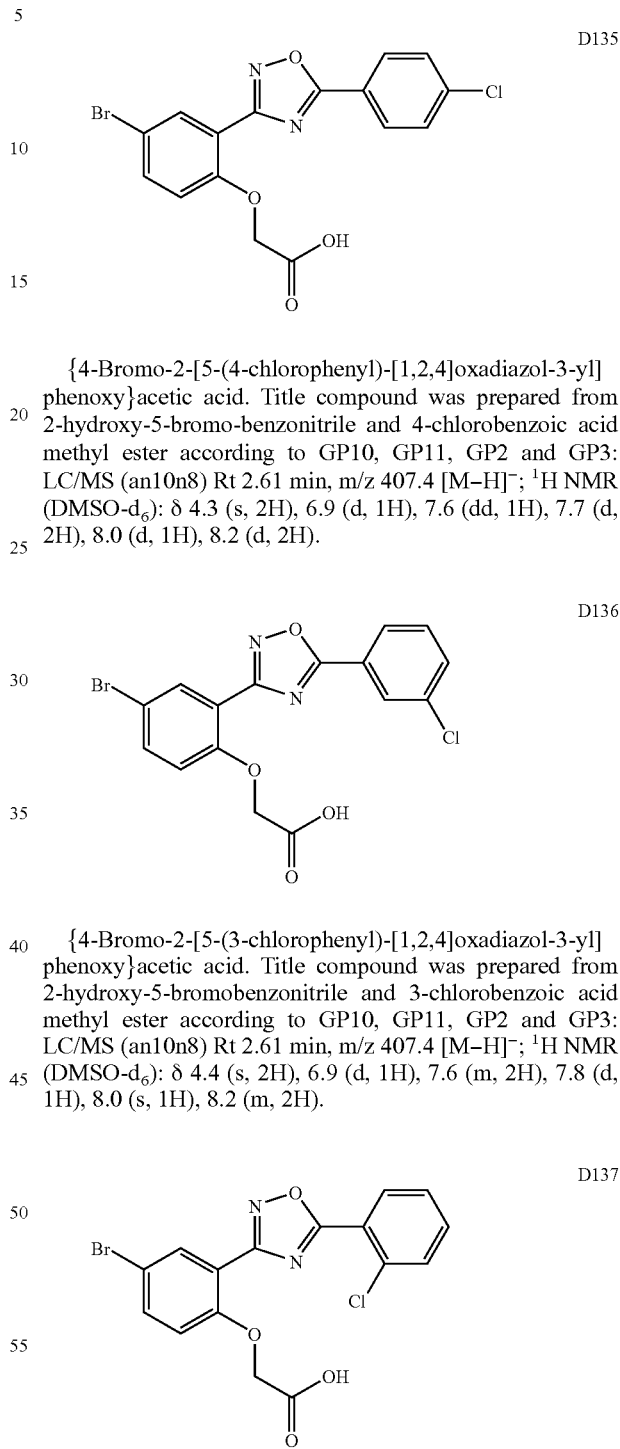

{4-Bromo-2-[5-(4-chlorophenyl)-[1,2,4]oxadiazol-3-yl]phenoxy}acetic acid. Title compound was prepared from 2-hydroxy-5-bromo-benzonitrile and 4-chlorobenzoic acid methyl ester according to GP10, GP11, GP2 and GP3: LC/MS (an10n8) Rt 2.61 min, m/z 407.4 [M–H]⁻; $^1$H NMR (DMSO-$d_6$): δ 4.3 (s, 2H), 6.9 (d, 1H), 7.6 (dd, 1H), 7.7 (d, 2H), 8.0 (d, 1H), 8.2 (d, 2H).

{4-Bromo-2-[5-(3-chlorophenyl)-[1,2,4]oxadiazol-3-yl]phenoxy}acetic acid. Title compound was prepared from 2-hydroxy-5-bromobenzonitrile and 3-chlorobenzoic acid methyl ester according to GP10, GP11, GP2 and GP3: LC/MS (an10n8) Rt 2.61 min, m/z 407.4 [M–H]⁻; $^1$H NMR (DMSO-$d_6$): δ 4.4 (s, 2H), 6.9 (d, 1H), 7.6 (m, 2H), 7.8 (d, 1H), 8.0 (s, 1H), 8.2 (m, 2H).

{4-Bromo-2-[5-(2-chlorophenyl)-[1,2,4]oxadiazol-3-yl]phenoxy}acetic acid. Title compound was prepared from 2-hydroxy-5-bromobenzonitrile and 2-chlorobenzoic acid methyl ester according to GP10, GP11, GP2 and GP3: LC/MS (an10n8) Rt 2.45 min, m/z 407.4 [M–H]⁻; $^1$H NMR (DMSO-$d_6$): δ 4.3 (s, 2H), 6.9 (d, 1H) 7.6-7.7 (m, 4H), 8.0 (s, 1H), 8.2 (d, 1H).

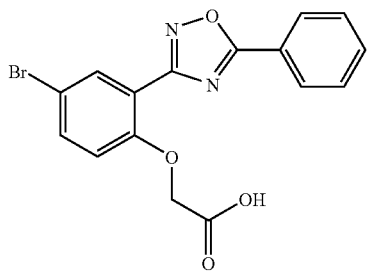

D138

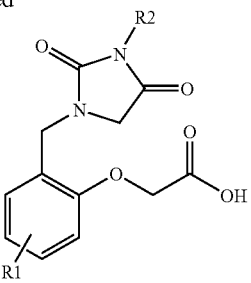

[4-Bromo-2-(5-phenyl-[1,2,4]oxadiazol-3-yl)phenoxy]acetic acid. Title compound was prepared from 2-hydroxy-5-bromobenzonitrile and benzoic acid methyl ester according to GP10, GP11, GP2 and GP3: LC/MS (an10n8) Rt 2.33 min, m/z 373.4 [M−H]$^-$; $^1$H NMR (DMSO-d$_6$): δ 4.8 (s, 2H), 7.1 (d, 1H), 7.6-7.7 (m, 4H), 8.0 (d, 1H), 8.2 (d, 2H).

Intermediate-13

General Synthetic Route X

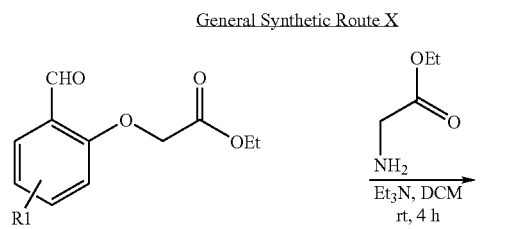

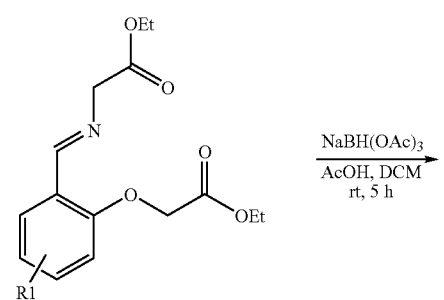

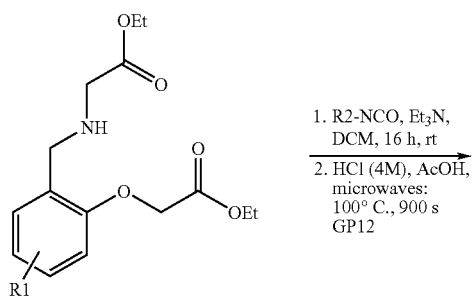

4-Bromo-2-[(ethoxycarbonylmethylamino)methyl]phenoxyacetic acid ethyl ester. 4-Bromo-2-formylphenoxyacetic acid ethyl ester (1.44 g, 5 mmol) was dissolved in dichloromethane (50 mL) and glycine ethyl ester hydrochloride (1.39 g, 10 mmol) as well as Et$_3$N (1.4 mL, 10 mmol) was added. The mixture was stirred at room temperature for 4 h. Water and dichloromethane was added and the organic phase was passed through a phase separation filter and then evaporated to give {4-bromo-2-[(E)-ethoxycarbonylmethyliminomethyl]phenoxy}acetic acid ethyl ester, which was redissolved in dichloromethane (50 mL) and treated with NaBH(OAc)$_3$ (2.11 g, 10 mmol) and AcOH (1 mL), and then stirred at room temperature for 5 h. Saturated Na$_2$CO$_3$, water and dichloromethane was added, and the organic phase was passed through a phase separation filter and evaporated to give the title compound (1.56 g, 84% overall yield).

General Procedure 12 (GP12)

Reaction with Isocyanates Followed by Ringclosure/Hydrolysis

The aldehyde (0.6 mmol) was dissolved in dichloromethane (6 mL), and the isocyanate (1.2 mmol) and Et$_3$N (176 μL, 1.26 mmol) was added. The mixture was stirred at room temperature overnight. Then glycine (150 mg, 2 mmol) was added (as scavenger for excess isocyanate) and the mixture was stirred for additional 2 h. Finally water and dichloromethane was added and the organic phase was passed through a phase separation filter and then evaporated to give the urea, which was dissolved in acetic acid (3.5 mL) and placed in a sealed glass vial. Then 4 M HCl (3.5 mL) was added and the mixture heated by microwaves to 100° C. for 900 s. After cooling to room temperature a white precipitate was formed, and the hydantoin was obtained after filtration and washing with water. In cases where the product did not precipitate after the hydrolysis, dichloromethane and water was added to the mixture, and the organic phase was passed through a phase separation filter. Evaporation of the organic phase gave the product, which in some cases was further purified on a 1 g SAX Acetate SPE column (equilibrated with 100% MeOH and then eluted with 10% AcOH in MeOH).

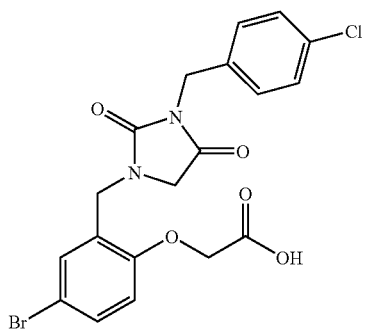

4-Bromo-2-[3-(4-chlorobenzyl)-2,4-dioxoimidazolidin-1-ylmethyl]phenoxyacetic acid. Prepared from 4-bromo-2-[(ethoxycarbonylmethylamino)methyl]phenoxyacetic acid ethyl ester (235 mg, 0.63 mmol) and 4-chlorobenzylisocyanate (166 µL, 1.26 mmol) according to GP12 (yield: 183.4 mg, 62%): LC/MS (an10p8): Rt 2.3 min, m/z 465 [M−H]$^-$; $^1$H NMR (DMSO-d$_6$): δ 4.05 (s, 2H), 4.48 (s, 2H), 4.55 (s, 2H), 4.73 (s, 2H), 6.92 (d, J=8.3 Hz, 1H), 7.25-7.45 (m, 6H), 13.11 (br. s, 1H).

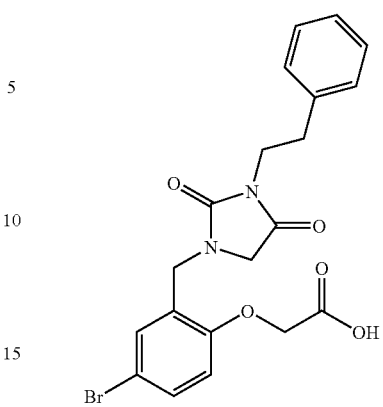

4-Bromo-2-(2,4-dioxo-3-phenethylimidazolidin-1-ylmethyl)phenoxyacetic acid. Prepared from 4-bromo-2-[(ethoxycarbonylmethylamino)methyl]phenoxyacetic acid ethyl ester and phenethylisocyanate according to GP12: LC/MS (an10p8): Rt 2.2 min, m/z 445 [M−H]$^-$; $^1$H NMR (DMSO-d$_6$): δ 2.84 (t, J=7.2 Hz, 2H), 3.59 (t, J=7.2 Hz, 2H), 3.94 (s, 2H), 4.45 (s, 2H), 4.76 (s, 2H), 6.93 (d, J=8.6 Hz, 1H), 7.17-7.46 (m, 7H), 12.45 (br. s, 1H).

General Synthetic Route XI

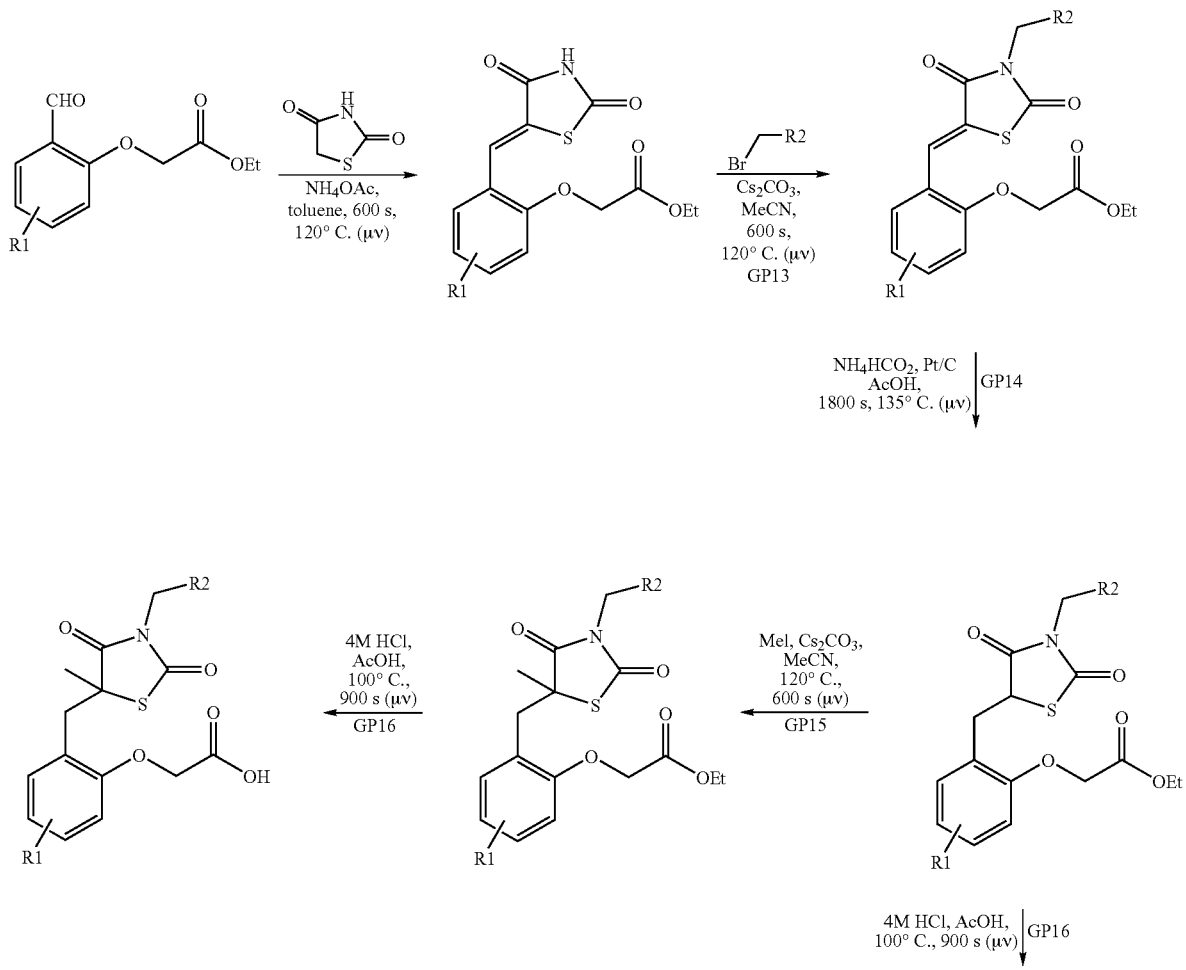

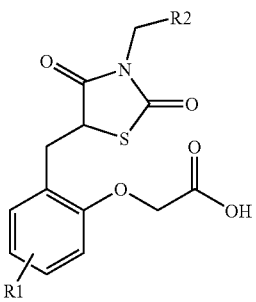

General Procedure 13 (GP13)

N-Alkylation

The 2-[2,4-dioxothiazolidin-(5Z)-ylidenemethyl]phenoxyacetic acid ethyl ester (0.85 mmol), $Cs_2CO_3$ (326 mg, 1.0 mmol), and acetonitrile (10 mL) was mixed in a sealed glass vial. Then the alkylating agent (1.0 mmol) was added and the mixture heated by microwaves to 120° C. for 600 s. Water was added and the mixture was extracted with dichloromethane. The organic phase was passed through a phase separation filter and then evaporated. The product was used directly in the next step or purified by column chromatography ($SiO_2$).

General Procedure 14 (GP14)

Hydrogenation

The 5-benzylidenylthiazolidine-2,4-dione (~0.8 mmol), ammonium formate (1.0 g, 16 mmol), Pt/C (5 wt %, 500 mg, 0.13 mmol), and acetic acid (12 mL) was mixed in a sealed glass vial and heated by microwaves to 135° C. for 1800 s. Then methanol (15 mL) was added and the mixture was filtered through a 20 μm PE filter and then through a 1 g SAX Acetate SPE column, which was washed with additional methanol (10 mL). After evaporation of the methanol, dichloromethane and water was added, and the organic phase was passed through a phase separation filter and concentrated to give the product, which was used directly or purified by column chromatography on $SiO_2$.

General Procedure 15 (GP15)

Alkylation of 5-Position of Thiazolidine-2,4-Diones

3-Alkyl-5-arylmethylthiazolidine-2,4-dione (0.15 mmol), methyl iodide (28 μL, 0.45 mmol), $Cs_2CO_3$ (147 mg, 0.45 mmol), and acetonitrile (10 mL) was mixed in a sealed glass vial and heated by microwaves to 120° C. for 3600 s. Water and dichloromethane was added and the organic phase was passed through a phase separation filter and then evaporated to give the product, which was used directly for the hydrolysis.

General Procedure 16 (GP16)

Acidic Ester Hydrolysis

The ethyl phenoxyacetate (0.02-0.2 mmol) was dissolved in acetic acid (5 mL), 4M HCl (5 mL) was added and the mixture was heated by microwaves to 100° C. for 900 s. After cooling to room temperature a white precipitate was formed, which was filtered of, washed with water and dried to give the product. In cases where the product did not precipitate after the hydrolysis, dichloromethane was added, the organic phase was washed with water and concentrated, and the residue was purified on a 1 g SAX Acetate SPE column (equilibrated with 100% MeOH and then eluted with 10% AcOH in MeOH) to give the product.

Intermediate-14

4-Bromo-2-[2,4-dioxothiazolidinylidenemethyl]phenoxyacetic acid ethyl ester. 4-Bromo-2-formylphenoxyacetic acid ethyl ester (2.47 g, 8.7 mmol), 2,4-thiazolidinedione (1.13 g (90%), 8.7 mmol), and ammonium acetate (671 mg, 8.7 mmol) was mixed with toluene (9 mL) in a sealed vial and heated by microwaves to 120° C. for 600 s. After cooling to room temperature and scratching the inside of the glass, the product precipitated out. The precipitate was filtered and washed with toluene to give the title compound as a yellow solid (2.38 g, 71%).

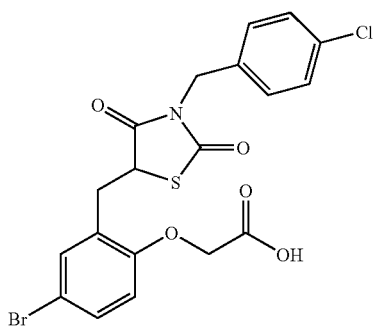

D141

4-Bromo-2-[3-(4-chlorobenzyl)-2,4-dioxothiazolidin-5-ylmethyl]phenoxyacetic acid. Prepared from 4-chlorobenzylbromide and 4-bromo-2-[2,4-dioxothiazolidin-(5Z)-ylidenemethyl]phenoxyacetic acid ethyl ester according to GP13, GP14 and GP16 to give 50.4 mg (21% overall yield) of the title compound: LC/MS (an10p8): Rt 2.6 min, m/z 482 [M−H]−. $^1$H NMR (DMSO-$d_6$): δ 3.05 (dd, J=13.8, 9.7 Hz, 1H), 3.57 (dd, J=13.8, 4.9 Hz, 1H), 5.11 (dd, J=9.7, 4.9 Hz, 1H), 4.67 (s, 2H), 4.75 (s, 2H), 6.91 (d, J=8.7, 1H), 7.25-7.28 (m, 2H), 7.37-7.42 (m, 4H), 13.15 (br. s, 1H).

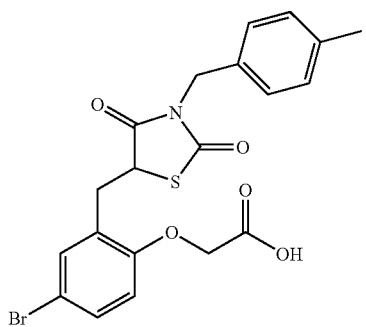

D142

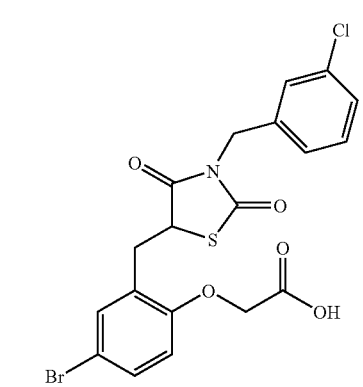

D144

4-Bromo-2-[3-(4-methylbenzyl)-2,4-dioxothiazolidin-5-ylmethyl]phenoxyacetic acid. Prepared from 4-methylbenzylbromide and 4-bromo-2-[2,4-dioxothiazolidin-(5Z)-ylidenemethyl]phenoxyacetic acid ethyl ester according to GP13, GP14 and GP16 (yield: 14 mg, 21%): LC/MS (an10p8): Rt 2.5 min, m/z 462 [M−H]⁻. $^1$H NMR (DMSO-$d_6$): δ 2.98-3.07 (m, 1H), 3.53-3.59 (m, 1H), 4.63 (s, 2H), 4.74 (s, 2H), 5.07-5.13 (m, 1H), 6.89-6.91 (m, 1H), 7.11-7.16 (m, 4H), 7.38-7.43 (m, 2H), 13.11 (br s, 1H).

4-Bromo-2-[3-(3-chlorobenzyl)-2,4-dioxothiazoldin-5-ylmethyl]phenoxyacetic acid (7d). Prepared from 3-chlorobenzyl bromide and 4-bromo-2-[2,4-dioxothiazolidin-(5Z)-ylidenemethyl]phenoxyacetic acid ethyl ester according to GP13, GP14 and GP16: LC/MS (an10p8): Rt 2.6 min, m/z 484 [M+H]⁺. $^1$H NMR (DMSO-$d_6$): δ 3.02-3.10 (m, 1H), 3.54-3.60 (m, 1H), 4.69 (s, 2H), 4.75 (s, 2H), 5.09-5.14 (m, 1H), 6.89-6.92 (m, 1H), 7.18 (m, 1H), 7.33-7.43 (m, 5H), 13.01 (br s, 1H).

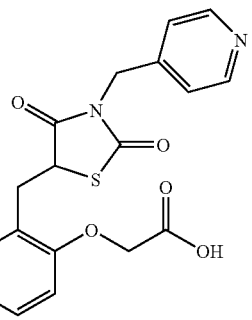

D145

4-Bromo-2-(2,4-dioxo-3-pyridin-4-ylmethylthiazolidin-5-ylmethyl)phenoxyacetic acid. Prepared from 4-bromomethylpyridine and 4-bromo-2-[2,4-dioxothiazolidin-(5Z)-ylidenemethyl]phenoxyacetic acid ethyl ester according to GP13, GP14 and GP16: LC/MS (an10p8): Rt 2.1 min, m/z 451 [M+H]⁺.

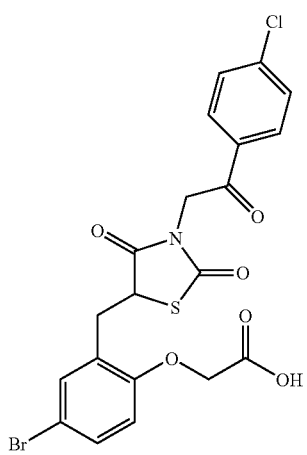

D143

4-Bromo-2-{3-[2-(4-chlorophenyl)-2-oxoethyl]-2,4-dioxothiazolidin-5-ylmethyl}phenoxyacetic acid. Prepared from 2-bromo-1-(4-chlorophenyl)ethanone and 4-bromo-2-[2,4-dioxothiazolidin-(5Z)-ylidenemethyl]phenoxyacetic acid ethyl ester according to GP13, GP14 and GP16 (yield: 8.2 mg, 34%): LC/MS (an10p8): Rt 2.8 min, m/z 510 [M−H]⁻. $^1$H NMR (DMSO-$d_6$): δ 3.01-3.09 (m, 1H), 3.57-3.63 (m, 1H), 4.79 (s, 2H), 5.17 (s, 2H), 5.21-5.24 (m, 1H), 6.91-6.95 (m, 1H), 7.44 (m, 2H), 7.66-7.69 (m, 2H), 8.07-8.09 (m, 2H).

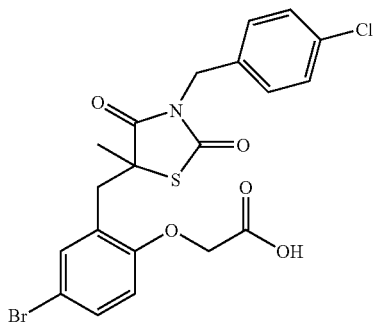

D146

4-Bromo-2-[3-(4-chlorobenzyl)-5-methyl-2,4-dioxothiazolidin-5-ylmethyl]-phenoxyacetic acid. Prepared from 4-bromomethylpyridine according to GP13, GP14, GP15 and GP16 (yield: 29 mg, 15%): LC/MS (an10p8): Rt 3.0 min, m/z 496 [M−H]⁻; ¹H NMR (DMSO-d₆): 1.71 (s, 3H), 3.24 (d, J=13.8 Hz, 1H), 3.39 (d, J=13.8 Hz, 1H), 4.63-4.68 (m, 4H), 6.86 (d, J=8.6 Hz, 1H), 7.13-7.43 (m, 6H), 13.08 (br s, 1H).

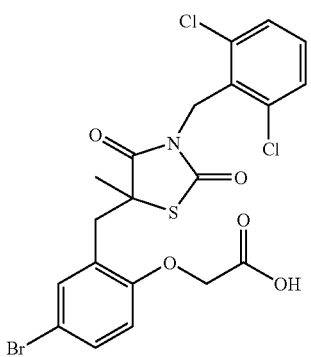

D147

4-Bromo-2-[3-(2,6-dichlorobenzyl)-5-methyl-2,4-dioxothiazolidin-5-ylmethyl]phenoxyacetic acid. Prepared from 2,6-dichlorobenzylbromide according to GP13, GP14, GP15 and GP16 to give 21.1 mg of the title compound: LC/MS (an10n8): Rt 2.9 min, m/z 532 [M−H]⁻; ¹H NMR (DMSO-d₆): δ 1.63 (s, 3H), 3.16 (d, J=13.6 Hz, 1H), 3.40 (d, J=13.6 Hz, 1H), 4.65 (s, 2H), 4.92 (s, 2H), 6.86 (d, J=8.9 Hz, 1H), 7.21 (d, J=2.5 Hz, 1H), 7.35-7.48 (m, 4H), 12.38 (br s, 1H).

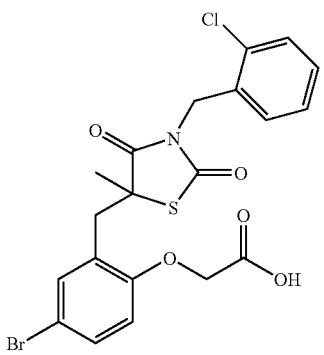

D148

4-Bromo-2-[3-(2-chlorobenzyl)-5-methyl-2,4-dioxothiazolidin-5-ylmethyl]phenoxyacetic acid. Prepared from 2-chlorobenzylbromide according to GP13, GP14, GP15 and GP16 to give 22.0 mg of the title compound: LC/MS (an10n8): Rt 2.8 min, m/z 498 [M−H]⁻; ¹H NMR (DMSO-d₆): δ 1.76 (s, 3H), 3.28 (d, J=13.7 Hz, 1H), 3.43 (d, J=13.7 Hz, 1H), 4.67 (d, J=3.2 Hz, 2H), 4.73 (s, 2H), 6.81 (d, J=8.9 Hz, 1H), 6.90 (d, J=8.7 Hz, 1H), 7.24-7.36 (m, 3H), 7.43-7.50 (m, 2H), 12.18 (br s, 1H).

Biological Assays
Materials and Methods

Generation/origin of the cDNA Constructs. The coding sequence of the human CRTH2 receptor (genbank accession no NM_004778) was amplified by PCR from a human hippocampus cDNA library and inserted into the pcDNA3.1(+) expression vector (invitrogen) via 5' HindIII and 3' EcoRI. To generate a CRTH2-*Renilla* luciferase (CRTH2-Rluc) fusion protein, the CRTH2 coding sequence without a STOP codon and Rluc were amplified, fused in frame by PCR and subcloned into the pcDNA3.1(+)Zeo expression vector (invitrogen). Human β-arrestin2 (β-arr2) N-terminally tagged with GFP² (βarr2-GFP²) and *Renilla* luciferase were purchased from BioSignal Packard Inc, (Montreal, Canada). The sequence identity of the construct was verified by restriction endonuclease digests and sequencing in both directions on an ABI Prism (Applied Biosystems, Foster City, Calif.).

Sequence ID CRTH2 (Protein Sequence) (SEQ ID NO:1):

MSANATLKPLCPILEQMSRLQSHSNTSIRYIDHAAVLLHGLASLLGLVEN

GVILFVVGCRMRQTVVTTWVLHLALSDLLASASLPFFTYFLAVGHSWELG

TTFCKLHSSIFFLNMFASGFLLSAISLDRCLQVVRPVWAQNHRTVAAHK

VCLVLWALAVLNTVPYFVFRDTISRLDGRIMCYYNVLLLNPGPDRDATCN

SRQAALAVSKFLLAFLVPLAIIASSHAAVSLRLQHRGRRRPGRFVRLVAA

VVAAFALCWGPYHVFSLLEARAHANPGLRPLVWRGLPFVTSLAFFNSVAN

PVLYVLTCPDMLRKLRRSLRTVLESVLVDDSELGGAGSSRRRRTSSTARS

ASPLALCSRPEEPRGPARLLGWLLGSCAASPQTGPLNRALSSTSS

Sequence ID CRTH2 (Nucleotide Sequence) (SEQ ID NO:2):

```
atgtcggc caacgccaca  ctgaagccac  tctgccccat  cctggagcag
atgagccgtc tccagagcca cagcaacacc  agcatccgct  acatcgacca  cgcggccgtg
ctgctgcacg ggctggcctc gctgctgggc  ctggtggaga  atggagtcat  cctcttcgtg
gtgggctgcc gcatgcgcca gaccgtggtc  accacctggg  tgctgcacct  ggcgctgtcc
gacctgttgg cctctgcttc cctgcccttc  ttcacctact  tcttggccgt  gggccactcg
tgggagctgg gcaccacctt ctgcaaactg  cactcctcca  tcttctttct  caacatgttc
gccagcggct tcctgctcag cgccatcagc  ctggaccgct  gcctgcaggt  ggtgcggccg
gtgtgggcgc agaaccaccg caccgtggcc  gcggcgcaca  aagtctgcct  ggtgctttgg
gcactagcgg tgctcaacac ggtgccctat  ttcgtgttcc  gggacaccat  ctcgcggctg
gacgggcgca ttatgtgcta ctacaatgtg  ctgctcctga  acccggggcc  tgaccgcgat
gccacgtgca
```

```
            -continued
actcgcgcca ggcggccctg gccgtcagca agttcctgct ggccttcctg
gtgccgctgg cgatcatcgc ctcgagccac gcggccgtga gcctgcggtt gcagcaccgc
ggccgccggc ggccaggccg cttcgtgcgc ctggtggcag ccgtcgtggc cgccttcgcg
ctctgctggg ggccctacca cgtgttcagc ctgctggagg cgcgggcgca cgcaaacccg
gggctgcggc cgctcgtgtg gcgcgggctg cccttcgtca ccagcctggc cttcttcaac
agcgtggcca acccggtgct ctacgtgctc acctgccccg acatgctgcg caagctgcgg
cgctcgctgc gcacggtgct ggagagcgtg ctggtggacg acagcgagct gggtggcgcg
ggaagcagcc gccgccgcg cacctcctcc accgcccgct cggcctcccc tttagctctc
tgcagccgcc cggaggaacc gcggggcccc gcgcgtctcc tcggctggct gctgggcagc
tgcgcagcgt ccccgcagac gggcccctg aaccgggcgc tgagcagcac ctcgagttag
```

Cell Culture and Transfection. COS-7 cells were grown in Dulbecco's modified Eagle's medium (DMEM) 1885 supplemented with 10% fetal bovine serum, 100 units/ml penicillin, 1000 µg/ml streptomycin, and kept at 37° C. in a 10% $CO_2$ atmosphere. HEK293 cells were maintained in Minimum Essential medium (MEM) supplemented with 10% (v/v) heat inactivated fetal calf serum (HIFCS), 2 mM Glutamax™-I, 1% non essential amino acids (NEAA), 1% sodium pyruvate and 10 µg/ml gentamicin. For binding experiments, COS7 cells were transiently transfected with the CRTH2 receptor using a calcium phosphate-DNA coprecipitation method with the addition of chloroquine (as described by Holst et al., 2001↓). To perform the functional Bioluminescence Resonance Energy Transfer (BRET) assays, a HEK293 cell clone stably expressing βarr2-GFP$^2$ and CRTH2-Rluc was generated (CRTH2-HEK293 cells).

Binding assay. 24 h after transfection COS-7 cells were seeded into 96 well plates at a density of 30.000 cells/well. Competition binding experiments on whole cells were then performed about 18-24 h later using 0.1 nM [$^3$H]PGD2 (NEN, 172 Ci/mmol) in a binding buffer consisting of HBSS (GIBCO) and 10 mM HEPES. Competing ligands were diluted in DMSO which was kept constant at 1% (v/v) of the final incubation volume. Total and nonspecific binding were determined in the absence and presence of 10 µM PGD2. Binding reactions were routinely conducted for 3 h at 4° C. and terminated by 2 washes (100 µl each) with ice cold binding buffer. Radioactivity was determined by liquid scintillation counting in a TOPCOUNTER (Packard) following over night incubation in Microscint 20. Stable HEK293 cells were seeded at a density of 30.000 cells/well 18-24 h prior to the binding assay which was performed essentially as described for COS7 cells above. Determinations were made in duplicates.

BRET assay. Functional BRET assays were performed on HEK293 cells stably expressing human CRTH2-Rluc and GFP$^2$-β-arr2. Prior to their use in the BRET assay cells were detached and re-suspended in D-PBS with 1000 mg/L L-Glucose at a density of $2 \times 10^6$ cells/mL. DeepBlueC™ was diluted to 50 µM in D-PBS with 1000 mg/L L-Glucose (light sensitive). 100 µL of cell suspension was transferred to wells in a 96-well microplate (white OptiPlate) and placed in the Mithras LB 940 instrument (BERTHOLD TECHNOLOGIES, Bad Wildbad, Germany). 12 µL/well agonist was then injected by injector 1 and 10 µL/well DeepBlueC™ was injected simultaneously by injector 2. Five seconds after the injections the light output from the well was measured sequentially at 400 nm and 515 nm, and the BRET signal (mBRET ratio) was calculated by the ratio of the fluorescence emitted by GFP$^2$-β-arr2 (515 nm) over the light emitted by the receptor-Rluc (400 nm). Antagonists were added before placing the microplates into the Mithras LB 940 and allowed to incubate for 15 minutes prior to the addition of agonist and DeepBlueC™. Compounds were dissolved in DMSO and the final DMSO concentration was kept constant at 1% in the assay.

Human eosinophil shape change assay. Blood was sampled from healthy volunteers according to a protocol approved by the Ethics Committee of the University of Graz and processed as described previously (Bohm et al., 2004). Preparations of polymorphonuclear leukocytes (containing eosinophils and neutrophils) were prepared by dextran sedimentation of citrated whole blood and Histopaque gradients. The resulting cells were washed and resuspended in assay buffer (comprising PBS with $Ca^{2+}/Mg^{2+}$ supplemented with 0.1% BSA, 10 mM HEPES and 10 mM glucose, pH 7.4) at $5 \times 10^6$ cells/mL. Cells were incubated with the antagonists or vehicle (PBS or DMSO) for 10 min at 37° C. and then stimulated with various concentration of the agonists (PGD2 or eotaxin) for 4 min at 37° C. To stop the reaction, samples were transferred to ice and fixed with 250 µL of fixative solution. Samples were immediately analyzed on a FACSCalibur flow cytometer (Becton Dickinson) and eosinophils were identified according to their autofluorescence in the FL-1 and FL-2 channels. Shape change responses were quantified as percentage of the maximal response to PGD2 or eotaxin in the absence of an antagonist.

Materials

Tissue culture media and reagents were purchased from the Gibco invitrogen corporation (Breda, Netherlands). PGD2 was obtained from Cayman and [3H]PGD2 from NEN.

Data Analysis

Curve analysis was performed with the GraphPadPrism software 3.0 (Graphpad Prism Inc., San Diego, USA) and $IC_{50}$ values were calculated as a measure of the antagonistic potencies.

REFERENCES

Holst B, Hastrup H, Raffetseder U, Martini L, Schwartz T W. Two active molecular phenotypes of the tachykinin NK1 receptor revealed by G-protein fusions and mutagenesis. J Biol. Chem. 2001 Jun. 8; 276(23):19793-9. Epub 2001 Feb. 22.

Biological Data:

Compounds were tested in the receptor binding assay and the functional antagonist assay described below, and their $IC_{50}$ values were assessed. The compounds are grouped in three classes:

A: $IC_{50}$ value lower than 0.5 μM
B: $IC_{50}$ value between 0.5 μM and 5 μM
C: $IC_{50}$ value higher than 5 μM Tables 1 to 7 give the biological test results for the compounds synthesised above and for some additional compounds acquired from commercial sources. The ability of the compounds above to inhibit prostaglandin D2 induced eosinophil shape change is demonstrated by the examples in FIG. 1.

TABLE 1

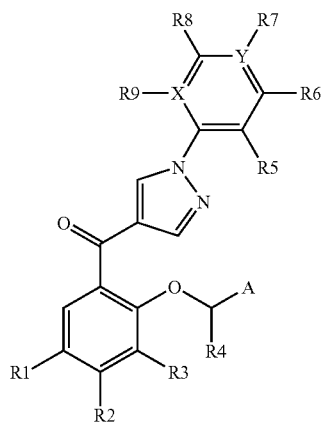

|  | A | R1 | R2 | R3 | R4 | R5 | R6 | R7 | R8 | R9 | X | Y | Binding $IC_{50}$ | Antag. $IC_{50}$ |
|---|---|---|---|---|---|---|---|---|---|---|---|---|---|---|
| D1 | COOH | Br | H | H | H | H | H | H | H | H | C | C | A | A |
| D2 | COOH | H | H | H | H | H | H | H | H | H | C | C | A | B |
| D3 | COOH | F | H | H | H | H | H | H | H | H | C | C | A | B |
| D4 | Tetrazole | Br | H | H | H | H | H | H | H | H | C | C | A | C |
| D5 | COOH | Ph | H | H | H | H | H | H | H | H | C | C | A | A |
| D6 | COOH | Br | H | H | H | H | H | H | H | — | N | C | A | A |
| D7 | COOH | Br | H | H | H | H | H | OMe | H | H | C | C | A | A |
| D8 | COOH | 3,5-difluorophenyl | H | H | H | H | H | H | H | H | C | C | A | B |
| D9 | COOH | 4-chlorophenyl | H | H | H | H | H | H | H | H | C | C | A | A |
| D10 | COOH | Cl | H | H | H | H | H | H | H | H | C | C | A | B |
| D11 | COOH | Me | H | H | H | H | H | H | H | H | C | C | A | B |
| D12 | COOH | Cl | Me | H | H | H | H | H | H | H | C | C | B | C |
| D13 | COOH | Cl | H | Cl | H | H | H | H | H | H | C | C | C | C |
| D14 | COOH | Br | H | H | H | Cl | H | H | H | H | C | C | C | A |
| D15 | COOH | Br | H | H | H | H | Cl | H | H | H | C | C | A | A |
| D16 | COOH | Br | H | H | H | H | H | Br | H | H | C | C | A | A |
| D17 | COOH | Br | H | H | H | H | H | Cl | H | H | C | C | A | A |
| D18 | COOH | Br | H | H | H | Et | H | H | H | H | C | C | A | A |
| D19 | COOH | Br | H | H | H | H | H | Cl | H | H | C | C | A | A |
| D20 | COOH | $NO_2$ | H | H | H | H | H | H | H | H | C | C | A | A |
| D21 | COOH | Br | H | H | H | Br | H | H | H | H | C | C | A | A |
| D22 | COOH | Br | H | H | H | F | H | H | H | H | C | C | A | A |
| D23 | COOH | Br | H | H | H | $CF_3$ | H | H | H | H | C | C | A | A |
| D24 | COOH | Br | H | H | H | H | Br | H | H | H | C | C | A | A |
| D25 | COOH | Br | H | H | H | H | $CF_3$ | H | H | H | C | C | A | A |
| D26 | COOH | Br | H | H | H | Cl | H | Cl | H | H | C | C | A | A |
| D27 | COOH | $NO_2$ | H | H | H | Cl | H | H | H | H | C | C | A | A |
| D28 | COOH | $NO_2$ | H | H | H | Br | H | H | H | H | C | C | A | A |

TABLE 1-continued

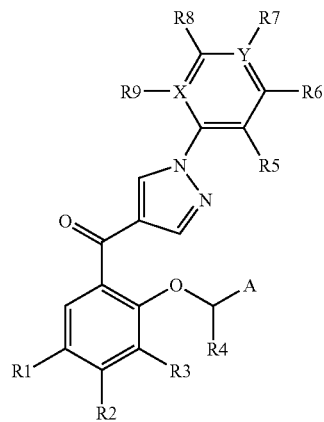

| | A | R1 | R2 | R3 | R4 | R5 | R6 | R7 | R8 | R9 | X | Y | Binding IC$_{50}$ | Antag. IC$_{50}$ |
|---|---|---|---|---|---|---|---|---|---|---|---|---|---|---|
| D29 | COOH | Br | H | H | H | Cl | H | H | H | Cl | C | C | A | A |
| D30 | COOH | Et | H | H | H | Br | H | H | H | H | C | C | A | A |
| D31 | COOH | i-Pr | H | H | H | Cl | H | H | H | H | C | C | A | A |
| D32 | COOH | Br | H | H | H | H | H | OCF$_3$ | H | H | C | C | A | A |
| D33 | COOH | Br | H | H | H | Br | H | Br | H | H | C | C | A | A |
| D34 | COOH | Br | H | H | H | Cl | H | Br | H | H | C | C | A | A |
| D35 | COOH | Br | H | H | H | Cl | H | Cl | H | Cl | C | C | A | A |
| D36 | COOH | OMe | H | H | H | H | H | H | H | H | C | C | A | B |
| D37 | COOH | Br | H | H | Me | H | H | H | H | H | C | C | A | A |
| (S)-D37 | COOH | Br | H | H | Me | H | H | H | H | H | C | C | A | A |
| D38 | COOH | Br | H | H | Me | Cl | H | H | H | H | C | C | A | A |
| D39 | COOH | Br | H | H | Me | Cl | H | H | H | Cl | C | C | A | A |
| D40 | COOH | Br | H | H | H | CN | H | H | H | H | C | C | A | A |
| D41 | COOH | Br | H | H | H | OEt | H | H | H | H | C | C | A | A |
| D42 | COOH | Br | H | H | H | Et | H | Br | H | H | C | C | A | A |
| D43 | COOH | Br | H | H | H | OPh | H | H | H | H | C | C | A | A |
| D44 | COOH | Br | H | H | H | SMe | H | H | H | H | C | C | A | A |
| D45 | COOH | Br | H | H | H | Br | H | Me | H | H | C | C | A | A |
| D46 | COOH | Br | H | H | Me | Et | H | Br | H | H | C | C | A | A |
| D47 | COOH | Br | H | H | Me | OPh | H | H | H | H | C | C | A | A |
| D48 | COOH | Br | H | H | Me | OEt | H | H | H | H | C | C | A | A |
| D49 | COOH | Br | H | H | Me | SMe | H | H | H | H | C | C | A | A |
| D50 | COOH | Br | H | H | Me | Br | H | Me | H | H | C | C | A | A |
| D51 | COOH | Br | H | H | Me | OPh | H | H | H | H | C | C | A | A |
| D52 | COOH | Br | H | H | H | OCF$_3$ | H | H | H | H | C | C | A | A |
| D53 | COOH | Et | H | H | H | Me | H | H | H | Me | C | C | A | A |
| D54 | COOH | Br | H | H | H | Me | H | Me | H | H | C | C | A | A |
| D55 | COOH | Br | H | H | Me | Me | H | Me | H | H | C | C | A | A |
| D58 | COOH | Br | H | H | H | Me | H | Cl | H | H | C | C | A | A |
| D59 | COOH | Br | H | H | H | Cl | H | H | Cl | H | C | C | A | A |
| D60 | COOH | Br | H | H | H | OMe | H | H | H | H | C | C | A | A |
| D61 | COOH | Br | H | H | H | H | Cl | Cl | H | H | C | C | A | A |
| D62 | COOH | Br | H | H | Me | Me | H | Cl | H | H | C | C | A | A |
| D63 | COOH | Br | H | H | Me | Cl | H | Cl | H | H | C | C | A | A |
| D64 | COOH | Br | H | H | Me | H | Cl | Cl | H | H | C | C | A | A |
| D65 | COOH | Br | H | H | Me | OMe | H | H | H | H | C | C | A | A |
| D66 | COOH | NH$_2$ | H | H | H | H | H | H | H | H | C | C | B | A |
| D67 | COOH | Br | H | H | Me | Cl | H | Br | H | H | C | C | A | A |
| D68 | COOH | Br | H | H | Me | Cl | H | Cl | H | Cl | C | C | A | A |
| D69 | COOH | Br | H | H | Me | Br | H | Br | H | H | C | C | A | A |
| D70 | COOH | Br | H | H | H | Et | H | H | H | Et | C | C | A | A |
| D71 | COOH | Br | H | H | H | Me | H | H | H | Me | C | C | A | A |
| D72 | COOH | Br | H | H | H | Et | H | H | H | Me | C | C | A | A |
| D73 | COOH | Br | H | H | H | i-Pr | H | H | H | H | C | C | A | A |
| D74 | COOH | EtO | H | H | H | H | H | H | H | H | C | C | B | C |
| D75 | COOH | n-Bu | H | H | H | H | H | H | H | H | C | C | A | C |
| D76 | COOH | Br | H | H | H | Cl | H | H | H | Me | C | C | A | A |
| D77 | COOH | Br | H | H | Me | Me | H | H | H | Me | C | C | A | A |
| D78 | COOH | Br | H | H | Me | Et | H | H | H | Et | C | C | A | A |
| D79 | COOH | Br | H | H | Me | i-Pr | H | H | H | H | C | C | A | A |
| D80 | COOH | Br | H | H | H | Cl | H | H | H | Cl | C | N | A | A |
| D81 | COOH | Br | H | H | H | H | H | CF$_3$ | H | H | C | C | A | A |

TABLE 2

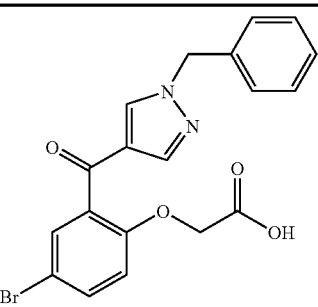

| | n | X | R1 | R2 | R3 | R4 | R5 | Binding IC$_{50}$ | Antag. IC$_{50}$ |
|---|---|---|---|---|---|---|---|---|---|
| D83 | 0 | O | H | H | H | H | H | A | C |
| D84 | 0 | O | H | H | OMe | H | H | A | B |
| D85 | 0 | O | H | H | Cl | H | H | A | C |
| D86 | 0 | O | H | OMe | H | H | H | A | A |
| D87 | 0 | O | H | H | OEt | H | H | A | C |
| D88 | 1 | O | H | H | H | H | H | A | A |
| D89 | 1 | O | H | OMe | H | H | H | A | A |
| D90 | 1 | O | Cl | H | F | H | H | A | A |
| D91 | 1 | O | Cl | H | H | H | Cl | A | A |
| D92 | 1 | O | H | H | OMe | H | H | A | A |
| D93 | 0 | S | H | H | H | H | H | A | A |
| D94 | 1 | S | H | H | Cl | H | H | A | A |

TABLE 3

| | n | R1 | R2 | R3 | R4 | R5 | Binding IC$_{50}$ | Antag. IC$_{50}$ |
|---|---|---|---|---|---|---|---|---|
| D99 | 0 | H | H | H | H | H | A | A |
| D100 | 0 | H | H | F | H | H | A | A |
| D101 | 0 | H | H | OMe | H | H | A | A |
| D102 | 0 | H | H | Cl | H | H | A | A |
| D103 | 0 | H | H | OCF$_3$ | H | H | A | A |
| D104 | 0 | H | OMe | H | H | H | A | A |
| D105 | 0 | H | Cl | H | H | H | A | A |
| D106 | 0 | H | H | CF$_3$ | H | H | A | A |
| D107 | 0 | OMe | H | H | H | H | A | A |
| D108 | 0 | Cl | H | H | H | H | A | A |
| D109 | 0 | H | CF$_3$ | H | CF$_3$ | H | A | C |
| D110 | 0 | Cl | H | H | H | Cl | A | A |
| D111 | 0 | H | H | OPh | H | H | A | A |
| D112 | 0 | H | CF$_3$ | H | H | H | A | A |
| D113 | 1 | H | H | OCF$_3$ | H | H | A | A |
| D114 | 1 | H | H | Cl | H | H | A | A |
| D115 | 1 | H | H | H | H | H | A | A |
| D116 | 1 | H | H | F | H | H | A | A |
| D117 | 1 | H | F | H | F | H | A | A |
| D118 | 1 | H | H | OMe | H | H | A | A |
| D119 | 1 | H | OMe | H | H | H | A | A |
| D120 | 1 | Cl | H | H | H | H | A | A |
| D121 | 1 | Cl | H | H | H | Cl | A | A |
| D122 | 1 | Cl | H | Cl | H | H | A | A |
| D123 | 1 | H | Cl | Cl | H | H | A | A |
| D124 | 1 | H | OMe | OMe | H | H | A | A |

TABLE 3-continued

| | n | R1 | R2 | R3 | R4 | R5 | Binding IC$_{50}$ | Antag. IC$_{50}$ |
|---|---|---|---|---|---|---|---|---|
| D125 | 1 | H | OMe | H | H | H | A | C |
| D126 | 1 | H | H | Me | H | H | A | A |
| D127 | 1 | CF$_3$ | H | H | H | H | A | A |
| D128 | 1 | H | OMe | H | OMe | H | A | B |
| D129 | 0 | Cl | H | Cl | H | H | A | A |
| D130 | 1 | H | Cl | H | H | H | A | A |
| D131 | 1 | H | H | NHAc | H | H | A | A |

TABLE 4

| | n | R1 | R2 | R3 | R4 | R5 | Activity | Binding IC$_{50}$ | Antag. IC$_{50}$ |
|---|---|---|---|---|---|---|---|---|---|
| D134 | 0 | H | H | 4-PhOMe | H | H | A | A | A |
| D135 | 0 | H | H | Cl | H | H | A | A | A |
| D136 | 0 | H | Cl | H | H | H | A | A | A |
| D137 | 0 | Cl | H | H | H | H | A | A | A |
| D138 | 0 | H | H | H | H | H | A | A | C |

TABLE 5

| | Structure | Binding IC$_{50}$ | Antag. IC$_{50}$ |
|---|---|---|---|
| D56 | 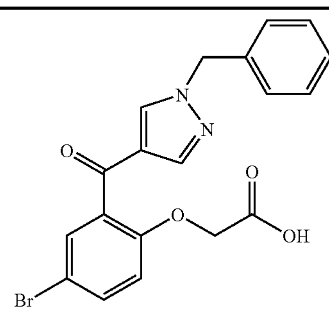 | A | A |

TABLE 5-continued

| Structure | Binding IC$_{50}$ | Antag. IC$_{50}$ |
|---|---|---|
| D57 | A | A |
| D82 | A | A |
| D95 | A | A |
| D96 | A | B |
| D97 | A | A |
| D98 | A | |
| D132 | A | A |
| D133 | A | C |

TABLE 6

| | Structure | Binding IC$_{50}$ | Antag. IC$_{50}$ |
|---|---|---|---|
| D139 | 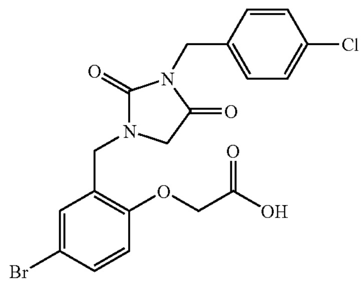 | A | A |
| D140 | 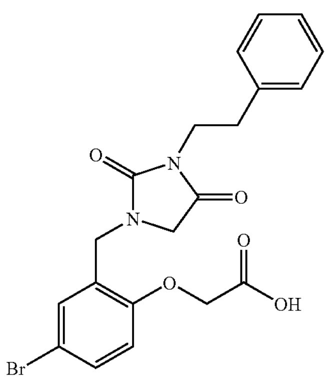 | A | B |
| D141 | 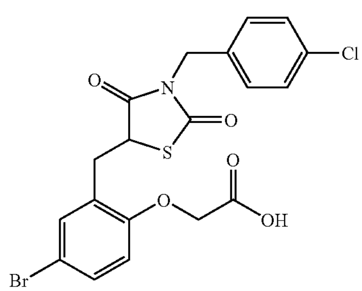 | A | A |
| D142 | 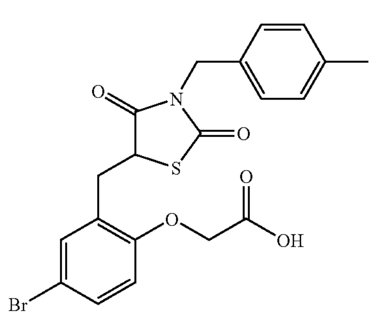 | A | A |
| D143 | | A | A |
| D144 | | A | A |
| D145 | | A | A |
| D146 | | A | A |

TABLE 7

Structure (left column, Cmp D149–D152):
R1 at position on benzene; HN-R2 hydrazone; O-CH2-COOH ether.

| Cmp | R1 | R2 | Binding IC50 | Antag. IC50 |
|---|---|---|---|---|
| D149 | H | -C(=O)-CH2-O-(2,4-dichlorophenyl) | A | A |
| D150 | Br | 8-quinolinyl | A | C |
| D151 | Br | 2-pyridyl | A | C |
| D152 | Br | 3-(5-phenyl-1,2,4-triazinyl) | A | B |

TABLE 7-continued

| Cmp | R1 | R2 | Binding IC50 | Antag. IC50 |
|---|---|---|---|---|
| D153 | H | 3-(5-(4-methoxyphenyl)-1,2,4-triazinyl) | B | C |
| D154 | H | -C(=O)-(1-hydroxy-2-naphthyl) | A | A |
| D155 | H | -C(=O)-(2-phenyl-4-pyridyl) | A | B |
| D156 | H | -C(=O)-CH2-S-(4-phenyl-5-(4-chlorophenyl)-4H-1,2,4-triazol-3-yl) | A | B |

---

The invention claimed is:

1. A compound of formula (IV) or a salt thereof

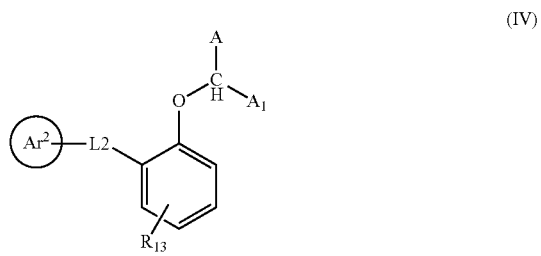

(IV)

wherein

A is —COOH or a carboxyl bioisostere selected from —SO$_2$NHR and —P(=O)(OH)(OR) wherein R is hydrogen methyl or ethyl, —SO$_2$OH, —P(=O)(OH)(NH$_2$), —C(=O)NHCN, and groups of formulae:

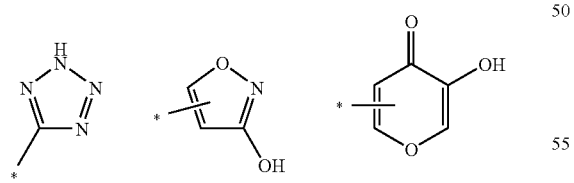

$A_1$ is hydrogen or methyl; and ring $Ar^2$ represents a phenyl or 5- or 6-membered monocyclic heteroaryl ring, or a bicyclic ring system consisting of a 5- or 6-membered carbocyclic or heterocyclic ring which is benz-fused or fused to a 5- or 6-membered monocyclic heteroaryl ring, said ring or ring system being optionally substituted with up to four compatible substituents independently selected from (C$_1$-C$_6$)alkyl, (C$_1$-C$_6$)alkoxy, hydroxy, hydroxy(C$_1$-C$_6$)alkyl, mercapto, mercapto(C$_1$-C$_6$)alkyl, (C$_1$-C$_6$)alkylthio, halo including fluoro, bromo and chloro, fully or partially fluorinated (C$_1$-C$_3$)alkyl, (C$_1$-C$_3$)alkoxy or (C$_1$-C$_3$) alkylthio such as trifluoromethyl, trifluoromethoxy, and trifluoromethylthio, nitro, nitrile (—CN), oxo, phenyl, phenoxy, —COOR$^A$, —COR$^A$, —OCOR$^A$, —SO$_2$R$^A$, —CONR$^A$R$^B$, —SO$_2$NR$^A$R$^B$, —NR$^A$R$^B$, —OCONR$^A$R$^B$, —NR$^B$COR$^A$, —NR$^B$COOR$^A$, —NR$^B$SO$_2$OR$^A$ or —NR$^A$CONR$^A$R$^B$ wherein R$^A$ and R$^B$ are independently hydrogen or a (C$_1$-C$_6$)alkyl group or, in the case where R$^A$ and R$^B$ are linked to the same N atom, R$^A$ and R$^B$ taken together with that nitrogen may form a cyclic amino ring, and where the substituent is phenyl or phenoxy, the phenyl ring thereof may itself be substituted by any of the above substituents except phenyl or phenoxy groups, R$_{13}$ represents hydrogen or one or more optional substituents selected from fluoro, chloro, bromo, iodo, cyano, nitro, trifluoromethyl, trifluoromethoxy, trifluoromethylthio, (C$_1$-C$_3$alkyl)SO$_2$—, NH$_2$SO$_2$—, (C$_1$-C$_3$alkyl)NHSO$_2$—, (C$_1$-C$_3$alkyl)$_2$NSO$_2$—, C$_1$-C$_6$ alkyl, C$_1$-C$_6$ alkoxy, cycloalkyl, aryl, aryloxy, aryl(C$_1$-C$_6$)- or aryl (C$_1$-C$_6$alkoxy)-, L2 is a divalent radical selected from the following wherein either (i) the bond marked * is attached to Ar$^2$ while the bond marked ** is attached to the phenyl ring, or (ii) the bond marked * is attached to the phenyl ring while the bond marked ** is attached to Ar²:
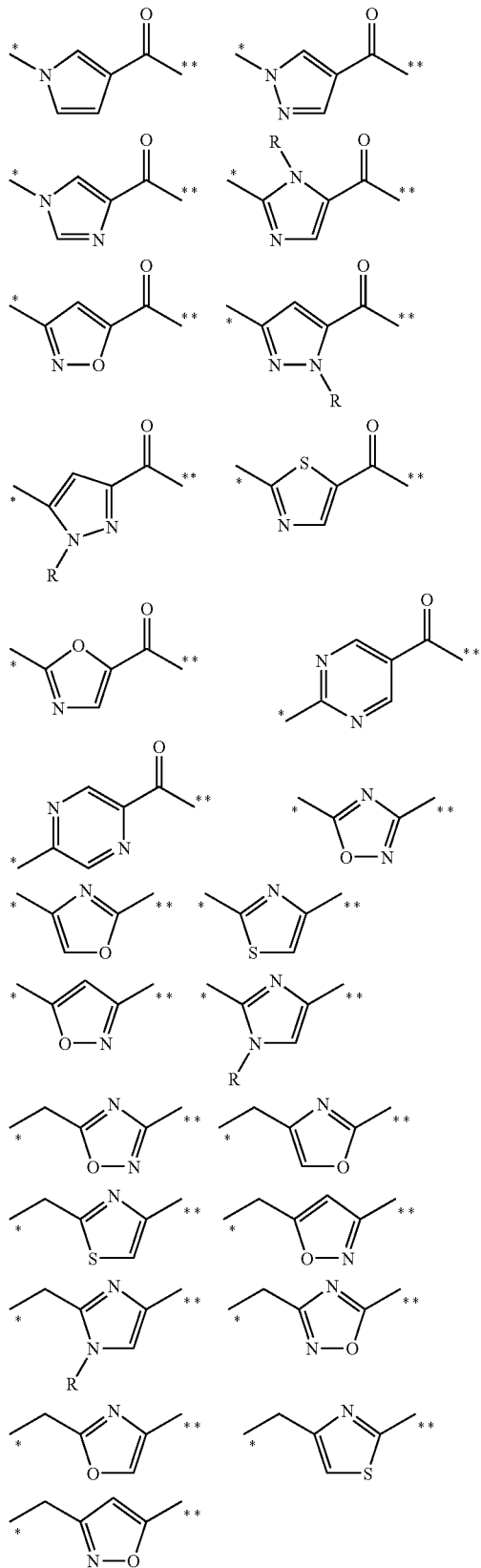
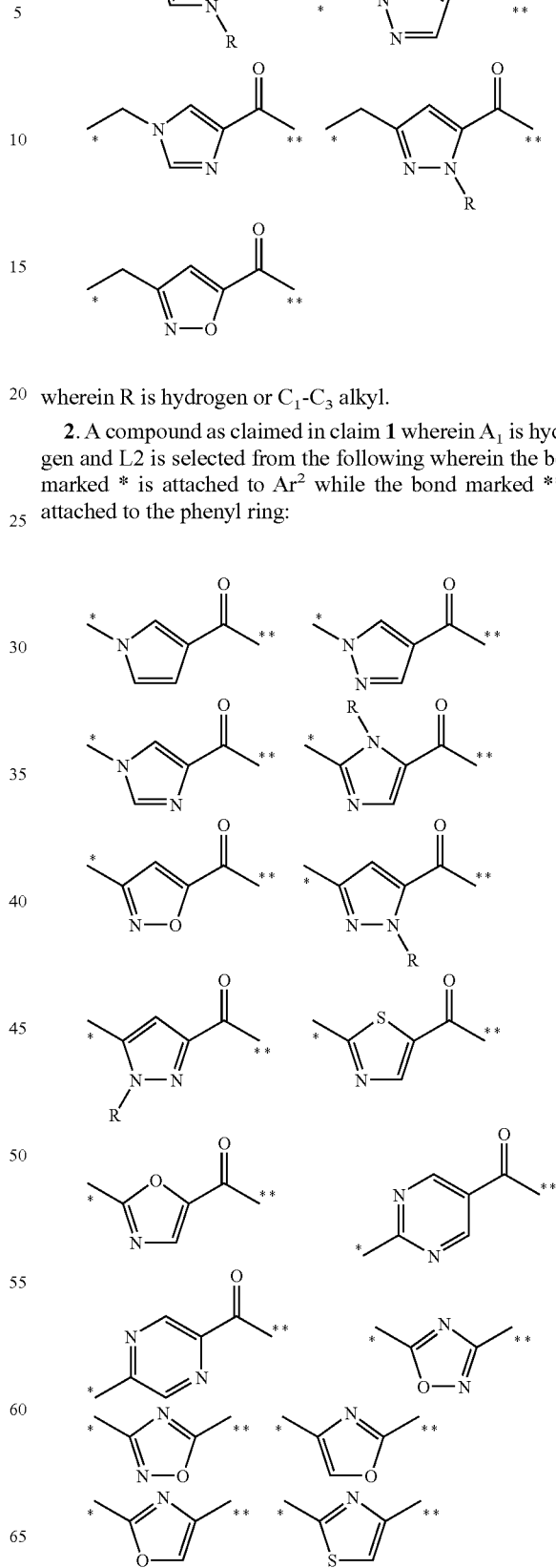
wherein R is hydrogen or $C_1$-$C_3$ alkyl.
2. A compound as claimed in claim 1 wherein $A_1$ is hydrogen and L2 is selected from the following wherein the bond marked * is attached to Ar² while the bond marked ** is attached to the phenyl ring:

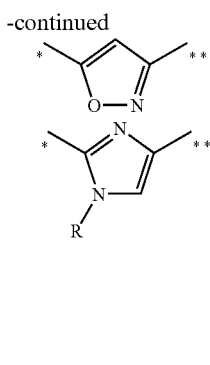

wherein R is hydrogen or $C_1$-$C_3$ alkyl.

3. A compound as claimed in claim 1 wherein A is —COOH.

4. A compound as claimed in claim 1 wherein $A_1$ is hydrogen.

5. An enantiomer of a compound as claimed in claim 1 wherein $A_1$ is methyl, and the carbon atom to which it is attached has the S stereochemical configuration.

6. A compound as claimed in claim 1 selected from the group consisting of:
4-chloro-2-(1-phenyl-1H-pyrazole-4-carbonyl)phenoxyacetic acid,
4-bromo-2-(1-phenyl-1H-pyrazole-4-carbonyl)phenoxyacetic acid,
[4-bromo-2-(1-pyridin-2-yl-1H-pyrazole-4-carbonyl)phenoxy]acetic acid,
{4-bromo-2-[1-(2-chlorophenyl)-1H-pyrazole-4-carbonyl]phenoxy}acetic acid,
{4-bromo-2-[1-(3-chlorophenyl)-1H-pyrazole-4-carbonyl]phenoxy}acetic acid,
{4-bromo-2-[1-(4-bromophenyl)-1H-pyrazole-4-carbonyl]phenoxy}acetic acid,
{4-bromo-2-[1-(4-chlorophenyl)-1H-pyrazole-4-carbonyl]phenoxy}acetic acid,
{4-bromo-2-[1-(2-ethylphenyl)-1H-pyrazole-4-carbonyl]phenoxy}acetic acid,
{4-bromo-2-[1-(2-bromophenyl)-1H-pyrazole-4-carbonyl]phenoxy}acetic acid,
{4-bromo-2-[1-(2-fluorophenyl)-1H-pyrazole-4-carbonyl]phenoxy}acetic acid,
{4-bromo-2-[1-(2-trifluoromethylphenyl)-1H-pyrazole-4-carbonyl]phenoxy}acetic acid,
{4-bromo-2-[1-(3-bromophenyl)-1H-pyrazole-4-carbonyl]phenoxy}acetic acid,
{4-bromo-2-[1-(2,4-dichlorophenyl)-1H-pyrazole-4-carbonyl]phenoxy}acetic acid,
{2-[1-(2-chlorophenyl)-1H-pyrazole-4-carbonyl]-4-nitrophenoxy}acetic acid,
{4-bromo-2-[1-(2,6-dichlorophenyl)-1H-pyrazole-4-carbonyl]phenoxy}acetic acid,
{2-[1-(2-bromophenyl)-1H-pyrazole-4-carbonyl]-4-ethylphenoxy}acetic acid,
{4-bromo-2-[1-(2,4-dibromophenyl)-1H-pyrazole-4-carbonyl]phenoxy}acetic acid,
{4-bromo-2-[1-(4-bromo-2-chlorophenyl)-1H-pyrazole-4-carbonyl]phenoxy}acetic acid,
{4-bromo-2-[1-(2,4,6-trichlorophenyl)-1H-pyrazole-4-carbonyl]phenoxy}acetic acid,
2-[4-bromo-2-(1-phenyl-1H-pyrazole-4-carbonyl)phenoxy]propionic acid,
(S)-2-[4-bromo-2-(1-phenyl-1H-pyrazole-4-carbonyl)phenoxy]propionic acid,
2-{4-Bromo-2-[1-(2-chlorophenyl)-1-H-pyrazole-4-carbonyl]phenoxy}propionic acid,
(S)-2-{4-Bromo-2-[1-(2-chlorophenyl)-1-H-pyrazole-4-carbonyl]phenoxy}-propionic acid,
2-{4-Bromo-2-[1-(2,6-dichlorophenyl)-1H-pyrazole-4-carbonyl]phenoxy}propionic acid,
(S)-2-{4-Bromo-2-[1-(2,6-dichlorophenyl)-1H-pyrazole-4-carbonyl]phenoxy}propionic acid,
{4-Bromo-2-[1-(2-ethoxyphenyl)-1H-pyrazole-4-carbonyl]phenoxy}acetic acid,
{4-Bromo-2-[1-(4-bromo-2-ethylphenyl)-1H-pyrazole-4-carbonyl]phenoxy}acetic acid,
{4-Bromo-2-[1-(2-phenoxyphenyl)-1H-pyrazole-4-carbonyl]phenoxy}acetic acid,
{4-Bromo-2-[1-(2-methylthiophenyl)-1H-pyrazole-4-carbonyl]phenoxy}acetic acid,
{4-Bromo-2-[1-(2-bromo-4-methylphenyl)-1H-pyrazole-4-carbonyl]phenoxy}acetic acid,
2-{4-Bromo-2-[1-(4-bromo-2-ethylphenyl)-1H-pyrazole-4-carbonyl]phenoxy}propionic acid,
2-{4-Bromo-2-[1-(2-phenoxyphenyl)-1H-pyrazole-4-carbonyl]phenoxy}propionic acid,
(S)-2-{4-Bromo-2-[1-(2-phenoxyphenyl)-1H-pyrazole-4-carbonyl]phenoxy}propionic acid,
2-{4-Bromo-2-[1-(2-methylthio)-1H-pyrazole-4-carbonyl]phenoxy}propionic acid,
(S)-2-{4-Bromo-2-[1-(2-methylthio)-1H-pyrazole-4-carbonyl]phenoxy}propionic acid,
{4-Bromo-2-[1-(2,4-dimethylphenyl)-1H-pyrazole-4-carbonyl]phenoxy}acetic acid,
{4-Bromo-2-[1-(4-chloro-2-methylphenyl)-1H-pyrazole-4-carbonyl]phenoxy}acetic acid,
{4-Bromo-2-[1-(2,5-dichlorophenyl)-1H-pyrazole-4-carbonyl]phenoxy}acetic acid,
2-{4-Bromo-2-[1-(4-chloro-2-methylphenyl)-1H-pyrazole-4-carbonyl]phenoxy}propionic acid,
2-{4-Bromo-2-[1-(2,4,6-trichlorophenyl)-1H-pyrazole-4-carbonyl]phenoxy}propionic acid,
{4-Bromo-2-[1-(2,6-diethyl-phenyl)-1H-pyrazole-4-carbonyl]phenoxy}acetic acid,
{4-Bromo-2-[1-(2,6-dimethylphenyl)-1H-pyrazole-4-carbonyl]phenoxy}acetic acid
{4-Bromo-2-[1-(2-ethyl-6-methylphenyl)-1H-pyrazole-4-carbonyl]phenoxy}acetic acid,
{4-Bromo-2-[1-(2-chloro-6-methylphenyl)-1H-pyrazole-4-carbonyl]phenoxy}acetic acid,
{4-Bromo-2-[1-(3,5-dichloropyridin-4-yl)-1H-pyrazole-4-carbonyl]phenoxy}acetic acid,
[4-Bromo-2-(1-naphthalen-1-yl-1H-pyrazole-4-carbonyl)phenoxy]acetic acid,
{4-Bromo-2-[2-(4-chlorobenzyl)thiazol-4-yl]phenoxy}acetic acid,
{4-Bromo-2-[3-(4-fluoro-phenyl)-[1,2,4]oxadiazol-5-yl]phenoxy}acetic acid,
{4-Bromo-2-[3-(4-methoxy-phenyl)-[1,2,4]oxadiazol-5-yl]phenoxy}acetic acid,
{4-Bromo-2-[3-(4-chlorophenyl)-[1,2,4]oxadiazol-5-yl]phenoxy}acetic acid,
{4-Bromo-2-[3-(4-fluoro-benzyl)-[1,2,4]oxadiazol-5-yl]-phenoxy}-acetic acid,
{4-Bromo-2-[3-(2,6-dichloro-benzyl)-[1,2,4]oxadiazol-5-yl]-phenoxy}-acetic acid,
{4-Bromo-2-[3-(2-trifluoromethylbenzyl)-[1,2,4]oxadiazol-5-yl]phenoxy}-acetic acid, 4-Bromo-2-[3-(2,6-dichloro-phenyl)isoxazole-5-carbonyl]phenoxy}acetic acid, {4-Bromo-2-[3-(1-phenylcyclopropyl)-[1,2,4]oxadiazol-5-yl]phenoxy}acetic acid, {4-Bromo-2-[3-(2,4-dichlorophenyl)-[1,2,4]oxadiazol-5-yl]phenoxy}acetic acid, and salts thereof.

7. A pharmaceutical composition comprising a compound as claimed in claim 1, together with a pharmaceutically acceptable carrier.

8. A compound of formula (IVA) or a salt thereof

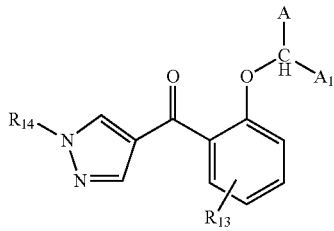

(IVA)

wherein A, $A_1$, and $R_{13}$ are as defined in any of claim 1 and $R_{14}$ is phenyl or 5- or 6-membered heteroaryl optionally substituted with up to four compatible substituents independently selected from $(C_1-C_6)$alkyl, $(C_1-C_6)$alkoxy, hydroxy, hydroxy$(C_1-C_6)$alkyl, mercapto, mercapto$(C_1-C_6)$alkyl, $(C_1-C_6)$alkylthio, halo including fluoro, bromo and chloro, fully or partially fluorinated $(C_1-C_3)$alkyl, $(C_1-C_3)$alkoxy or $(C_1-C_3)$alkylthio such as trifluoromethyl, trifluoromethoxy, and trifluoromethylthio, nitro, nitrile (—CN), oxo, phenyl, phenoxy, —COOR$^A$, —COR$^A$, —OCOR$^A$, —SO$_2$R$^A$, —CONR$^A$R$^B$, —SO$_2$NR$^A$R$^B$, —NR$^A$R$^B$, —OCONR$^A$R$^B$, —NR$^B$COR$^A$, —NR$^B$COOR$^A$, —NR$^B$SO$_2$OR$^A$ or —NR$^A$CONR$^A$R$^B$ wherein R$^A$ and R$^B$ are independently hydrogen or a $(C_1-C_6)$alkyl group or, in the case where R$^A$ and R$^B$ are linked to the same N atom, R$^A$ and R$^B$ taken together with that nitrogen may form a cyclic amino ring, and where the substituent is phenyl or phenoxy, the phenyl ring thereof may itself be substituted by any of the above substituents except phenyl or phenoxy.

9. A compound of formula (IVC) or a salt thereof

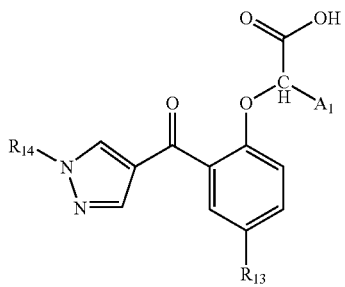

(IVC)

wherein $R_{13}$ represents a substituent selected from fluoro, chloro, bromo, iodo, $(C_1-C_6)$alkyl, trifluoromethyl, $(C_1-C_6)$alkoxy, $(C_1-C_6)$alkylmercapto, trifluoromethoxy, trifluoromethylthio, dimethylamino, cyano, $(C_1-C_3$alkyl)SO$_2$—, NH$_2$SO$_2$—, $(C_1-C_3$alkyl)NHSO$_2$—, $(C_1-C_3$alkyl)$_2$NSO$_2$—, and nitro, and $R_{14}$ is as defined in claim 8.

10. A compound as claimed in claim 9 wherein $R_{14}$ is a 2-substituted, 2,4-disubstituted, 2,6-disubstituted or 2,4,6-trisubstituted phenyl ring where the substituents are selected from fluoro, chloro, bromo, iodo, $(C_1-C_6)$alkyl, trifluoromethyl, $(C_1-C_6)$alkoxy, $(C_1-C_6)$alkylmercapto, trifluoromethoxy, trifluoromethylthio, dimethylamino, $(C_1-C_3$alkyl)SO$_2$—, NH$_2$SO$_2$—, $(C_1-C_3$alkyl)NHSO$_2$—, $(C_1-C_3$alkyl)$_2$NSO$_2$—, and cyano.

11. A compound as claimed in claim 9 wherein $R_{14}$ is a 2-substituted, 2,4-disubstituted, or 2,6-disubstituted phenyl ring where the substituents are selected from fluoro, chloro, $(C_1-C_3)$alkyl, trifluoromethyl, $(C_1-C_3)$alkoxy, $(C_1-C_3)$alkylmercapto, trifluoromethoxy, trifluoromethylthio, and cyano.

12. A compound as claimed in claim 9 wherein $R_{14}$ is a 2-substituted or 2,6-disubstituted pyridyl ring where the substituents are selected from fluoro, chloro, $(C_1-C_3)$alkyl, trifluoromethyl, $(C_1-C_3)$alkoxy, $(C_1-C_3)$alkylmercapto, trifluoromethoxy, trifluoromethylthio, and cyano.

13. A compound as claimed in claim 9 wherein $R_{13}$ is selected from fluoro, chloro, bromo, iodo, $(C_1-C_6)$alkyl, $(C_1-C_6)$alkoxy, trifluoromethoxy and trifluoromethylthio, and $R_{14}$ is optionally substituted phenyl or optionally substituted 5- or 6-membered heteroaryl.

14. The compound {4-bromo-2-[1-(2,6-dichlorophenyl)-1H-pyrazole-4-carbonyl]phenoxy}acetic acid having the formula

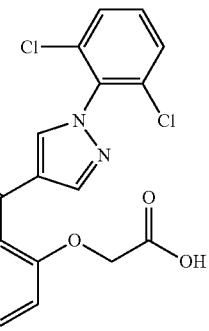

and salts thereof.

* * * * *

SEQUENCE LISTING

<160> NUMBER OF SEQ ID NOS: 2

<210> SEQ ID NO 1
<211> LENGTH: 395
<212> TYPE: PRT
<213> ORGANISM: Homo sapiens

<400> SEQUENCE: 1

```
Met Ser Ala Asn Ala Thr Leu Lys Pro Leu Cys Pro Ile Leu Glu Gln
 1               5                  10                  15

Met Ser Arg Leu Gln Ser His Ser Asn Thr Ser Ile Arg Tyr Ile Asp
                20                  25                  30

His Ala Ala Val Leu Leu His Gly Leu Ala Ser Leu Leu Gly Leu Val
            35                  40                  45

Glu Asn Gly Val Ile Leu Phe Val Val Gly Cys Arg Met Arg Gln Thr
        50                  55                  60

Val Val Thr Thr Trp Val Leu His Leu Ala Leu Ser Asp Leu Leu Ala
65                  70                  75                  80
```

```
Ser Ala Ser Leu Pro Phe Phe Thr Tyr Phe Leu Ala Val Gly His Ser
                85                  90                  95

Trp Glu Leu Gly Thr Thr Phe Cys Lys Leu His Ser Ser Ile Phe Phe
            100                 105                 110

Leu Asn Met Phe Ala Ser Gly Phe Leu Ser Ala Ile Ser Leu Asp
        115                 120                 125

Arg Cys Leu Gln Val Val Arg Pro Val Trp Ala Gln Asn His Arg Thr
        130                 135                 140

Val Ala Ala Ala His Lys Val Cys Leu Val Leu Trp Ala Leu Ala Val
145                 150                 155                 160

Leu Asn Thr Val Pro Tyr Phe Val Phe Arg Asp Thr Ile Ser Arg Leu
                165                 170                 175

Asp Gly Arg Ile Met Cys Tyr Tyr Asn Val Leu Leu Leu Asn Pro Gly
                180                 185                 190

Pro Asp Arg Asp Ala Thr Cys Asn Ser Arg Gln Ala Ala Leu Ala Val
            195                 200                 205

Ser Lys Phe Leu Leu Ala Phe Leu Val Pro Leu Ala Ile Ile Ala Ser
        210                 215                 220

Ser His Ala Ala Val Ser Leu Arg Leu Gln His Arg Gly Arg Arg Arg
225                 230                 235                 240

Pro Gly Arg Phe Val Arg Leu Val Ala Ala Val Val Ala Ala Phe Ala
                245                 250                 255

Leu Cys Trp Gly Pro Tyr His Val Phe Ser Leu Leu Glu Ala Arg Ala
                260                 265                 270

His Ala Asn Pro Gly Leu Arg Pro Leu Val Trp Arg Gly Leu Pro Phe
            275                 280                 285

Val Thr Ser Leu Ala Phe Phe Asn Ser Val Ala Asn Pro Val Leu Tyr
290                 295                 300

Val Leu Thr Cys Pro Asp Met Leu Arg Lys Leu Arg Arg Ser Leu Arg
305                 310                 315                 320

Thr Val Leu Glu Ser Val Leu Val Asp Asp Ser Glu Leu Gly Gly Ala
            325                 330                 335

Gly Ser Ser Arg Arg Arg Thr Ser Ser Thr Ala Arg Ser Ala Ser
        340                 345                 350

Pro Leu Ala Leu Cys Ser Arg Pro Glu Glu Pro Arg Gly Pro Ala Arg
        355                 360                 365

Leu Leu Gly Trp Leu Leu Gly Ser Cys Ala Ala Ser Pro Gln Thr Gly
        370                 375                 380

Pro Leu Asn Arg Ala Leu Ser Ser Thr Ser Ser
385                 390                 395

<210> SEQ ID NO 2
<211> LENGTH: 1188
<212> TYPE: DNA
<213> ORGANISM: Homo sapiens

<400> SEQUENCE: 2
atgtcggcca acgccacact gaagccactc tgccccatcc tggagcagat gagccgtctc      60
cagagccaca gcaacaccag catccgctac atcgaccacg cggccgtgct gctgcacggg     120
ctggcctcgc tgctgggcct ggtggagaat ggagtcatcc tcttcgtggt gggctgccgc     180
atgcgccaga ccgtggtcac cacctgggtg ctgcacctgg cgctgtccga cctgttggcc     240
tctgcttccc tgcccttctt cacctacttc ttggccgtgg gccactcgtg ggagctgggc     300
accaccttct gcaaactgca ctcctccatc ttctttctca acatgttcgc cagcggcttc     360
```

```
ctgctcagcg ccatcagcct ggaccgctgc ctgcaggtgg tgcggccggt gtgggcgcag    420
aaccaccgca ccgtggccgc ggcgcacaaa gtctgcctgc tgctttgggc actagcggtg    480
ctcaacacgg tgccctattt cgtgttccgg gacaccatct cgcggctgga cgggcgcatt    540
atgtgctact acaatgtgct gctcctgaac ccggggcctg accgcgatgc cacgtgcaac    600
tcgcgccagg cggccctggc cgtcagcaag ttcctgctgg ccttcctggt gccgctggcg    660
atcatcgcct cgagccacgc ggccgtgagc ctgcggttgc agcaccgcgg ccgccggcgg    720
ccaggccgct tcgtgcgcct ggtggcagcc gtcgtggccg ccttcgcgct ctgctggggg    780
ccctaccacg tgttcagcct gctggaggcg cgggcgcacg caaacccggg gctgcggccg    840
ctcgtgtggc gcgggctgcc cttcgtcacc agcctggcct tcttcaacag cgtggccaac    900
ccggtgctct acgtgctcac ctgccccgac atgctgcgca agctgcggcg ctcgctgcgc    960
acggtgctgg agagcgtgct ggtggacgac agcgagctgg gtggcgcggg aagcagccgc   1020
cgccgccgca cctcctccac cgcccgctcg gcctcccctt tagctctctg cagccgcccg   1080
gaggaaccgc ggggccccgc gcgtctcctc ggctggctgc tgggcagctg cgcagcgtcc   1140
ccgcagacgg gcccctgaa  ccgggcgctg agcagcacct cgagttag                1188
```